United States Patent
Brady et al.

(10) Patent No.: US 12,064,516 B2
(45) Date of Patent: Aug. 20, 2024

(54) PHARMACEUTICAL FORMULATIONS AND USES THEREOF

(71) Applicant: Aldeyra Therapeutics, Inc., Lexington, MA (US)

(72) Inventors: Todd Brady, Carlisle, MA (US); Adam Brockman, Arlington, MA (US); Stephen Gitu Machatha, Wilmington, MA (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 169 days.

(21) Appl. No.: 17/333,528

(22) Filed: May 28, 2021

(65) Prior Publication Data

US 2021/0393527 A1  Dec. 23, 2021

Related U.S. Application Data

(63) Continuation of application No. PCT/US2021/032335, filed on May 13, 2021.

(60) Provisional application No. 63/024,193, filed on May 13, 2020.

(51) Int. Cl.
| | |
|---|---|
| *A61K 9/20* | (2006.01) |
| *A61K 9/00* | (2006.01) |
| *A61K 9/16* | (2006.01) |
| *A61K 9/48* | (2006.01) |
| *A61K 31/47* | (2006.01) |
| *A61P 11/00* | (2006.01) |

(52) U.S. Cl.
CPC .......... *A61K 9/1623* (2013.01); *A61K 9/0053* (2013.01); *A61K 9/1611* (2013.01); *A61K 9/1635* (2013.01); *A61K 9/1652* (2013.01); *A61K 31/47* (2013.01); *A61P 11/00* (2018.01); *A61K 9/20* (2013.01); *A61K 9/48* (2013.01)

(58) Field of Classification Search
None
See application file for complete search history.

(56) References Cited

U.S. PATENT DOCUMENTS

| | | |
|---|---|---|
| 2,086,186 A | 7/1937 | Messer |
| 3,912,748 A | 10/1975 | Evans et al. |
| 4,668,626 A | 5/1987 | Kobayashi et al. |

(Continued)

FOREIGN PATENT DOCUMENTS

| | | |
|---|---|---|
| CA | 3032609 A1 | 3/2018 |
| CN | 1830964 A | 9/2006 |

(Continued)

OTHER PUBLICATIONS

Reproxalap (Medchem Express, 2013. 3 pages (Year: 2013).*

(Continued)

*Primary Examiner* — Lakshmi S Channavajjala
(74) *Attorney, Agent, or Firm* — Dechert LLP; Andrea L. C. Reid; Joseph W. Arico

(57) ABSTRACT

The present invention relates to pharmaceutical compositions and unit dosage forms comprising a quinoline compound, or a pharmaceutically acceptable salt thereof, which are useful for treatment of a disease, disorder, or condition such as inflammatory diseases, respiratory diseases, organ diseases, viral infections, and sequelae and associated conditions such as acute respiratory distress syndrome.

10 Claims, 7 Drawing Sheets

(56) References Cited

U.S. PATENT DOCUMENTS

| | | |
|---|---|---|
| 4,956,351 A | 9/1990 | Mesens et al. |
| 5,024,998 A | 6/1991 | Bodor |
| 5,032,392 A | 7/1991 | Varma |
| 5,364,637 A | 11/1994 | De et al. |
| 5,376,645 A | 12/1994 | Stella et al. |
| 5,419,898 A | 5/1995 | Ikejiri et al. |
| 5,472,954 A | 12/1995 | Loftsson |
| 5,493,027 A | 2/1996 | Nichols et al. |
| 5,576,311 A | 11/1996 | Guy |
| 5,668,117 A | 9/1997 | Shapiro |
| 5,767,109 A | 6/1998 | Sanchez et al. |
| 5,998,488 A | 12/1999 | Shinohara et al. |
| 6,107,300 A | 8/2000 | Bakthavatchalam et al. |
| 6,191,127 B1 | 2/2001 | Holscher et al. |
| 6,358,948 B1 | 3/2002 | Zhang et al. |
| 6,444,221 B1 | 9/2002 | Shapiro |
| 6,492,520 B1 | 12/2002 | Chen |
| 6,498,154 B1 | 12/2002 | Grubb et al. |
| 6,515,010 B1 | 2/2003 | Franchini et al. |
| 6,525,056 B2 | 2/2003 | Arvanitis et al. |
| 6,569,879 B2 | 5/2003 | Liu et al. |
| 7,083,803 B2 | 8/2006 | Peyman |
| 7,297,709 B2 | 11/2007 | Dai et al. |
| 7,531,564 B2 | 5/2009 | Malamas et al. |
| 7,563,906 B2 | 7/2009 | Hagihara et al. |
| 7,842,312 B2 | 11/2010 | Burgermeister et al. |
| 7,956,189 B2 | 6/2011 | Chen et al. |
| 7,973,025 B2 | 7/2011 | Jordan et al. |
| 7,982,071 B2 | 7/2011 | Scott et al. |
| 8,158,609 B1 | 4/2012 | Marsh et al. |
| 8,435,965 B2 | 5/2013 | Tabuchi et al. |
| 8,575,221 B2 | 11/2013 | Masse et al. |
| 8,722,669 B2 | 5/2014 | Palczewski et al. |
| 8,791,154 B2 | 7/2014 | Gamache et al. |
| 8,940,721 B2 | 1/2015 | Jordan et al. |
| 8,940,764 B2 | 1/2015 | Jordan et al. |
| 9,067,963 B2 | 6/2015 | Thompson et al. |
| 9,084,730 B2 | 7/2015 | Bedos et al. |
| 9,259,427 B2 | 2/2016 | Tierney et al. |
| 9,265,759 B2 | 2/2016 | Jordan et al. |
| 9,364,430 B2 * | 6/2016 | Babul ............... A61K 9/1635 |
| 9,364,471 B2 | 6/2016 | Jordan et al. |
| 9,375,408 B2 | 6/2016 | Singh |
| 9,562,039 B2 | 2/2017 | Julia Jane et al. |
| 9,604,997 B2 | 3/2017 | Jordan et al. |
| 9,650,342 B2 | 5/2017 | Jordan et al. |
| 9,687,481 B2 | 6/2017 | Brady et al. |
| 9,814,701 B2 | 11/2017 | Jordan et al. |
| 9,817,701 B2 | 11/2017 | Baptist et al. |
| 9,896,419 B2 | 2/2018 | Jordan et al. |
| 10,058,095 B2 | 8/2018 | Czarnik |
| 10,098,894 B2 | 10/2018 | Persicaner et al. |
| 10,111,862 B2 | 10/2018 | Chabala et al. |
| 10,202,348 B2 | 2/2019 | Jordan et al. |
| 10,213,395 B2 | 2/2019 | Brady et al. |
| 10,414,732 B2 | 9/2019 | Buist et al. |
| 10,426,790 B2 | 10/2019 | Young et al. |
| 10,463,687 B2 | 11/2019 | Rodriguez-Boulan et al. |
| 10,543,181 B2 | 1/2020 | Brady et al. |
| 10,550,085 B2 | 2/2020 | Brady et al. |
| 10,588,874 B2 | 3/2020 | Brady et al. |
| 10,736,842 B2 | 8/2020 | Misra |
| 10,744,144 B2 | 8/2020 | Shah |
| 10,781,158 B2 | 9/2020 | Singh |
| 10,864,166 B2 | 12/2020 | Venkatesh et al. |
| 10,913,722 B2 | 2/2021 | Jordan et al. |
| 11,007,157 B2 | 5/2021 | Brady et al. |
| 11,040,039 B2 | 6/2021 | Macdonald et al. |
| 11,046,650 B2 | 6/2021 | Brady et al. |
| 11,129,823 B2 | 9/2021 | Brady et al. |
| 11,197,821 B2 | 12/2021 | Clark et al. |
| 11,312,692 B1 | 4/2022 | Machatha et al. |
| 11,459,300 B2 | 10/2022 | Brady et al. |
| 11,583,529 B2 | 2/2023 | Macdonald et al. |
| 11,701,331 B2 | 7/2023 | Brady et al. |
| 11,724,987 B2 | 8/2023 | Jordan et al. |
| 11,786,518 B2 | 10/2023 | Clark et al. |
| 11,845,722 B2 | 12/2023 | Brady et al. |
| 2004/0132636 A1 | 7/2004 | Dooley et al. |
| 2004/0198828 A1 | 10/2004 | Abelson et al. |
| 2004/0235892 A1 | 11/2004 | Dai et al. |
| 2005/0020603 A1 | 1/2005 | Dai et al. |
| 2005/0090553 A1 | 4/2005 | Shapiro |
| 2005/0130906 A1 | 6/2005 | Matier et al. |
| 2005/0197292 A1 | 9/2005 | Smithson et al. |
| 2005/0234018 A1 | 10/2005 | Lyons et al. |
| 2006/0014786 A1 | 1/2006 | Raut |
| 2006/0111318 A1 | 5/2006 | Okamoto |
| 2006/0183909 A1 | 8/2006 | Schmitt et al. |
| 2006/0189608 A1 | 8/2006 | Bingaman |
| 2006/0257488 A1 | 11/2006 | Hubbard |
| 2007/0129404 A1 | 6/2007 | Hagihara et al. |
| 2007/0135481 A1 | 6/2007 | Jordan et al. |
| 2007/0243257 A1 | 10/2007 | Bedos et al. |
| 2007/0297981 A1 | 12/2007 | Ousler et al. |
| 2008/0108818 A1 | 5/2008 | Chen et al. |
| 2008/0241256 A1 | 10/2008 | Kuhn |
| 2009/0118503 A1 | 5/2009 | Sprott et al. |
| 2009/0182009 A1 | 7/2009 | Jordan et al. |
| 2010/0160304 A1 | 6/2010 | Katayama |
| 2010/0240624 A1 | 9/2010 | Chapin et al. |
| 2010/0331315 A1 | 12/2010 | Haddach et al. |
| 2011/0071091 A1 | 3/2011 | Chowhan et al. |
| 2011/0105450 A1 | 5/2011 | Chapin et al. |
| 2011/0257271 A1 | 10/2011 | Masse et al. |
| 2011/0263645 A1 | 10/2011 | Jordan et al. |
| 2012/0108585 A1 | 5/2012 | Vu |
| 2012/0295967 A1 | 11/2012 | Gamache et al. |
| 2012/0302601 A1 | 11/2012 | Jordan et al. |
| 2013/0165419 A1 | 6/2013 | Lindstrom et al. |
| 2013/0190500 A1 | 7/2013 | Greiner et al. |
| 2014/0038918 A1 | 2/2014 | Rodriguez-Boulan et al. |
| 2014/0050797 A1 | 2/2014 | Venkatesh et al. |
| 2014/0235604 A1 | 8/2014 | Palczewski et al. |
| 2014/0235722 A1 | 8/2014 | Jordine et al. |
| 2015/0209333 A1 | 7/2015 | Jordan et al. |
| 2015/0209345 A1 | 7/2015 | Jordan et al. |
| 2015/0258120 A1 | 9/2015 | Zarnitsyn et al. |
| 2015/0335632 A1 | 11/2015 | Brady et al. |
| 2015/0344432 A1 | 12/2015 | Jordan et al. |
| 2015/0344447 A1 | 12/2015 | Chabala et al. |
| 2016/0009698 A1 | 1/2016 | Julia Jane et al. |
| 2016/0030449 A1 | 2/2016 | Persicaner et al. |
| 2016/0052930 A1 | 2/2016 | Fensome et al. |
| 2016/0136231 A1 | 5/2016 | Gadek |
| 2016/0151381 A1 | 6/2016 | Blackburn et al. |
| 2016/0168098 A1 | 6/2016 | Jordan et al. |
| 2017/0029354 A1 | 2/2017 | Singh |
| 2017/0095449 A1 | 4/2017 | Winters et al. |
| 2017/0143627 A1 | 5/2017 | Misra |
| 2017/0239196 A1 | 8/2017 | Brady et al. |
| 2017/0266220 A1 | 9/2017 | Young et al. |
| 2017/0320829 A1 | 11/2017 | Jordan et al. |
| 2017/0354655 A1 | 12/2017 | Beaupre et al. |
| 2018/0050989 A1 | 2/2018 | Machatha et al. |
| 2018/0092882 A1 | 4/2018 | Jordan et al. |
| 2018/0194733 A1 | 7/2018 | Jordan et al. |
| 2018/0235980 A1 | 8/2018 | Shah |
| 2018/0250306 A1 | 9/2018 | Brady et al. |
| 2018/0265474 A1 | 9/2018 | Buist et al. |
| 2018/0354905 A1 | 12/2018 | Brady et al. |
| 2019/0054023 A1 | 2/2019 | Seaman et al. |
| 2019/0087646 A1 | 3/2019 | Goulden et al. |
| 2019/0105322 A1 | 4/2019 | Macdonald et al. |
| 2019/0125729 A1 | 5/2019 | Chabala et al. |
| 2019/0183878 A1 | 6/2019 | Brady et al. |
| 2019/0210971 A1 | 7/2019 | Jordan et al. |
| 2019/0231715 A1 | 8/2019 | Brady et al. |
| 2019/0247334 A1 | 8/2019 | Brady et al. |
| 2020/0038392 A1 | 2/2020 | Brady et al. |
| 2020/0062712 A1 | 2/2020 | Machatha et al. |
| 2020/0121591 A1 | 4/2020 | Clark et al. |
| 2020/0199075 A1 | 6/2020 | Brady et al. |
| 2020/0246345 A1 | 8/2020 | Brady et al. |

(56) References Cited

U.S. PATENT DOCUMENTS

| | | |
|---|---|---|
| 2020/0323841 A1 | 10/2020 | Clark et al. |
| 2020/0368182 A1 | 11/2020 | Brady et al. |
| 2021/0269402 A1 | 9/2021 | Jordan et al. |
| 2021/0275469 A1 | 9/2021 | Brady et al. |
| 2021/0317385 A1 | 10/2021 | Macdonald et al. |
| 2021/0347735 A1 | 11/2021 | Brady et al. |
| 2021/0353628 A1 | 11/2021 | Macdonald et al. |
| 2021/0393527 A1 | 12/2021 | Brady et al. |
| 2021/0393612 A1 | 12/2021 | Machatha et al. |
| 2022/0017475 A1 | 1/2022 | Machatha et al. |
| 2022/0089542 A1 | 3/2022 | Machatha et al. |
| 2022/0133629 A1 | 5/2022 | Clark et al. |
| 2022/0133697 A1 | 5/2022 | Machatha et al. |
| 2022/0184057 A1 | 6/2022 | Brady et al. |
| 2022/0202745 A1 | 6/2022 | Brady et al. |
| 2022/0211691 A1 | 7/2022 | Brady et al. |
| 2022/0354857 A1 | 11/2022 | Brady et al. |
| 2023/0041335 A1 | 2/2023 | Jordan et al. |
| 2023/0131929 A1 | 4/2023 | Brady et al. |
| 2023/0149383 A1 | 5/2023 | Brady et al. |
| 2023/0174491 A1 | 6/2023 | Brady et al. |
| 2023/0228744 A1 | 7/2023 | Brady et al. |
| 2023/0248727 A1 | 8/2023 | Macdonald et al. |
| 2023/0293527 A1 | 9/2023 | Macdonald et al. |

FOREIGN PATENT DOCUMENTS

| | | | |
|---|---|---|---|
| CN | 1882339 | A | 12/2006 |
| CN | 101048384 | A | 10/2007 |
| CN | 101321742 | A | 12/2008 |
| CN | 101534826 | A | 9/2009 |
| CN | 101611009 | A | 12/2009 |
| CN | 104884049 | A | 9/2015 |
| CN | 105120866 | A | 12/2015 |
| CN | 105704440 | A | 6/2016 |
| CN | 108135867 | A | 6/2018 |
| CN | 109640983 | A | 4/2019 |
| CN | 111527530 | A | 8/2020 |
| CN | 112541870 | A | 3/2021 |
| CN | 112800947 | A | 5/2021 |
| CN | 113168511 | A | 7/2021 |
| EP | 0186367 | A2 | 7/1986 |
| EP | 0245054 | A1 | 11/1987 |
| EP | 0483881 | A1 | 5/1992 |
| EP | 1621199 | A1 | 2/2006 |
| EP | 1679308 | A1 | 7/2006 |
| EP | 1888548 | A1 | 2/2008 |
| EP | 2301549 | A1 | 3/2011 |
| GB | 2327672 | A | 2/1999 |
| JP | H04264422 | A | 9/1992 |
| JP | H06239748 | A | 8/1994 |
| JP | H07025758 | A | 1/1995 |
| JP | H08175985 | A | 7/1996 |
| JP | H09169647 | A | 6/1997 |
| JP | H09285529 | A | 11/1997 |
| JP | H10306022 | A | 11/1998 |
| JP | 2001041757 | A | 2/2001 |
| JP | 2001318350 | A | 11/2001 |
| JP | 2002003364 | A | 1/2002 |
| JP | 2003519698 | A | 6/2003 |
| JP | 2005132834 | A | 5/2005 |
| JP | 2005187407 | A | 7/2005 |
| JP | 3736916 | B2 | 1/2006 |
| JP | 2006008568 | A | 1/2006 |
| JP | 2007532648 | A | 11/2007 |
| JP | 2008542291 | A | 11/2008 |
| JP | 4466875 | B2 | 5/2010 |
| JP | 4748289 | B2 | 8/2011 |
| JP | 2011203665 | A | 10/2011 |
| JP | 2012506449 | A | 3/2012 |
| JP | 5194218 | B2 | 5/2013 |
| JP | 2014515355 | A | 6/2014 |
| JP | 2015057437 | A | 3/2015 |
| JP | 2015535293 | A | 12/2015 |
| JP | 2016508994 | A | 3/2016 |
| JP | 2018530524 | A | 10/2018 |
| JP | 2019507756 | A | 3/2019 |
| KR | 20180073554 | A | 7/2018 |
| RU | 2010137842 | A | 3/2012 |
| RU | 2565448 | C2 | 10/2015 |
| SU | 50906 | A1 | 11/1936 |
| SU | 509046 | A1 | 6/1984 |
| WO | WO-199507274 | A1 | 3/1995 |
| WO | WO-1996022992 | A1 | 8/1996 |
| WO | WO-1998005645 | A1 | 2/1998 |
| WO | WO-1999046237 | A1 | 9/1999 |
| WO | WO-2001041757 | A1 | 6/2001 |
| WO | WO0151919 | A2 | 7/2001 |
| WO | WO-2004082622 | A2 | 9/2004 |
| WO | WO-2004091630 | A1 | 10/2004 |
| WO | WO-2005035506 | A1 | 4/2005 |
| WO | WO-2005040151 | A1 | 5/2005 |
| WO | WO-2005051328 | A2 | 6/2005 |
| WO | WO-2005079774 | A2 | 9/2005 |
| WO | WO-2005105067 | A2 | 11/2005 |
| WO | WO-2006000421 | A2 | 1/2006 |
| WO | WO-2006002473 | A1 | 1/2006 |
| WO | WO-2006049968 | A1 | 5/2006 |
| WO | WO-2006077821 | A1 | 7/2006 |
| WO | WO-2006127945 | A1 | 11/2006 |
| WO | WO-2007118276 | A1 | 10/2007 |
| WO | WO-2008014602 | A1 | 2/2008 |
| WO | WO2008052086 | A1 | 5/2008 |
| WO | WO-2009045479 | A1 | 4/2009 |
| WO | WO-2009102418 | A1 | 8/2009 |
| WO | WO-2010048332 | A2 | 4/2010 |
| WO | WO-2010133672 | A1 | 11/2010 |
| WO | WO-2011008202 | A1 | 1/2011 |
| WO | WO-2011071995 | A2 | 6/2011 |
| WO | WO-2011072141 | A1 | 6/2011 |
| WO | WO-2011078204 | A1 | 6/2011 |
| WO | WO-2012097173 | A2 | 7/2012 |
| WO | WO-2012105887 | A1 | 8/2012 |
| WO | WO-2014100425 | A1 | 6/2014 |
| WO | WO-2014116593 | A1 | 7/2014 |
| WO | WO-2014116836 | A2 | 7/2014 |
| WO | WO-2015002893 | A1 | 1/2015 |
| WO | WO-2015187942 | A1 | 12/2015 |
| WO | WO-2016085939 | A2 | 6/2016 |
| WO | WO-2016165626 | A1 | 10/2016 |
| WO | WO-2017035077 | A1 | 3/2017 |
| WO | WO-2017035082 | A1 | 3/2017 |
| WO | WO-2017147617 | A1 | 8/2017 |
| WO | WO-2017196881 | A1 * | 11/2017 ............. A61K 31/47 |
| WO | WO-2017196881 | A1 | 11/2017 |
| WO | WO-2017214201 | A1 | 12/2017 |
| WO | WO-2018039192 | A1 | 3/2018 |
| WO | WO-2018039197 | A1 | 3/2018 |
| WO | WO-2018064354 | A1 | 4/2018 |
| WO | WO-2018067860 | A1 | 4/2018 |
| WO | WO2018071619 | A1 | 4/2018 |
| WO | WO2018091859 | A1 | 5/2018 |
| WO | WO-2018170476 | A1 | 9/2018 |
| WO | WO-2019075136 | A1 | 4/2019 |
| WO | WO-2020018498 | A1 | 1/2020 |
| WO | WO-2020028820 | A1 | 2/2020 |
| WO | WO-2020033344 | A1 | 2/2020 |
| WO | WO-2020068986 | A1 | 4/2020 |
| WO | WO-2020072621 | A1 | 4/2020 |
| WO | WO-2020118045 | A1 | 6/2020 |
| WO | WO-2020198064 | A1 | 10/2020 |
| WO | WO-2020223685 | A1 | 11/2020 |
| WO | WO-2020223717 | A1 | 11/2020 |
| WO | WO-2021051003 | A1 | 3/2021 |
| WO | WO-2021195211 | A1 | 9/2021 |
| WO | WO-2021211625 | A1 | 10/2021 |
| WO | WO-2021231792 | A1 | 11/2021 |
| WO | WO-2021248031 | A1 | 12/2021 |

(56) References Cited

FOREIGN PATENT DOCUMENTS

| WO | WO-2022150580 A1 | 7/2022 |
|---|---|---|
| WO | WO-2023278816 A1 | 1/2023 |

OTHER PUBLICATIONS

Maghsoodi et al AAPS PharmSciTechTech 2009, vol. 10, No. 1, Mar. 2009—Physicomechanical properties of naproxen-loaded microparticles prepared from Eudragit L100). 120-128 (Year: 2009).*
Abelson and Loeffler, "Conjunctival allergen challenge: models in the investigation of ocular allergy," Curr Allergy Asthma Rep. 2003;3(4):363-8.
Abelson and Spitalny, "Combined analysis of two studies using the conjunctival allergen challenge model to evaluate olopatadine hydrochloride, a new ophthalmic antiallergic agent with dual activity," Am J Ophthalmol. 1998; 125(6):797-804.
Abelson et al., "Conjunctival allergen challenge. A clinical approach to studying allergic conjunctivitis," Arch Ophthalmol. 1990;108(1):84-8.
Abelson et al., "The conjunctival provocation test model of ocular allergy: utility for assessment of an ocular corticosteroid, loteprednol etabonate," J Ocul Pharmacol Ther. 1998;14(6):533-42.
Abramovitz et al., "The utilization of recombinant prostanoid receptors to determine the affinities and selectivities of prostaglandins and related analogs," Biochim Biophys Acta. 2000;1483(2):285-93.
Ackerman et al., "Ocular itch associated with allergic conjunctivitis: latest evidence and clinical management," Ther Adv Chronic Dis. 2016;7(1):52-67.
Acland et al., "Gene therapy restores vision in a canine model of childhood blindness," Nat Genet. 2001;28(1):92-5.
Aharony et al., "Pharmacological characterization of cloned human NK-2 (neurokinin A) receptor expressed in a baculovirus/Sf-21 insect cell system," Mol Pharmacol. 1993;44(2):356-63.
Aktürk et al., "Nitric oxide and malondialdehyde levels in plasma and tissue of psoriasis patients," J Eur Acad Dermatol Venereol. 2012;26(7):833-7.
Al-Bari, "Chloroquine analogues in drug discovery: new directions of uses, mechanisms of actions and toxic manifestations from malaria to multifarious diseases," J Antimicrob Chemother. 2015;70(6):1608-21.
Al-Essa et al., "Clinical, fluorine-18 labeled 2-fluoro-2-deoxyglucose positron emission tomography (FDG PET), MRI of the brain and biochemical observations in a patient with 4-hydroxybutyric aciduria; a progressive neurometabolic disease," Brain Dev. 2000;22(2):127-31.
Al-Hasani et al., "Phosphoryl exchange is involved in the mechanism of the insulin receptor kinase," FEBS Lett. 1994;349(1):17-22.
Albano et al., "Immune response towards lipid peroxidation products as a predictor of progression of non-alcoholic fatty liver disease to advanced fibrosis," Gut. 2005;54(7):987-93.
Aldeyra Therapeutics, "Aldeyra Therapeutics Abstract Accepted at 2015 American Academy of Allergy Asthma & Immunology Annual Meeting: Novel Anti-Inflammatory Data Selected for Late-Breaking Poster Presentation," Press Release. 2014.
Aldeyra Therapeutics, "Aldeyra Therapeutics Abstract Accepted for Presentation at the 2015 Multinational Association of Supportive Care in Cancer-International Society of Oral Oncology (MASCCISOO) Annual Meeting," Press Release. 2015.
Aldeyra Therapeutics, "Aldeyra Therapeutics Abstracts Accepted for Presentation at the 2015 Annual Meeting of the Association for Research in Vision and Ophthalmology," Press Release. 2015.
Aldeyra Therapeutics, "Aldeyra Therapeutics Announces Agreement with Johnson & Johnson Innovation to Advance Novel Immune-Modulating Drugs for Systemic Inflammatory Diseases," Press Release. 2018.
Aldeyra Therapeutics, "Aldeyra Therapeutics Announces Clinical Development Update for Phase 3 Programs," Press Release. 2017.
Aldeyra Therapeutics, "Aldeyra Therapeutics Announces Collaboration With the National Organization for Rare Disorders to Enhance Awareness for Sjogren-Larsson Syndrome Patients," Press Release. 2014.
Aldeyra Therapeutics, "Aldeyra Therapeutics Announces Development Programs at 2018 Research Day," Press Release. 2018.
Aldeyra Therapeutics, "Aldeyra Therapeutics Announces First Patient Enrolled in Allergic Conjunctivitis Phase 2b Clinical Trial," Press Release. 2017.
Aldeyra Therapeutics, "Aldeyra Therapeutics Announces First Patient Enrolled in Allergic Conjunctivitis Phase 3 Clinical Trial," Press Release. 2018.
Aldeyra Therapeutics, "Aldeyra Therapeutics Announces First Patient Enrolled in Allergic Conjunctivitis Phase IIa Clinical Trial," Press Release. 2015.
Aldeyra Therapeutics, "Aldeyra Therapeutics Announces First Patient Enrolled in Dry Eye Disease Phase 2a Clinical Trial," Press Release. 2017.
Aldeyra Therapeutics, "Aldeyra Therapeutics Announces First Patient Enrolled in Dry Eye Disease Phase 2b Clinical Trial," Press Release. 2018.
Aldeyra Therapeutics, "Aldeyra Therapeutics Announces First Patient Enrolled in Noninfectious Anterior Uveitis Phase 3 Clinical Trial," Press Release. 2017.
Aldeyra Therapeutics, "Aldeyra Therapeutics Announces First Patient Enrolled in Noninfectious Anterior Uveitis Phase II Clinical Trial," Press Release. 2015.
Aldeyra Therapeutics, "Aldeyra Therapeutics Announces First Patient Enrolled in Sjogren-Larsson Syndrome Phase II Clinical Trial," Press Release. 2015.
Aldeyra Therapeutics, "Aldeyra Therapeutics Announces First Patient Enrolled in Sjögren-Larsson Syndrome Pivotal Phase 3 Clinical Trial," Press Release. 2018.
Aldeyra Therapeutics, "Aldeyra Therapeutics Announces Last Patient Dosed in Dry Eye Disease Phase 2a Clinical Trial," Press Release. 2017.
Aldeyra Therapeutics, "Aldeyra Therapeutics Announces Last Patient Dosed in Dry Eye Disease Phase 2b Clinical Trial," Press Release. 2018.
Aldeyra Therapeutics, "Aldeyra Therapeutics Announces Last Patient Dosed in Phase II Trial of NS2 in Patients with Allergic Conjunctivitis," Press Release. 2015.
Aldeyra Therapeutics, "Aldeyra Therapeutics Announces Last Patient Dosed in the ALLEVIATE Phase 3 Clinical Trial," Press Release. 2018.
Aldeyra Therapeutics, "Aldeyra Therapeutics Announces Positive Mesothelioma Investigator-Sponsored Clinical Trial Results Presented at the International Association for the Study of Lung Cancer 19th World Conference on Lung Cancer," Press Release. 2018.
Aldeyra Therapeutics, "Aldeyra Therapeutics Announces Positive Results from Dry Eye Disease Phase 2a Clinical Trial," Press Release. 2017.
Aldeyra Therapeutics, "Aldeyra Therapeutics Announces Positive Results from Phase 2b Dry Eye Disease Clinical Trial," Press Release. 2018.
Aldeyra Therapeutics, "Aldeyra Therapeutics Announces Positive Top-Line Results from the Phase 3 ALLEVIATE Trial in Patients with Allergic Conjunctivitis," Press Release. 2019.
Aldeyra Therapeutics, "Aldeyra Therapeutics Announces Positive Top-Line Symptom and Sign Results from Run-In Cohort of Phase 3 TRANQUILITY Trial in Dry Eye Disease," Jan. 7, 2021.
Aldeyra Therapeutics, "Aldeyra Therapeutics Announces Presentation of Novel Data on the Efficacy of ADX-102 in a Model of Succinic Semialdehyde Dehydrogenase Activity at the 2017 American Society of Human Genetics Annual Meeting," Press Release. 2017.
Aldeyra Therapeutics, "Aldeyra Therapeutics Announces Presentation of Phase 2 Allergic Conjunctivitis Results at the 2016 American College of Allergy, Asthma and Immunology Annual Scientific Meeting," Press Release. 2016.
Aldeyra Therapeutics, "Aldeyra Therapeutics Announces Presentation of Results on the Efficacy of ADX-102 in Noninfectious

(56) References Cited

OTHER PUBLICATIONS

Anterior Uveitis at the American Uveitis Society Held at the American Academy of Ophthalmology 2017 Annual Meeting," Press Release. 2017.
Aldeyra Therapeutics, "Aldeyra Therapeutics Announces Results from Allergic Conjunctivitis Phase 2b Clinical Trial and Plans for Phase 3 Clinical Testing," Press Release. 2017.
Aldeyra Therapeutics, "Aldeyra Therapeutics Announces Third Quarter 2017 Financial Results," Press Release. 2017.
Aldeyra Therapeutics, "Aldeyra Therapeutics Launches the Aldeyra Registry for Patients with Sjögren-Larsson Syndrome," Press Release. 2017.
Aldeyra Therapeutics, "Aldeyra Therapeutics Opens Enrollment in Noninfectious Anterior Uveitis Phase II Clinical Trial," Press Release. 2015.
Aldeyra Therapeutics, "Aldeyra Therapeutics Opens Enrollment in Sjogren-Larsson Syndrome Clinical Trial and Finalizes Noninfectious Anterior Uveitis Clinical Trial Protocol," Press Release. 2015.
Aldeyra Therapeutics, "Aldeyra Therapeutics Presents Dry Eye Disease Phase 2a Clinical Trial Results at the Association for Research in Vision and Ophthalmology 2018 Annual Meeting," Press Release. 2018.
Aldeyra Therapeutics, "Aldeyra Therapeutics Presents Evidence for Aldehyde Sequestration as a Potential Therapeutic Approach in Succinic Semialdehyde Dehydrogenase Deficiency at the American Society of Human Genetics 2017 Annual Meeting, " Press Release. 2017.
Aldeyra Therapeutics, "Aldeyra Therapeutics Presents Noninfectious Anterior Uveitis Phase 2 Clinical Trial Data at the Association for Research in Vision and Ophthalmology 2017 Annual Meeting," Press Release. 2017.
Aldeyra Therapeutics, "Aldeyra Therapeutics Presents Noninfectious Anterior Uveitis Phase 2 Clinical Trial Data to the American Uveitis Society Held at the American Academy of Ophthalmology 2017 Annual Meeting," Press Release. 2017.
Aldeyra Therapeutics, "Aldeyra Therapeutics Provides Update on Late-Stage Clinical Trials at 2016 Research and Development Day," Press Release. 2016.
Aldeyra Therapeutics, "Aldeyra Therapeutics Provides Update on NS2 Clinical Program," Press Release. 2015.
Aldeyra Therapeutics, "Aldeyra Therapeutics Provides Update on Ophthalmic Programs at 2019 Research & Development Day," Press Release. 2019.
Aldeyra Therapeutics, "Aldeyra Therapeutics Reaches Agreement with the US Food and Drug Administration for the Use of RASP as an Objective Sign for the Treatment of Dry Eye Disease," Press Release. 2020.
Aldeyra Therapeutics, "Aldeyra Therapeutics Schedules Conference Call and Webcast to Announce Results from Allergic Conjunctivitis Phase 2b Clinical Trial," Press Release. 2017.
Aldeyra Therapeutics, "Aldeyra Therapeutics Schedules Conference Call to Present Results of a Randomized, Double-Blind, Vehicle-Controlled Clinical Trial in Sjogren-Larsson Syndrome," Press Release. 2016.
Aldeyra Therapeutics, "Aldeyra Therapeutics Schedules Webcast and Conference Call to Announce Results from Dry Eye Disease Phase 2a Clinical Trial," Press Release. 2017.
Aldeyra Therapeutics, "Aldeyra Therapeutics Selected for Podium Presentation of Phase 2a Dry Eye Disease Results at the 2018 Association for Research in Vision and Ophthalmology (ARVO) Annual Meeting," Press Release. 2018.
Aldeyra Therapeutics, "Aldeyra Therapeutics Submits FDA IND Filing for Noninfectious Anterior Uveitis," Press Release. 2014.
Aldeyra Therapeutics, "Aldeyra Therapeutics Submits IND Filing to FDA for Clinical Testing of NS2 in Patients With Sjogren-Larsson Syndrome," Press Release. 2015.
Aldeyra Therapeutics, "Aldeyra Therapeutics to Host 2019 Research & Development Day," Press Release. 2019.
Aldeyra Therapeutics, "Aldeyra Therapeutics to Present at the 2016 SSADH Symposium," Press Release. 2016.
Aldeyra Therapeutics, "Aldeyra Therapeutics to Present Novel Data on a Potential Treatment for Sjogren-Larsson Syndrome at the 2015 Society for Inherited Metabolic Disorders Annual Meeting," Press Release. 2015.
Aldeyra Therapeutics, "Aldeyra Therapeutics to Present Novel Data on a Potential Treatment for Succinic Semi-Aldehyde Dehydrogenase Deficiency at the 2015 American Society of Human Genetics (ASHG) Annual Meeting," Press Release. 2015.
Aldeyra Therapeutics, "Aldeyra Therapeutics' Data on Lead Candidate NS2 to be Presented at Society for Investigative Dermatology 2014 Annual Meeting," Press Release. 2014.
Aldeyra Therapeutics, "Aldeyra Therapeutics, Inc. Announces Last Patient Dosed in Allergic Conjunctivitis Phase 2b Clinical Trial," Press Release. 2017.
Aldeyra Therapeutics, "Aldeyra Therapeutics, Inc. Announces Last Patient Dosed in Phase II Clinical Trial of Topical Dermatologic NS2 in Patients With Sjogren-Larsson Syndrome," Press Release. 2016.
Aldeyra Therapeutics, "Aldeyra Therapeutics, Inc. Receives Orphan Drug Designation from the U.S. Food and Drug Administration for ADX-102 in Sjögren-Larsson Syndrome," Press Release. 2017.
Aldeyra Therapeutics, "Phase II Allergic Conjunctivitis, " Press Release. 2016.
Aldeyra Therapeutics, "Positive Results From Phase II Clinical Trial in Subjects With Noninfectious Anterior Uveitis," Press Release. 2016.
Aldeyra Therapeutics, Inc., "A Randomized, Double Masked, Clinical Study of Subjects with Dry Eye Syndrome," ClinicalTrials.gov identifier NCT03162783. First Posted May 22, 2017; https://clinicaltrials.gov/ct2/show/NCT03162783.
Aldeyra Therapeutics, Inc., "A Safety and Activity Study of NS2 in Subjects with Allergic Conjunctivitis," ClinicalTrials.gov identifier NCT02578914. First Posted Oct. 19, 2015; https://clinicaltrials.gov/ct2/show/NCT02578914.
Aldeyra Therapeutics, Inc., "A Safety and Efficacy Study of NS2 in Patients with Anterior Uveitis," ClinicalTrials.gov identifier NCT02406209. First Posted Apr. 2, 2015; https://clinicaltrials.gov/ct2/show/NCT02406209.
Aldeyra Therapeutics, Inc., "A Study of Topical NS2 Cream to Treat Ichthyosis in Sjogren-Larsson Syndrome (SLS)," ClinicalTrials.gov Identifier NCT02402309. First Posted Mar. 30, 2015; https://clinicaltrials.gov/ct2/show/NCT02402309.
Zhou et al., "Mechanisms for the induction of HNE- MDA- and AGE-adducts, RAGE and VEGF in retinal pigment epithelial cells," Exp Eye Res., 80(4):567-80 (2005).
Aldini et al., "Lipoxidation-derived reactive carbonyl species as potential drug targets in preventing protein carbonylation and related cellular dysfunction," ChemMedChem. 2006; 1(10):1045-58.
Aldini et al., "The carbonyl scavenger carnosine ameliorates dyslipidemia and renal function in Zucker obese rats," J Cell Mol Med. 2011;15(6):1339-54.
Allergan, "Restasis® Prescribing Information," copyright 2016, revised 2017.
Amara et al., "Autoantibodies to malondialdehyde-modified epitope in connective tissue diseases and vasculitides," Clin Exp Immunol. 1995;101(2):233-8.
Ao et al., "Methyl-(beta)-Cyclodextrin Impairs the Monocyte-Adhering Ability of Endothelial Cells by Down-Regulating Adhesion Molecules and Caveolae and Reorganizing the Actin Cytoskeleton," Biol Pharm Bull. 2016;39(6):1029-34.
Apparsundaram et al., "Molecular cloning of a human, hemicholinium-3-sensitive choline transporter," Biochem Biophys Res Commun. 2000;276(3):862-7.
Ardati et al., "Interaction of [3H]orphanin FQ and 125I-Tyr14-orphanin FQ with the orphanin FQ receptor: kinetics and modulation by cations and guanine nucleotides," Mol Pharmacol. 1997;51(5):816-24.
Ashton et al., "Location of penetration and metabolic barriers to levobunolol in the corneal epithelium of the pigmented rabbit," J Pharmacol Exp Ther. 1991;259(2):719-24.

(56) References Cited

OTHER PUBLICATIONS

Atkinson et al., "Triazaphenanthrenes. Part VI.* Further Observations on the Widman-Stoermer and Brosche Reactions," J Chem Soc C. 1966;2053-60.
Augustin et al., "Oxidative reactions in the tear fluid of patients suffering from dry eyes," Graefes Arch Clin Exp Ophthalmol. 1995;233(11):694-8.
Axelsson et al., "Experimental colitis induced by dextran sulphate sodium in mice: beneficial effects of sulphasalazine and olsalazine," Aliment Pharmacol Ther. 1998; 12(9):925-34.
Bachman and Welton, "Quinoline derivatives from 3-nitro-4-hydroxyquinoline," J Am Chem Soc. 1947;69(2):365-71.
Bacsi et al., "Effect of pollen-mediated oxidative stress on immediate hypersensitivity reactions and late-phase inflammation in allergic conjunctivitis," J Allergy Clin Immunol. 2005;116(4):836-43.
Badii, "Allergic Conjunctivitis," Healthline. 2016; Retrieved 2019: https://www.healthline.com/health/allergic-conjunctivitis.
Balci et al., "Effects of computer monitor-emitted radiation on oxidant/antioxidant balance in cornea and lens from rats," Mol Vis. 2009;15:2521-5.
Balci et al., "Investigation of oxidative stress in pterygium tissue," Mol Vis. 2011; 17:443-447.
Ballard et al., "Effects of sildenafil on the relaxation of human corpus cavernosum tissue in vitro and on the activities of cyclic nucleotide phosphodiesterase isozymes," J Urol. 1998; 159(6):2164-71.
Baltatzis et al., "Mycophenolate mofetil as an immunomodulatory agent in the treatment of chronic ocular inflammatory disorders," Ophthalmology. 2003;110(5):1061-5.
Bardwell et al., "Docking sites on mitogen-activated protein kinase (MAPK) kinases, MAPK phosphatases and the Elk-1 transcription factor compete for MAPK binding and are crucial for enzymic activity," Biochem J. 2003;370(Pt 3):1077-1085.
Baron et al., "[3H]MDL 105,519, a high-affinity radioligand for the N-methyl-D-aspartate receptor-associated glycine recognition site," J Pharmacol Exp Ther. 1996;279(1):62-8.
Bartoli et al., "Malondialdehyde in exhaled breath condensate as a marker of oxidative stress in different pulmonary diseases," Mediators Inflamm. 2011;2011:891752.
Bastin et al., "Salt Selection and Optimisation Procedures for Pharmaceutical New Chemical Entities," Org Proc Res Dev. 2000;4(5):427-35.
Batista et al., "Age-dependent changes in rat lacrimal gland antioxidant and vesicular related protein expression profiles," Mol Vis. 2012; 18:194-202.
Batista et al., "Short-term treatment with bisphenol-A leads to metabolic abnormalities in adult male mice," PLoS One. 2012;7(3):e33814.
Baum et al., "Omega 3 fatty acid inhibition of inflammatory cytokine-mediated Connexin43 regulation in the heart," Front Physiol. 2012;3:272.
Baz et al., "Plasma reactive oxygen species activity and antioxidant potential levels in rosacea patients: correlation with seropositivity to Helicobacter pylori," Int J Dermatol. 2004;43(7):494-7.
Berge et al., "Pharmaceutical salts," J Pharm Sci. 1977; 66(1); 1-19.
Berkhout et al., "Cloning, in vitro expression, and functional characterization of a novel human CC chemokine of the monocyte chemotactic protein (MCP) family (MCP-4) that binds and signals through the CC chemokine receptor 2B," J Biol Chem. 1997;272(26):16404-13.
Bermudez and Grau, "Thermosensitive poloxamer-based injectables as controlled drug release platforms for veterinary use: Development and in-vitro evaluation," Int Res J Pharm Pharmacol. 2011;1(6):109-118.
Bernstein and Rando, "The specific inhibition of 11-cis-retinyl palmitate formation in the frog eye by diaminophenoxypentane, an inhibitor of rhodopsin regeneration," Vision Res. 1985;25(6):741-8.
Bernstein et al., "Mechanism of action of aromatic amines that short-circuit the visual cycle," Biochemistry. 1986;25(11):3370-7.
Bernstein et al., "Retinal toxicity associated with occupational exposure to the fish anesthetic MS-222," Am J Ophthalmol. 1997;124(6):843-4.
Bernstein et al., "Short-circuiting the visual cycle with retinotoxic aromatic amines," Proc Natl Acad Sci U S A. 1986;83(6):1632-5.
Bickett et al., "A high throughput fluorogenic substrate for interstitial collagenase (MMP-1) and gelatinase (MMP-9)," Anal Biochem. 1993;212(1):58-64.
Bignon et al., "SR146131: a new potent, orally active, and selective nonpeptide cholecystokinin subtype 1 receptor agonist. I. In vitro studies," J Pharmacol Exp Ther. 1999;289(2):742-51.
Blindauer et al., "A randomized controlled trial of etilevodopa in patients with Parkinson disease who have motor fluctuations," Arch Neurol. 2006;63(2):210-6.
Boldogh et al., "ROS generated by pollen NADPH oxidase provide a signal that augments antigen-induced allergic airway inflammation," J Clin Invest. 2005;115(8):2169-79.
Boner et al., "Bronchodilating activity of oral clenbuterol in asthmatic children after single administration of different dosages," Pediatr Pulmonol. 1987;3(1):34-7.
Bousquet et al., "How to design and evaluate randomized controlled trials in immunotherapy for allergic rhinitis: an ARIA-GA(2) Len statement," Allergy. 2011;66(6):765-74.
Boyer et al., "Lipofuscin and N-retinylidene-N-retinylethanolamine (A2E) accumulate in retinal pigment epithelium in absence of light exposure: their origin is 11-cis-retinal," J Biol Chem. 2012;287(26):22276-86.
Bozkir et al., "Effect of hydroxypropyl-beta-cyclodextrin on the solubility, stability and in-vitro release of ciprofloxacin for ocular drug delivery," Acta Pol Pharm. 2012;69(4):719-24.
Bragagni et al., "Cyclodextrin complexation highly enhances efficacy of arylsulfonylureido benzenesulfonamide carbonic anhydrase inhibitors as a topical antiglaucoma agents," Bioorg Med Chem. 2015;23(18):6223-7.
Brandt et al., "The Prevalence of Non-Alcoholic Fatty Liver Disease in Patients With Inflammatory Bowel Disease," American Journal of Gastroenterology 2017;112:S542, S544.
Brenneman et al., "Cannabidiol Provides Protection from Ethanol and Ammonium toxicity in a Hippocampal Model of Hepatic Encephalopathy," 24th Annual Symposium of the International Cannabinoid Research Society, Baveno, Italy. 2014;73.
Brenneman et al., "Small molecule anticonvulsant agents with potent in vitro neuroprotection," J Mol Neurosci. 2012;47(2):368-79.
Brewitt and Sistani, "Dry eye disease: the scale of the problem," Surv Ophthalmol. 2001;45 Suppl 2:S199-202.
BRIDION® (sugammadex) Injection, for intravenous use, Highlights of Prescribing Information. 2015.
Brockhaus et al., "Identification of two types of tumor necrosis factor receptors on human cell lines by monoclonal antibodies," Proc Natl Acad Sci U S A. 1990;87(8):3127-31.
Brown, "3H-batrachotoxinin-A benzoate binding to voltage-sensitive sodium channels: inhibition by the channel blockers tetrodotoxin and saxitoxin," J Neurosci. 1986;6(7):2064-70.
Brozek et al., "Grading quality of evidence and strength of recommendations in clinical practice guidelines: Part 2 of 3. The GRADE approach to grading quality of evidence about diagnostic tests and strategies," Allergy. 2009;64(8):1109-16.
Bryant et al., "A novel class of 5-HT2A receptor antagonists: aryl aminoguanidines," Life Sci. 1996;59(15):1259-68.
Bucciantini et al., "Inherent toxicity of aggregates implies a common mechanism for protein misfolding diseases," Nature. 2002;416(6880):507-11.
Buchan et al., "Characterization of three non-peptide endothelin receptor ligands using human cloned ETA and ETB receptors," Br J Pharmacol. 1994; 112(4):1251-7.
Buddi et al., "Evidence of oxidative stress in human corneal diseases," J Histochem Cytochem. 2002;50(3):341-51.
Bundgaard, "(C) Means to Enhance Penetration: (1) Prodrugs as a means to improve the delivery of peptide drugs," Adv Drug Deliv Rev. 1992;8:1-38.

(56) References Cited

OTHER PUBLICATIONS

Burcham et al., "Aldehyde-sequestering drugs: tools for studying protein damage by lipid peroxidation products," Toxicology. 2002; 181-182:229-36.
Burstein, "Preservative cytotoxic threshold for benzalkonium chloride and chlorhexidine digluconate in cat and rabbit corneas," Invest Ophthalmol Vis Sci. 1980;19(3):308-13.
Burstein, "The effects of topical drugs and preservatives on the tears and corneal epithelium in dry eye," Trans Ophthalmol Soc U K (1962). 1985;104(Pt 4):402-9.
Canonica et al., "Recommendations for standardization of clinical trials with Allergen Specific Immunotherapy for respiratory allergy. A statement of a World Allergy Organization (WAO) taskforce," Allergy. 2007;62(3):317-24.
Canonica et al., "Sub-lingual immunotherapy: World Allergy Organization Position Paper 2009," Allergy. 2009;64 Suppl 91:1-59.
Casanaro et al., "A convenient solvent system for cellulose dissolution and derivatization: Mechanistic aspects of the acylation of the biopolymer in tetraallylammonium fluoride/dimethyl sulfoxide," Carbohydr Polym. 2011;8(3):1395-402.
Casanaro et al., "Efficacy of vigabatrin intervention in a mild phenotypic expression of succinic semialdehyde dehydrogenase deficiency," JIMD Rep. 2012;2:119-23.
Cejková et al., "The role of conjunctival epithelial cell xanthine oxidoreductase/xanthine oxidase in oxidative reactions on the ocular surface of dry eye patients with Sjögren's syndrome," Histol Histopathol. 2007;22(9):997-1003.
Cesura et al., "Characterization of the binding of [3H]Ro 41-1049 to the active site of human monoamine oxidase-A," Mol Pharmacol. 1990;37(3):358-66.
Chao et al., "Co-existence of non-alcoholic fatty liver disease and inflammatory bowel disease: A review article," World J Gastroenterol. 2016;22(34): 7727-7734.
Chapple et al., "Unfolding retinal dystrophies: a role for molecular chaperones?" Trends Mol Med. 2001;7(9):414-21.
Chen et al., "Methazolamide Calcium Phosphate Nanoparticles in an Ocular Delivery System," Pharm Soc Japan, 2010; 130(3):419-24.
Cheng et al., "A synthetic peptide derived from p34cdc2 is a specific and efficient substrate of src-family tyrosine kinases," J Biol Chem. May 5, 1992;267(13):9248-56.
Chiarpotto et al., "Role of 4-hydroxy-2,3-nonenal in the pathogenesis of fibrosis," Biofactors. 2005;24(1-4):229-36.
Chicchi et al., "Alterations in receptor activation and divalent cation activation of agonist binding by deletion of intracellular domains of the glucagon receptor," J Biol Chem. 1997;272(12):7765-9.
Choi et al., "Expression of Lipid Peroxidation Markers in the Tear Film and Ocular Surface of Patients with Non-Sjogren Syndrome: Potential Biomarkers for Dry Eye Disease," Curr Eye Res. 2016;41(9):1143-9.
Choi et al., "The human serotonin 5-HT2B receptor: pharmacological link between 5-HT2 and 5-HT1D receptors," FEBS Lett. 1994;352(3):393-9.
Ciolino et al., "Effect of alcaftadine 0.25% on ocular itch associated with seasonal or perennial allergic conjunctivitis: a pooled analysis of two multicenter randomized clinical trials," Clin Ophthalmol. 2015;9:765-72.
Clark et al., "Inhibition of dexamethasone-induced cytoskeletal changes in cultured human trabecular meshwork cells by tetrahydrocortisol," Invest Ophthalmol Vis Sci. 1996;37(5):805-13.
Clinical Trials Results for Outcome Measures of Ocular Itching and Ocular Tearing (1 page) (2016).
Clinical Trials Results of Treatment with Aldehyde Trapping Compound NS2 (1 page) (2015).
Clinical Trials Results of Treatment with NS2 Topical Formulation (1 page) (2015).
Conover et al., "Thiazole Analogs of Pyridoxine," Journal of the American Chemical Society, 72(11):5221-5225 (1950).
Cooper et al., "Clinicopathologic study of dextran sulfate sodium experimental murine colitis," Lab Invest, 69(2):238-49 (Aug. 1993).
Couvineau et al., "Molecular identification and structural requirement of vasoactive intestinal peptide (VIP) receptors in the human colon adenocarcinoma cell line, HT-29," Biochem. J., 231:139-143 (1985).
Cullen et al., "Administration of the small molecule aldehyde trap NS2 in a hamster model of radiation-induced oral mucositis," ISOO 2015 Annual Meeting Abstract, Support Care Cancer, 23 (Suppl 1):S107 (Jun. 2015).
Cullen et al., "The small molecule aldehyde trap NS2 exhibits potent anti-inflammatory activity in three murine models of inflammation," AAAAI Annual Meeting Abstract, 1 page (Feb. 2015).
Davies, "Biopharmaceutical considerations in topical ocular drug delivery," Clin Exp Pharmacol Physiol, 2000; 27(7):558-62.
De Jong, "Age-Related Macular Degeneration," N Engl J Med, 355(14):1474-1485 (2006).
Del Valle, "Cyclodextrins and their uses: a review," Process Biochemistry, 2004; 39(9):1033-1046.
Demir et al., "Oxidative stress of intracameral lidocaine and levobupivacaine on ocular tissues," Br J Ophthalmol, 2010; 94(8):1083-7.
Demir et al., "The protective effect of alpha-lipoic acid against oxidative damage in rabbit conjunctiva and cornea exposed to ultraviolet radiation," Ophthalmologica, 2005; 219(1):49-53.
Dente et al., "Modified phage peptide libraries as a tool to study specificity of phosphorylation and recognition of tyrosine containing peptides," J. Mol. Biol., 269:694-703 (1997).
Devedjian et al., "Further characterization of human alpha 2-adrenoceptor subtypes: [31-1]RX821002 binding and definition of additional selective drugs," Eur. J. Pharmacol., 252:43-49 (1994).
Devillier et al., "The allergen challenge chamber: A valuable tool for optimizing the clinical development of pollen immunotherapy," Allergy, 2011; 66(2):163-9.
Division of AIDS, National Institute of Allergy and Infectious Diseases, National Institutes of Health, US Department of Health and Human Services, Division of AIDS (DAIDS) Table for Grading the Severity of Adult and Pediatric Adverse Events, V2.0, 33 pages. (Nov. 2014).
Dolmotova et al., "Cardiomyocyte ATP release through pannexin 1 aids in early fibroblast activation," Am. J. Physiol Heart Circ Physiol 303(10):H1208-1218 (2012).
Dorje et al., "Antagonist binding profiles of five cloned human muscarinic receptor subtypes," J. Pharmacol. Exp. Ther., 256:727-733 (1991).
Dowling, "Neural and Photochemical Mechanisms of Visual Adaptation in the Rat," Journal of General Physiology, 46(6):1287-1291 (1963).
Drysdale et al., "Complex Promoter and Coding Region Beta 2-adrenergic Receptor Haplotypes Alter Receptor Expression and Predict in vivo Responsiveness," Proc Natl Acad Sci USA, 97(19):10483-10488 (2000).
Egger, et al., "Keratinocyte growth factor ameliorates dextran sodium sulfate colitis in mice," Dig Dis Sci, 44(4): 836-44 (Apr. 1999).
Ellis et al., "Multiple Doses of Trodusquemine Improve Glucose Tolerance in Type 2 Diabetic Subjects," 69th Scientific Sessions of the American Diabetes Association, Abstract No. 2071-PO (2009).
Ellman et al., "A new and rapid colorimetric determination of acetylcholinesterase activity," Biochem. Pharmacol., 7: 88-95 (1961).
Erdos et al, "Neutral endopeptidase 24.11 (enkephalinase) and related regulators of peptide hormones," FASEB J. 3:145 (1989).
Ermolieff et al., "Proteolytic activation of recombinant pro-memapsin 2 (pro-beta-secretase) studied with new fluorogenic substrates," Biochemistry, 39:12450-12456 (2000).
Escalera et al., "Succinic semialdehyde dehydrogenase deficiency: decrease in 4-OH-butyric acid levels with low doses of vigabatrin," An Pediatr (Barc). 72(2):128-32 (2010).
Esterbauer et al., "Chemistry and Biochemistry of 4-Hydroxynonenal, Malonaldehyde and Related Aldehydes," Free Radic Biol Med, 1991; 11:81-128.
Everest-Todd, "Topical Application of Cyclodextrin Ethers in the Control of Pain," Proceedings of the Eighth International Symposium on Cyclodextrins, pp. 495-498 (1998).

(56) References Cited

OTHER PUBLICATIONS

Farid et al., "Detection of corneal fibrosis by imaging second harmonic-generated signals in rabbit corneas treated with mitomycin C after excimer laser surface ablation," Invest Ophthalmol Vis Sci. 2008;49(10):4377-83.
FDA, "Bam R59: Phosphate-Buffered Saline (PBS), pH 7.4," Jan. 2001, retrieved online at <http://www.fda.gov/Food/FoodScienceR.esearch/LaboratoxyMethods/ucm062268.htm> on Apr. 18, 2015 (1 page).
Feighner et al., "Receptor for motilin identified in the human gastrointestinal system," Science, 284:2184-2188 (1999).
Fernandes et al., "Characterization of angiotensin-converting enzymes 1 and 2 in the soleus and plantaris muscles of rats," Braz J Med Biol Res., 43:837-842 (2010).
Ferry et al., "Binding of prostaglandins to human PPAR ?: Tool assessment and new natural ligands," Eur. J. Pharmacol., 417:77-89 (2001).
Feve et al., "Transcriptional down-regulation by insulin of the beta 3-adrenergic receptor expression in 3T3-F442A adipocytes: a mechanism for repressing the CAMP signaling pathway," Proc Natl Acad Sci USA. 91:5677 (1994).
Fiske et al., "The Colormetric Determination of Phosphorus," J. Biol. Chem., 66:375-400 (1925).
Fitzmaurice et al., "Aldehyde dehydrogenase inhibition as a pathogenic mechanism in Parkinson disease," Proc. Natl Acad Sci U.S.A, 110(2):636-641 (2013).
Ford et al., "Pharmacological pleiotropism of the human recombinant alpha1A-adrenoceptor: implications for alpha1-adrenoceptor classification," Brit. J. Pharmacol., 121:1127-1135 (1997).
Fowler et al., "Coloured Complexes of all-trans-retinal with Benzocaine and Other Local Anesthetics," J Photochem Photobiol B, 8(2):183-188 (1991).
Frantz et al., "The Activation State of p38 Mitogen-Activated Protein Kinase Determines the Efficiency of ATP Competition for Pyridinylimidazole Inhibitor Binding," Biochemistry, 37:13846-13853 (1998).
Friesen et al., "Optimization of a Tertiary Alcohol Series of Phosphodiesterase-4 (PDE4) Inhibitors: Structure-Activity Relationship Related to PDE4 Inhibition and Human Ether-a-go-go Related Gene Potassium Channel Binding Affinity," J. Med. Chem., 46(12):2413-2426 (2003).
Fuchs et al., "Functional characterization of three mutations of the endothelin B receptor gene in patients with Hirschsprung's disease: evidence for selective loss of Gi coupling," Mol. Med., 7:115-124 (2001).
Fukunaga et al., "Single nucleotide polymorphism of human platelet-activating factor receptor impairs G-protein activation," J. Biol. Chem., 276:43025-43030 (2001).
Full 1H NMR assignment for RAL-NS2 in CDCIJ, submitted to Japanese Patent Office Mar. 1, 2012.
Ganapathy et al., "Molecular and ligand-binding characterization of the sigma-receptor in the Jurkat human T lymphocyte cell line," JPET, 289:251-260 (1999).
Gasper et al., "2-Hydroxypropyl-beta-cyclodextrin (HPβCD) reduces age-related lipofuscin accumulation through a cholesterol-associated pathway," Scientific Reports, 2017; 7(2197):1-7.
Gibson et al., "Stable isotope dilution analysis of 4-hydroxybutyric acid: an accurate method for quantification in physiological fluids and the prenatal diagnosis of 4-hydroxybutyric aciduria," Biomed Environ Mass Spectrom., 19(2):89-93 (1990).
Gibson et al., "Stable-isotope dilution analysis of D- and L-2-hydroxyglutaric acid: application to the detection and prenatal diagnosis of D- and L-2-hydroxyglutaric acidemias," Pediatr Res., 34(3):277-80 (1993).
Gibson et al., "The Aldehyde Trap NS2 Mitigates Dense Haze in a Rabbit Model of Photorefractive Keratectomy" ARVO Annual Meeting Abstract, 1 page (Jun. 2015).
Godard et al., "Sur les orthoamino formyl quinoleines, nouveaux synthons heterocycliques," J Heterocyclic Chem, 17(3):465-473 (1980).

Goldstein et al., "A Phase 2 Exploratory Study of a Novel Interleukin-1 Receptor Inhibitor (EBI-005) in the Treatment of Moderate-to-Severe Allergic Conjunctivitis," Eye Contact Lens, 2015; 41(3):145-55.
Gole et al., "Plasma Proteins Modified by Tyrosine Nitration in Acute Respiratory Distress Syndrome," Am J Physiol Lung Cell Mol Physiol, 2000, vol. 278, pp. L961-L967.
Gomez, "Dimethyltin(IV) 2,6-disubstituted pyridine complexes," J. Organometallic Chemistry, 672(2):115-122 (2003).
Good, "Measuring field loss in children administered vigabatrin: a problem in search of a solution," J AAPOS. 15(5):411-2 (2011).
Gopalakrishnan et al., "Stable expression, pharmacologic properties and regulation of the human neuronal nicotinic acetylcholine alpha 4 beta 2 receptor," J. Pharmacol. Exp. Ther., 276:289-297 (1996).
Gould et al., "[3H]nitrendipine-labeled calcium channels discriminate inorganic calcium agonists and antagonists," Proc. Natl. Acad. Sci. U.S.A., 79:3656-3660 (1982).
Grandy et al., "Cloning of the cDNA and gene for a human D2 dopamine receptor," Proc. Natl. Acad. Sci. U.S.A., 86:9762-9766 (1989).
Green et al., "Characterization of [(3)H]-CGP54626A binding to heterodimeric GABA(B) receptors stably expressed in mammalian cells," Brit. J. Pharmacol., 131:1766-1774 (2000).
Green et al., "Influence of Various Agents on Corneal Permeability," American Journal of Ophthalmology, 1971; 72(5):897-905.
Grob et al., "Die Synthese von 5-Oxy-benz(cd)indolin and dessen Umpagerung in 5-Keto-1,3,4,5-tetrahydro-benz(cd)indol," Helvetica Chimica Acta, Verlag Helvetica Chimica Acta, CH, 33(6):1796-1808 (1950).
Gromachevskaya et al., "4H-3,1-benzoxazines. 2. Synthesis of 2,4-substituted 1 2-dihydro-4H-3,1-benzoxazines," Chemistry of Heterocyclic Compounds, 24(6):692-697 (Jun. 1988).
Grotto et al., "Importance of the lipid peroxidation biomarkers and methodological aspects for malondialdehyde quantification," Quim Nova, 2009; 32(1):169-174.
Halilovic et al., "ADX-103, a Novel Small Molecule Aldehyde Sequestering Agent, Decreases Retinal Edema and Inflammation in a Rat Model of Diabetic Macular Edema," ARVO Annual Meeting Abstract, 2 pages (Jul. 2018).
Hampson et al., "Cannabidiol and (−)Delta9-tetrahydrocannabinol are neuroprotective antioxidants," Proc. Nat. Acad. Sci 95:8268-8273 (1998).
Hassan et al., "Oxidative stress in systemic lupus erythematosus and rheumatoid arthritis patients: relationship to disease manifestations and activity," International Journal of Rheumatic Diseases, 14(1):325-331 (2011).
Herbort et al., "Endotoxin-induced uveitis in the rat," Graefe's Arch Clin Exp Ophthalmol, 1988; 226:553-8.
Hessen et al., "Dry Eye: an Inflammatory Ocular Disease," J Ophthalmic Vis Res, 2014; 9(2):240-250.
Heuillet et al., "Characterization of a Human NK1 Tachykinin Receptor in the Astrocytoma Cell Line U 373 MG," J. Neurochem., 60:868-876 (1993).
Highlights of Prescribing Information, Bridion® (sugammadex) Injection, for intravenous use, Initial U.S. Approval: 2015, Last Revised Dec. 2015 (19 pages).
Hogema et al., "Pharmacologic rescue of lethal seizures in mice deficient in succinate semialdehyde dehydrogenase," Nat Genet. 29:212-16 (2001).
Hom et al., "Allergic conjunctivitis and dry eye syndrome," Ann Allergy Asthma Immunol, 2012; 108(3):163-6.
Hong et al., "Laboratory Scale Production of Injectable Liposomes By Using Cell Disruptor . . . ," Journal of Pharmaceutical Investigation, 2015, vol. 45, pp. 73-78.
Hope et al., "Characterization of a human 5-hydroxytryptamine3 receptor type A (h5-HT3R-AS) subunit stably expressed in HEK 293 cells," Brit. J. Pharmacol., 118:1237-1245 (1996).
Horner et al., "Analogs of 3-Amino-7-chloro-1,2,4-benzotriazine 1-Oxide as Antimalarial Agents," J. Med. Chem., 11(5):946-949 (1968).
Hoyer et al., "Characterization of the 5-HT1B recognition site in rat brain: binding studies with (−)[125I]iodocyanopindolol," Eur. J. Pharmacol., 118:1-12 (1985).

(56) References Cited

OTHER PUBLICATIONS

Huang et al., "Characterization of Calcium Phosphate Nanoparticles Based on a PEGylated Chelator for Gene Delivery," ACS Appl Mater Interfaces, 9:10435?10445 (Mar. 2017).
Huang et al., "Identification of human Ether-a-go-go related gene modulators by three screening platforms in an academic drug-discovery setting," Assay Drug Dev Technol., 8(6):727-42 (2010).
Huang et al., "Novel peptide inhibitors of angiotensin-converting enzyme 2," J. Biol. Chem., 278:15532-15540 (2003).
Hubbard, "Geometrical Isomerization of Vitamin A, Retinene and Retinene Oxime," Journal of the American Chemical Society, 78(18):4662-4667 (1956).
Hugues et al., "Preparation of a pure monoiodo derivative of the bee venom neurotoxin apamin and its binding properties to rat brain synaptosomes," J. Biol. Chem., 257:2762-2769 (1982).
Hurd et al., "Reaction of Propiolactone with Aniline Derivatives," Journal of the American Chemical Society, 74(23):5889-5893 (1952).
Inoue et al., "Filter-binding assay procedure for thyroid hormone receptors," Anal Biochem. 134(1):176 (1983).
Iriyama et al., "A2E, a pigment of the lipofuscin of retinal pigment epithelial cells, is an endogenous ligand for retinoic acid receptor," J Biol Chem., 283(18):11947-53 (2008) Epub Mar. 6, 2008.
Irons, "Fluvoxamine in the treatment of anxiety disorders," Neuropsychiatr Dis Treat. 2005;1(4):289-99.
Ishida et al., "Stabilization of calmodulin-dependent protein kinase II through the autoinhibitory domain," J. Biol. Chem., 270:2163-2170 (1995).
Ito et al., "A Medium-Term Rat Liver Bioassay for Rapid in vivo Detection of Carcinogenic Potential of Chemicals," Cancer Science, 94(1):3-8 (2003).
Itokawa et al., "Antiangiogenic effect by SU5416 is partly attributable to inhibition of Flt-1 receptor signaling," Mol. Cancer Ther., 1:295-302 (2002).
Jacobs et al., "Responses to ragweed pollen in a pollen challenge chamber versus seasonal exposure identify allergic rhinoconjunctivitis endotypes," J. Allergy Clin. Immunol., 2012; 130(1):122-7.
Jafari et al., "Evaluation of plasma, erythrocytes, and bronchoalveolar lavage fluid antioxidant defense system in sulfur mustard-injured patients," Clin Toxicol (Phila)., 48(3):184-92 (2010).
Janowski et al., "Structural requirements of ligands for the oxysterol liver X receptors LXRalpha and LXRbeta," Proc. Natl. Acad. Sci. USA, 96:266-271 (1999).
Jarrett et al., "Mitochondrial DNA damage and impaired base excision repair during epileptogenesis," Neurobiology of Disease, 30(1):130-138 (2008).
Jellinger et al., "American Association of Clinical Endocrinologists and American College of Endocrinology Guidelines for Management of Dyslipidemia and Prevention of Cardiovascular Disease," Endocr Pract. 2017;23(Suppl 2):1-87.
Ji et al., "Exploration of diverse hinge-binding scaffolds for selective Aurora kinase inhibitors," Bioorg. & Med. Chem. Let. 22:4528 (2012).
Johannsdottir et al., "Development of a Cyclodextrin-Based Aqueous Cyclosporin A Eye Drop Formulations," International Journal of Pharmaceutics, 2015; 493(1-2):86-95.
Johnson et al., "2-Hydroxypropyl-β-Cyclodextrin Removes All-Trans Retinol from Frog Rod Photoreceptors in a Concentration-Dependent Manner," Journal of Ocular Pharmacology and Therapeutics, 2010; 26(3):245-248.
Joseph et al., "Binding of (−)-[3H]-CGP12177 at two sites in recombinant human beta 1-adrenoceptors and interaction with beta-blockers," Naun.-Sch. Arch. Pharm., 369:525-532 (2004).
Kam et al., "Topical Cyclodextrin Reduces Amyloid Beta and Inflammation Improving Retinal Function in Ageing Mice," Experimental Eye Research, 2015; 135:59-66.
Kamino et al., "Deficiency in mitochondrial aldehyde dehydrogenase increases the risk for late-onset Alzheimer's disease in the Japanese population," Biochemical and Biophysical Research Communications, 273(1):192-196 (2000).
Karahashi et al., "Changes of caspase activities involved in apoptosis of a macrophage-like cell line J774.1/JA-4 treated with lipopolysaccharide (LPS) and cycloheximide," Biol. Pharm. Bull., 23:140-144 (2000).
Karan et al., Lipofuscin Accumulation, Abnormal Electrophysiology, and Photoreceptor Degeneration in Mutant ELOVL4 Transgenic Mice: A Model for Macular Degeneration, Proc Natl Acad Sci USA, 102(11):4164-4169 (2005).
Katugampola et al., "[(125)I]-(Pyr(1))Apelin-13 is a novel radioligand for localizing the APJ orphan receptor in human and rat tissues with evidence for a vasoconstrictor role in man," Brit. J. Pharmacol., 132:1255-1260 (2001).
Keister et al., "Inflammatory Bowel Disease and Irritable Bowel Syndrome Similarities and Differences," Crohn's & Colitis Foundation of America 2014.
Kenney et al., "The Cascade Hypothesis of Keratoconus," Contact Lens & Ant Eye, 26:139-146 (2003).
Keri, "Rosacea," Merck Manual, Professional Version, https://www.merckmanuals.com/professional/dermatologic-disorders/acne-and-related-disorders/rosacea, 7 pages (2017).
Knapp et al., "Intraocular Availability of Topically Applied Mycophenolate Mofetil in Rabbits," J. Ocul. Pharmacol. Ther., 2003; 19(2):181-192.
La Rosa et al., "Allergic conjunctivitis: a comprehensive review of the literature," Ital J Pediatr, 2013; 39:18.
Landor et al., "Allenes. Part 49, 4-Amino-2-(1-hydroxyalkyl)quinolones from Phenylhydroxylamine and Allenic Nitrites," J Chem Soc Perkin Trans 1, pp. 251-254 (1989).
Langin et al., "[3H]RX821002: a new tool for the identification of alpha 2A-adrenoceptors," Eur. J. Pharmacol., 167: 95-104 (1989).
Lankin et al., "Role of Oxidative Stress in the Genesis of Atherosclerosis and Diabetes Mellitus: A Personal Look Back on 50 Years of Research," Curr. Aging Sci. 10:18 (2017).
Le et al., "Ligand binding and functional properties of human angiotensin AT1 receptors in transiently and stably expressed CHO-K1 cells," Eur. J. Pharmacol., 513:35-45 (2005).
Lee et al., "Human recombinant soluble guanylyl cyclase: expression, purification, and regulation," Proc. Natl. Acad. Sci. USA, 97(20):10763-10768 (2000).
Lee et al., "The human brain cholecystokinin-B/gastrin receptor. Cloning and characterization," J. Biol. Chem., 268: 8164-8169 (1993).
Leibundgut et al., "Oxidation-specific epitopes and immunological responses: Translational biotheranostic implications for atherosclerosis," Current Opinion in Pharmacology, 13(2):168-179 (2013).
Leonardi et al., "Correlation Between Conjunctival Provocation Test (CPT) and Systemic Allergometric Tests in Allergic Conjunctivitis," Eye, 1990; 4:760-764.
Leonardi, "Allergy and allergic mediators in tears," Exp. Eye Res., 2013; 117:106-17.
Leurs et al., "Pharmacological characterization of the human histamine H2 receptor stably expressed in Chinese hamster ovary cells," Brit. J. Pharmacol., 112: 847-854 (1994).
Levey et al., "A new equation to estimate glomerular filtration rate," Ann Intern Med. 2009;150(9):604-12.
Levin et al., "The myocardium-protective Gly-49 variant of the beta 1-adrenergic receptor exhibits constitutive activity and increased desensitization and down-regulation," J. Biol.Chem., 277:30429-30435 (2002).
Lewin et al., "meta- and para-isothiocyanato-t-butylbicycloorthobenzoate: irreversible ligands of the gamma-aminobutyric acid-regulated chloride ionophore," Mol. Pharmacol., 35:189-194 (1989).
Li et al., "Effect of Vitamin A Supplementation on Rhodopsin Mutants Threonine-17 -> Methionine and Proline-347 -> Serine in Transgenic Mice and in Cell Cultures," Proc Natl Acad Sci USA, 95(20):11933-11938 (1998).
Liang et al., "Ocular safety of cationic emulsion of cyclosporine in an in vitro corneal wound-healing model and an acute in vivo rabbit model," Mol Vis, 2012; 18:2195-204.
Liu et al., "Comparison of human, mouse, rat, and guinea pig histamine H4 receptors reveals substantial pharmacological species variation," J. Pharmacol. Exp. Ther., 299:121-130 (2001).

(56) References Cited

OTHER PUBLICATIONS

Loftsson et al., "Cyclodextrin Microparticles for Drug Delivery to the Posterior Segment of the Eye: Aqueous Dexamethasone Eye Drops," Journal of Pharmacy and Pharmacology, 2007; 59(5):629-635.
Loftsson et al., "Cyclodextrins in Eye Drop Formulations: Enhanced Topical Delivery of Corticosteroids to the Eye," Acta Ophthalmologica Scandinavica, 2002; 80(2):144-150.
Lopachin et al., "Molecular mechanisms of aldehyde toxicity: a chemical perspective," Chem Res Toxicol, 2014; 27(7):1081-91.
Lovenberg et al., "Cloning and functional expression of the human histamine H3 receptor," Mol. Pharmacol., 55:1101-1107 (1999).
Lukas, R.J., "Characterization of curaremimetic neurotoxin binding sites on membrane fractions derived from the human medulloblastoma clonal line, T15671," J. Neurochem., 46:1936-1941 (1986).
Luthin et al., "Characterization of two affinity states of adenosine A2a receptors with a new radioligand, 2-[2-(4-amino-3- [125I]iodophenyl)ethylamino]adenosine," Mol. Pharmacol., 47:307-313 (1995).
MacDonald et al., "ADX-102, a novel aldehyde trap, reduces nociceptive behavior in mouse models of carrageenan and CFA induced pain," Int'l Conference on Pain Research & Management Abstract, J Pain Relief, 5 (5 Suppl):50 (Oct. 2016).
MacDonald et al., "Inhibition of fibroblast activation to the myofibroblast phenotype in neonatal rat cardiac fibroblasts using a small molecule aldehyde trap," ASCB Annual Meeting Abstract, p. 2 (Dec. 2016).
MacDonald et al., "Molecular characterization of the melanin-concentrating hormone/receptor complex: identification of critical residues involved in binding and activation," Mol. Pharmacol., 58:217-225 (2000).
MacDonald et al., "Novel Small Molecule Aldehyde Sequestering Agents Demonstrate Broad Therapeutic Potential for Ocular Inflammation," ARVO Annual Meeting Abstract, 2 pages (Jul. 2018).
MacDonald et al., "The novel aldehyde trap, ADX-102, reduces inflammation-mediated lung infiltrate in a mouse model of LPS-induced acute lung injury," 13th World Congress on Inflammation Abstract, p. 192 (Jul. 2017).
MacKenzie et al., "Characterization of the human dopamine D3 receptor expressed in transfected cell lines," Eur. J. Pharmacol., 266:79-85 (1994).
Maeda et al., "Involvement of All-trans-retinal in Acute Light-induced Retinopathy of Mice," J Biol Chem, 284(22):15173-83 (May 2009).
Maeda et al., "Primary amines protect against retinal degeneration in mouse models of retinopathies," Nat Chem Biol, 2011; 8(2):170-178.
Maguire et al., "Orphan-receptor ligand human urotensin II: receptor localization in human tissues and comparison of vasoconstrictor responses with endothelin-1," Brit. J. Pharmacol., 131:441-446 (2000).
Malondialdehyde, Wikipedia, 2008, retrieved from the internet on Aug. 4, 2021 at https://en.wikipedia.org/wiki/Malondialdehyde.
Malondialdehyde, Wikipedia. Edited 2020; Accessed 2021: https://en.wikipedia.org/w/index.php?title=Malondialdehyde&oldid=993228459.
Mandell et al., "The Aldehyde Trap NS2 Reduces Ocular Inflammation in an Endotoxin-Induced Model in Rats," ARVO Annual Meeting Abstract, 2 pages (Jun. 2015).
Mandell et al., "The Aldehyde Trap NS2 Reduces Ocular Inflammation in an Endotoxin-Induced Model in Rats," Investigative ophthalmology & visual science. 2015; 56(7):3095.
Mantey et al., "Discovery of a high affinity radioligand for the human orphan receptor, bombesin receptor subtype 3, which demonstrates that it has a unique pharmacology compared with other mammalian bombesin receptors," J. Biol. Chem., 272:26062-26071 (1997).
Marnett, "Oxy radicals, lipid peroxidation and DNA damage," Toxicology, 181-182:219-222 (2002).

Martin et al., "Molecular cloning and functional characterization of murine cysteinyl-leukotriene 1 (CysLT(1)) receptors.," Biochem. Pharmacol., 62:1193-1200 (2001).
Matern et al., "Seizures in a boy with succinic semialdehyde dehydrogenase deficiency treated with vigabatrin (gamma-vinyl-GABA)," J Inherit Metab Dis., 19(3):313-8 (1996).
Mathew et al., "Updates in the management of diabetic macular edema," J Diabetes Res. 2015; 2015:794036.
Maurice et al., "Advances in targeting cyclic nucleotide phosphodiesterases," Nat Rev Drug Discov., 2014; 13:290-314.
McCord et al., "Superoxide dismutase. An enzymic function for erythrocuprein (hemocuprein).," J. Biol. Chem., 1969; 244: 6049-6055.
McGinnity et al., "Evaluation of fresh and cryopreserved hepatocytes as in vitro drug metabolism tools for the prediction of metabolic clearance." Drug Metab. Dispos., 32(11):1247-1253 (2004).
McLaurin et al., "Phase 3 Randomized Double-Masked Study of Efficacy and Safety of Once-Daily 0.77% Olopatadine Hydrochloride Ophthalmic Solution in Subjects with Allergic Conjunctivitis Using the Conjunctival Allergen Challenge Model," Clinical Science, 2015; 34(10):1245-1251.
Medline Plus. Macular Degeneration—age-related. (6 pages) (2013).
Meijer et al., "Biochemical and cellular effects of roscovitine, a potent and selective inhibitor of the cyclin-dependent kinases cdc2, cdk2 and cdk5," Eur. J. Biochem., 243:527-536 (1997).
Meng et al., "Cloning and pharmacological characterization of a rat kappa opioid receptor," Proc. Natl. Acad. Sci. U.S.A., 90:9954-9958 (1993).
Merck Sharp & Dohme Corp., "Bridion® (sugammadex) Injection Prescribing Information, for intravenous use," Highlights of Prescribing Information. 2015.
Mialet et al., "Isolation of the serotoninergic 5-HT4(e) receptor from human heart and comparative analysis of its pharmacological profile in C6-glial and CHO cell lines," Brit. J. Pharmacol., 129:771-781 (2000).
Miceli et al., "Efficacy of keratinocyte growth factor-2 in dextran sulfate sodium-induced murine colitis," J Pharmacol Exp Ther, 290(1):464-71 (Jul. 1999).
Mishra et al., "Recent Patents and Emerging Therapeutics in the Treatment of Allergic Conjunctivitis," Recent Pat. Inflamm. Allergy Drug Discov.; 2011; 5(1):26-36.
Mittl et al., "Structure of recombinant human CPP32 in complex with the tetrapeptide acetyl-Asp-Val-Ala-Asp fluoromethyl ketone," J. Biol. Chem., 272:6539-6547 (1997).
Monaghan et el., "The distribution of [3H]kainic acid binding sites in rat CNS as determined by autoradiography," Brain Res., 252:91-100 (1982).
Monsma et al., "Cloning and expression of a novel serotonin receptor with high affinity for tricyclic psychotropic drugs," Mol. Pharmacol., 43:320-327 (1993).
Mulheron et al., "Human 5-HT1A receptor expressed in insect cells activates endogenous G(o)-like G protein(s)," J. Biol. Chem., 269:12954-12962 (1994).
Muller-Enoch et al., "[6.7-Dihydroxycoumarin (Aesculetin) as a substrate for catechol-o-methyltransferase (author's transl)]," Z. Naturforsch., 31:280-284 (1976).
Munro et al., "Molecular characterization of a peripheral receptor for cannabinoids," Nature, 365:61-65 (1993).
Murphy et al., "Characterization of quisqualate recognition sites in rat brain tissue using DL-[3H]alpha-amino-3-hydroxy-5-methylisoxazole-4-propionic acid (AMPA) and a filtration assay," Neurochem. Res., 12:775-781 (1987).
Na et al., "Molecular profiling of a 6-hydroxydopamine model of Parkinson's disease," Neurochem Res. 2010;35(5):761-72.
Nagai et al., Improved corneal toxicity and permeability of tranilast by the preparation of ophthalmic formulations containing its nanoparticles, J Oleo Sci, 2014; 63(2):177-86.
Nagase et al., "Design and characterization of a fluorogenic substrate selectively hydrolyzed by stromelysin 1 (matrix metalloproteinase-3),"J. Biol. Chem., 269:20952-20957 (1994).
Nakamura et al., "Involvement of Oxidative Stress on Corneal Epithelial Alterations in a Blink-Suppressed Dry Eye," Investigative Ophthalmology and Visual Science, 2007; 48(4):1552-1558.

(56) References Cited

OTHER PUBLICATIONS

Negre-Salvayre et al., "Advanced Lipid Peroxidation End Products in Oxidative Damage to Proteins. Potential Role in Diseases and Therapeutic Prospects for the Inhibitors," Br J Pharmacol, 2008; 153(1):6-20.
Nema et al., "Excipients and Their Use in injectable Products," PDA J Pharm Sci Technol, 51(4):166-171 (1997).
Zhou et al., "Cloning and expression of human and rat D1 dopamine receptors," Nature, 347:76-80 (1990).
Nerurkar et al., "Beta-Arylglutaconic Acids. II. Imides of Certain Beta-Arylglutaconic and Glutaric Acids," J Org Chem, 24(12):2055-2056 (1959).
Nielsen and Bundgaard, "Glycolamide esters as biolabile prodrugs of carboxylic acid agents: synthesis, stability, bioconversion, and physicochemical properties," J Pharm Sci. 1988;77(4):285-98.
Niwa et al., "Protein oxidative damage in the stratum corneum: Evidence for a link between environmental oxidants and the changing prevalence and nature of atopic dermatitis in Japan," Br J Dermatol., 2003; 149:248.
Nociari et al., "Beta cyclodextrins bind, stabilize, and remove lipofuscin bisretinoids from retinal pigment epithelium," Proc Natl Acad Sci U.S.A., 2014; E1402-E1408.
Noorwez et al., "Pharmacological Chaperone-mediated in Vivo Folding and Stablization of the P23H-Opsin Mutant Associated with Autosomal Dominant Retinitis Pigmentosa," J Biol Chem, 278:14442-14450 (2003).
O'Brien et al., "Aldehyde Sources, Metabolism, Molecular Toxicity Mechanisms, and Possible Effects on Human Health," Crit Rev Toxicol, 2005; 35:609-662.
O'Regan et al., "Filaggrin in atopic dermatitis," J Allergy Clin Immunol. 2009; 124(3 Suppl 2):R2-6.
Obourn et al., "Hormone- and DNA-binding mechanisms of the recombinant human estrogen receptor," Biochemistry 32(24):6229 (1993).
Okayasu et al., "A novel method in the induction of reliable experimental acute and chronic ulcerative colitis in mice," Gastroenterology. 1990;98(3):694-702.
Organisciak et al., "Susceptibility to Retinal Light Damage in Transgenic Rats with Rhodopsin Mutations," Invest Ophthalmol Vis Sci, 44(2):486-492 (2003).
Ousler et al., "Use of the Controlled Adverse Environment (CAE) in Clinical Research: A Review," Opthalmology and Therapy, Sep. 27, 2017, vol. 6, pp. 263-276.
Pacholczyk et al., "Expression cloning of a cocaine- and antidepressant-sensitive human noradrenaline transporter," Nature, 350:350-354 (1991).
Pal et al., "Sulfur mustard analog induces oxidative stress and activates signaling cascades in the skin of SKH-1 hairless mice," Free Radic Biol Med., 47(11):1640-51 (2009).
Palchaudhuri et al., "Corticotropin-releasing factor receptor type 1 from Tupaia belangeri-cloning, functional expression and tissue distribution," Eur. J. Biochem., 258:78-84 (1998).
Parish et al., "Isolation and One-Step Preparation of A2E and iso-A2E, Fluorophores from Human Retinal Pigment Epithelium," Proc Natl Acad Sci USA, 95(25):14609-14613 (1998).
Park et al., "Modulation of Acute Inflammation and Keratocyte Death by Suturing, Blood, and Amniotic Membrane in PRK," Invest. Opthalmol Vis Sci. 2000;41(10):2906-14.
Park et al., "Homogeneous proximity tyrosine kinase assays: scintillation proximity assay versus homogeneous time-resolved fluorescence," Anal. Biochem., 269:94-104 (1999).
Parracho et al., "Differences between the gut microflora of children with autistic spectrum disorders and that of healthy children," Journal of Medical Microbiology, 54:987-991 (2005).
Patel C.Y., "Subtype selectivity of peptide analogs for all five cloned human somatostatin receptors (hsstr 1-5)," Endocrinology, 135:2814-2817 (1994).
PCT International Search Report from PCT/US2010/059719, Feb. 8, 2011.
PCT International Search Report from PCT/US2014/012762, Jul. 18, 2014.
PCT International Search Report from PCT/US2016/048054, Nov. 4, 2016.
PCT International Search Report from PCT/US2016/048064, Nov. 15, 2016.
PCT International Search Report from PCT/US2017/020020, May 24, 2017.
PCT International Search Report from PCT/US2017/031808, Aug. 11, 2017.
PCT International Search Report from PCT/US2017/047958, Oct. 31, 2017.
PCT International Search Report from PCT/US2018/023000, Jun. 1, 2018.
PCT International Search Report from PCT/US2019/041942, Sep. 30, 2019.
PCT International Search Report from PCT/US2019/045206, Oct. 17, 2019.
PCT International Search Report from PCT/US2019/054263, Jan. 6, 2020.
PCT International Search Report from PCT/US2019/064669, Feb. 27, 2020.
PCT International Search Report from PCT/US2020/024022, Jun. 17, 2020.
PCT International Search Report from PCT/US2020/031138, Jul. 13, 2020.
PCT International Search Report from PCT/US2020/031219, Aug. 31, 2020.
PCT International Search Report from PCT/US2021/023884, Jul. 28, 2021.
PCT International Search Report from PCT/US2021/032335, Jul. 27, 2021.
PCT International Search Report from PCT/U.S. Pat. No. 2021027148, Jun. 28, 2021.
PCT International Search Report from PCT/US2022/035898, Nov. 16, 2022.
Pellock, "Balancing clinical benefits of vigabatrin with its associated risk of vision loss," Acta Neurologica. Scandinavica. Supplementum., 124(s192):83-91 (2011).
Petroski et al., "Selective labeling of embryonic neurons cultured on astrocyte monolayers with 5(6)-carboxyfluorescein diacetate (CFDA)," Journal of Neuroscience Methods, 52(1):23-32 (1994).
Pfaar et al., "Perspectives in allergen immunotherapy: 2017 and beyond," Allergy, 2018; 73(Suppl 104):5-23.
Pontikis et al., "Cyclodextrin alleviates neuronal storage of cholesterol in Niemann-Pick C disease without evidence of detectable blood-brain barrier permeability," Journal of Inherited Metabolic Disease, 2013; 36(3):491-498.
Pozzi et al., "Modification of Collagen IV by Glucose or Methylglyoxal Alters Distinct Mesangial Cell Function," Journal of the American Society of Nephrology, 20:2119-2125 (2009).
Pred Forte Prescribing Information, Allergan, 5 pages (2017).
Pristupa et al., "Pharmacological heterogeneity of the cloned and native human dopamine transporter: disassociation of [3H]WIN 35,428 and [3H]GBR 12,935 binding.," Mol. Pharmacol., 45:125-135 (1994).
Pruneau et al., "LF 16.0335, a novel potent and selective nonpeptide antagonist of the human bradykinin B2 receptor," Brit. J. Pharmacol., 125:365-372 (1998).
Pubchem, 1824609-67-7, SID 333824451, Apr. 24, 2017 (6 pages).
Pubchem, 2-(3-Aminoquinolin-2-yl)propan-2-ol, CID 117758222, Feb. 23, 2016, modified Jun. 13, 2020 (11 pages).
Pubchem, SCHEMBL16316728, Cid 117758222, Feb. 23, 2016, modified Sep. 30, 2017 (13 pages).
Roberts et al., "Experimental Organic Chemistry—A Miniscale Approach," copyright 1994 by Saunders College Publishing, pp. 580-581 and 584-586.
Roche, "Tween 20," Sigma-Aldrich Datasheet. Retrieved Nov. 19, 2020: https://www.sigmaaldrich.com/catalog/product/roche/11332465001?lang=en&region=US#:~: text=Tween%2020%>.
Rohrer et al., "Cloning and characterization of a fourth human somatostatin receptor," Proc. Natl. Acad. Sci. U.S.A., 90:4196-4200 (1993).

(56) References Cited

OTHER PUBLICATIONS

Roumen et al., "Serum Lipofuscin as a Prognostic Indicator of Adult Respiratory Distress Syndrome and Multiple Organ Failure," British Journal of Surgery, 1994, vol. 81, pp. 1300-1305.
Rønborg et al., "Exposure chamber for allergen challenge. The development and validation of a new concept," Allergy, 1996; 51(2):82-8.
Sahi et al., "Hepatocytes as a tool in drug metabolism, transport and safety evaluations in drug discovery." Current Drug Discov. Technol., 7(3):188-198 (2010).
Salvatore et al., "Molecular cloning and characterization of the human A3 adenosine receptor," Proc. Natl. Acad. Sci. U.S.A., 90:10365-10369 (1993).
Samsonov et al., "Impact of Atherosclerosis- and Diabetes-Related Dicarbonyls on Vascular Endothelial Permeability: A Comparative Assessment," Oxid. Med. Cell Longev. Article 1625130 (2017).
Sanchez et al., "Allergic Conjunctivitis," J Investig Allergol Clin Immunol., 2011; 21(2):1-19.
Sandikci et al., "Lipid Peroxidation and Antioxidant Defence System in Patients with Active or Inactive Behcet's Disease," Acta Derm Venereol, 2003; 83:342-346.
Sarafian et al., "Synergistic cytotoxicity of Delta(9)-tetrahydrocannabinol and butylated hydroxyanisole," Toxicology Letters, 133(2-3):171-179 (2002).
Sarfare et al., "Biocompatibility of a Synthetic Biopolymer for the Treatment of Rhegmatogenous Retinal Detachment," J Clin Exp Ophthalmol. 2015;6(5):475.
Sarup et al., "Resolution of high and low affinity progesterone receptors from human breast carcinoma T47D cells," J. Biol. Chem., 263:5624-5633 (1988).
Sasaki et al., "Retinal drug delivery using eyedrop preparations of poly-L-lysine-modified liposomes," Eur J Pharm Biopharm, 2013; 83(3):364-9.
Satici et al., "Malondialdehyde and antioxidant enzyme levels in the aqueous humor of rabbits in endotoxin-induced uveitis," Eur J Ophthalmol, 2003; 13(9-10):779-83.
Sayed et al., "Metabolic Activation of R,S-1-(Tetrahydro-2-turanyl)-5-fluorouracil (Ftorafur) to 5-fluorouracil by Soluble Enzymes," Cancer Research, 43:4039-4044 (1983).
Schaumberg et al., "Prevalence of dry eye syndrome among US women," Am J Ophthalmol. 2003;136(2):318-26.
Schaumberg et al., "Epidemiology of dry eye syndrome," Lacrimal Gland, Tear Film, and Dry Eye Syndromes 3, Kluwer Academic/Plenum Publishers, pp. 989-998 (2002).
Schaumberg et al., "Prevalence of Dry Eye Disease among US Men: Estimates from the Physicians' Health Studies," Arch Ophthalmol, 2009; 127(6):763-768.
Schioth et al., "Characterization of the binding of MSH-B, HB-228, GHRP-6 and 153N-6 to the human melanocortin receptor subtypes," Neuropeptides, 31:565-571 (1997).
Schramm et al., "The Cross-linked Biopolymer Hyaluronic Acid as an Artificial Vitreous Substitute," Invest Ophthalmol Vis Sci, 53(2):613-621 (Feb. 2012).
Schwartz and Work, "Measurement and estimation of GFR in children and adolescents," Clin J Am Soc Nephrol. 2009;4(11):1832-43.
Schwartz et al., "Tamponade in surgery for retinal detachment associated with proliferative vitreoretinopathy," Cochrane Database Syst Rev. 2020;5(5):CD006126.
Schwinn et al., "Molecular cloning and expression of the cDNA for a novel alpha 1-adrenergic receptor subtype," J. Biol. Chem., 265:8183-8189 (1990).
Sciuto et al., "Therapeutic Treatments of Phosgene-Induced Lung Injury," Inhal Toxicol, 16(8):565-580 (2004).
Search Report and Written Opinion issued by the Intellectual Property Office of Singapore for Singapore Patent Application No. 11201504859Y dated Aug. 1, 2016 (12 pages).
Serbecic et al., "Anti-oxidative vitamins prevent lipid-peroxidation and apoptosis in corneal endothelial cells," Cell Tissue Res, 320(3):465-75 (Jun. 2005).
Shank et al., "Ion and temperature effects on the binding of gamma-aminobutyrate to its receptors and the high-affinity transport system," J. Neurochem., 54:2007-2015 (1990).
Shen et al., "Molecular cloning and expression of a 5-hydroxytryptamine7 serotonin receptor subtype," J. Biol. Chem., 268:18200-18204 (1993).
Sheppard et al., "Targeting Anterior Uveitis: A Focus on Iontophoresis and Other Advanced Technologies," 2018.
Sheppard et al., "Targeting Anterior Uveitis: A Focus on Iontophoresis . . . ", Sep. 1, 2018, Retrieved from Internet URL: https://www.nyee.edu/files/NYEE/Health%20Professionals/Continuing%20Medical%20Education/Enduring%20CME%20Activities/158_supplement.small_v1_FINAL%20082818.pdf.
Sheppard et al., "A Randomized, Comparator-Controlled Phase 2 Clinical Trial of ADX-102 Ophthalmic Solution in Noninfectious Anterior Uveitis," ARVO Annual Meeting Abstract, Invest Ophth Vis Sci. 2017; 58(8):1231.
Sherman et al., "Cellular Defenses Against Unfolded Proteins: A Cell Biologist Thinks about Neurodegenerative Diseases," Neuron, 29(1):15-32 (2001).
Shipp et al., "Common acute lymphoblastic leukemia antigen (CALLA) is active neutral endopeptidase 24.11 ("enkephalinase"): direct evidence by cDNA transfection analysis," Proc Natl Acad Sci USA. 86:297 (1989).
Shoemaker et al., "[3H]diltiazem binding to calcium channel antagonists recognition sites in rat cerebral cortex," Eur. J. Pharmacol., 111:273-277 (1985).
Siegrist et al., "Radioreceptor assay for alpha-MSH using mouse B16 melanoma cells+.," J. Recep. Res., 8:323-343 (1988).
Sieving et al., "Inhibition of the Visual Cycle in vivo by 13-cis Retinoic Acid Protects from Light Damage and Provides a Mechanism for Night Blindness in Isotretinoin Therapy," Proc Natl Acad Sci USA, 98(4):1835-1840 (2001).
Sills et al., "[3H]CGP 39653: a new N-methyl-D-aspartate antagonist radioligand with low nanomolar affinity in rat brain," Eur. J. Pharmacol., 192:19-24 (1991).
Simeone et al., "Modification of the Pyridine Moiety of Nonpeptidyl Indole GnRH Receptor Antagonists," Bioorganic & Medicinal Chemistry Letters, 12(22):3329-3332 (2002).
Simonin et al., "The human delta-opioid receptor: genomic organization, cDNA cloning, functional expression, and distribution in human brain," Mol. Pharmacol., 46:1015-1021 (1994).
Singh et al., "The epidemiology of ocular and nasal allergy in the United States, 1988-1994," J. Allergy Clin. Immunol., 2010; 126(4):778-783.
Smit et al., "Regulation of the human histamine H1 receptor stably expressed in Chinese hamster ovary cells," Brit. J. Pharmacol., 117:1071-1080 (1996).
Smith and Cass, "Oxidative stress and dopamine depletion in an intrastriatal 6-hydroxydopamine model of Parkinson's disease," Neuroscience. 2007;144(3):1057-66.
Smith et al., "Basic pathogenic mechanisms operating in experimental models of acute anterior uveitis," Immunol Cell Biol, 1998; 76:497-512.
Snead et al., "Gamma-hydroxybutyric acid," New England Journal of Medicine, 352(26):2721- 2732 (2005).
Snell et al., "Novel structure having antagonist actions at both the glycine site of the N-Methyl-D-Aspartate receptor and neuronal voltage-sensitive sodium channels. Biochemical, electrophysiological, and behavioral characterization," J Pharmacol Exp Ther, 292(1):215-227 (2000).
Spadea et al., "Corneal wound healing after laser vision correction," Br J Ophthalmol. 2016; 100:28-33.
Spagnol et al., "Efficient synthesis of tricyclic benzobisoxazines by silica gel catalysis," J Org Chem, 2;72(5):1867-1869 (Mar. 2007).
Sparrow et al. "Phospholipid meets all-trans-retinal: the making of RPE bisretmoids," Journal of Lipid Research, 51: 247-261 (2010).
Speth et al., "Benzodiazepine receptors: temperature dependence of [3H]flunitrazepam binding," Life Sci., 24:351-358 (1979).
Stefansson and Loftsson, "Cyclodextrins in Eye Drop Formulations," J Incl Phenom Macrocycl Chem. 2002;44:23-27(abstract).

(56) References Cited

OTHER PUBLICATIONS

Stehle et al., "Molecular cloning and expression of the cDNA for a novel A2-adenosine receptor subtype," Mol. Endocrinol., 6:384-393 (1992).
Stevenson et al., "Dry eye disease: an immune-mediated ocular surface disorder," Arch Ophthalmol. 2012; 130(1): 90-100.
Struys et al., "Determination of the GABA analogue succinic semialdehyde in urine and cerebrospinal fluid by dinitrophenylhydrazine derivatization and liquid chromatography-tandem mass spectrometry: application to SSADH deficiency," J Inherit Metab Dis., 28(6):913-20 (2005).
Struys et al., "Metabolism of gamma-hydroxybutyrate to d-2-hydroxyglutarate in mammals: further evidence ford-2-hydroxyglutarate transhydrogenase," Metabolism, 55(3):353-8 (2006).
Study showing effect of ADX-102 on Fibrotic Changes in Cardiac Fibroblasts Following Cell Stress, American Society for Cell Biology Annual Meeting, Dec. 3-7, 2016 (2 pages).
Sus et al., "Uber die Lichtreaktion der o-Chinondiazide V Mitteilungl) Ubergange heterocyclischer 6-Ringe in heterocyclische 5-Ringe," Liebigs Ann. Chem. 583:150 (1953).
Tahara et al., "Pharmacological characterization of the human vasopressin receptor subtypes stably expressed in Chinese hamster ovary cells," Brit. J. Pharmacol., 125:1463-1470 (1998).
Tang-Liu et al., "Effects of four penetration enhancers on corneal permeability of drugs in vitro," Journal of Pharmaceutical Sciences, 1994; 83(1):85-90.
Tatsumi et al., "Pharmacological profile of neuroleptics at human monoamine transporters," Eur. J. Pharmacol., 368: 277-283 (1999).
Tayeh et al., "Macrophage oxidation of L-arginine to nitric oxide, nitrite, and nitrate. Tetrahydrobiopterin is required as a cofactor," J. Biol. Chem., 264:19654-19658 (1989).
Tempest-Roe et al., "Local therapies for inflammatory eye disease in translation: past, present and future," BMC Ophthalmol., 2013; 13(1):39.
Tewari-Singh et al., "Silibinin attenuates sulfur mustard analog-induced skin injury by targeting multiple pathways connecting oxidative stress and inflammation," PLoS One 7(9):e46149 (2012).
Tian et al., "First total synthesis and determination of the absolute configuration of 1-N-methyl-3-methylamino- [N-butanoicacid-3-(9-methyl-8-propen-7-one)-amide]—benzo [f][1,7]naphthyridine-2-one, a novel benzonaphthyridine alkaloid," Tetrahedron Letters, 53:4892-4895 (2012).
Tikly et al., "Lipid peroxidation and trace elements in systemic sclerosis," Clinical Rheumatology, 25(3):320-324 (2006).
Torkildsen et al., "Efficacy and safety of olopatadine hydrochloride 0.77% in patients with allergic conjunctivitis using a conjunctival allergen-challenge model," Clinical Ophthalmology, 9:1703-1713 (2015).
Toth et al., "A simple, continuous fluorometric assay for HIV protease," Int. J. Pept. Protein Res., 36:544-550 (1990).
Tsugeno et al., "Regions of the molecule responsible for substrate specificity of monoamine oxidase A and B: a chimeric enzyme analysis," J. Biochem., 118 (5) 974-80 (1995).
Tsuzuki et al., "Molecular cloning and expression of the gene encoding human angiotensin II type 2 receptor.," Biochem. Biophys. Res. Commun., 200:1449-1454 (1994).
Tukozkan et al., "Measurement of Total Malondialdehyde in Plasma and tissues by High-Performance Liquid Chromatography and Thiobarbituric Acid Assay," Firat Tip Dergisi, 11 (2):88-92 (2006).
Turk et al., "Serum anti-carbonic anhydrase antibodies and oxidant-antioxidant balance in patients with acute anterior uveitis," Ocul Immunol Inflamm, 22(2):127-32 (Apr. 2014).
Ueda et al., "Evaluation of a Sulfobutyl Ether 13-Cyclodextrin as a Solubilizing/Stabilizing Agent for Several Drugs," Drug Dev Ind Pharm, 24(9):863-867(1998).
Upadhyaya et al., "The sphingolipid degradation product trans-2-hexadecenal forms adducts with DNA," Biochem Biophy Res Comm., 424(1):18-21 (2012).
Vanachayangkul et al., "Inhibition of heme peroxidases by melamine," Enzyme Research, 2012:416062 (2012).
Vignon et al., "[3H]thienyl-phencyclidine ([3H]TCP) binds to two different sites in rat brain. Localization by autoradiographic and biochemical techniques," Brain Res., 378:133-141 (1986).
Vlaskina et al., "Novel Synthesis of Substituted Benzimidazoles by Reduction of Esters of 4-Alkylamino-3,5-dinitrobenzoic Acids by Tin Chloride," Chemistry of Heterocyclic Compounds, vol. 40(4):523-524 (2004).
Vogel et al., "Thirty years beyond discovery-clinical trials in succinic semialdehyde dehydrogenase deficiency, a disorder of GABA metabolism," J Inherit Metab Dis., 36(3):401-10 (2013).
Voziyan et al., "A Post-Amadori Inhibitor Pyridoxamine also Inhibits Chemical Modification of Proteins by Scavenging Carbonyl Intermediates for Carbohydrate and Lipid Degradation," J Biol Chem, 277(5):3397-3403 (2002).
Wagner et al., "Omega-conotoxin GVIA binding to a high-affinity receptor in brain: characterization, calcium sensitivity, and solubilization," J. Neurosci., 8:3354-3359 (1988).
Wakamatsu et al., "Evaluation of lipid oxidative stress status and inflammation in atopic ocular surface disease," Mol Vis, 16:2465-75 (Nov. 2010).
Wall et al., "Plant Antitumor Agents. 30. Synthesis and Structure Activity of Novel Camptothecin Analogs," J. Med. Chem., 36(18):2689-2700 (1993).
Walter et al., "Novel Complex N-Heterocycles via Intramolecular 1,5-Electrocyclizations: 1,2,3,4,4a,5,5a, 10-Octahydropyrido-[4",3":2',3']cyclobuta[1',2':4,5]pyrrolo[2,3-b]pyridines," Heterocycles, 48(8):1581-1591 (1998).
Wang et al., "A facile one-pot synthesis of 2-substituted-3-aminoquinolines: Preparation of benzo[b]naphthyridine-3-carbonitriles," Tetrahedron, 60(13):2937-2942 (2004).
Wang et al., "Human mu opiate receptor. cDNA and genomic clones, pharmacologic characterization and chromosomal assignment," FEBS Lett., 338:217-222 (1994).
Wang et al., "Markers of oxidative and nitrosative stress in systemic lupus erythematosus: correlation with disease activity," Arthritis and Rheumatism, 62(7):2064-2072 (2010).
Wang, X.K., "Pharmacological study on recombinant human GABA-A receptor complex containing alphas (leucine 155 to valine) combined with beta3gamma2s subunits," Acta. Pharmacol. Sin., 22:521-523 (2001).
Waslidge et al., "A colorimetric method for the determination of lipoxygenase activity suitable for use in a high throughput assay format," Anal. Biochem., 231:354-358 (1995).
Weaver et al., "The Th17 pathway and inflammatory diseases of the intestines, lungs, and skin," Annu. Rev. Pathol., 8:477-512 (2013).
Webb et al., "Intralesional cytokines in chronic oxazolone-induced contact sensitivity suggest roles for tumor necrosis factor alpha and interleukin-4," J Invest Dermatol, 111(1):86-92 (Jul. 1998).
Weishaar et al., "Multiple molecular forms of cyclic nucleotide phosphodiesterase in cardiac and smooth muscle and in platelets. Isolation, characterization, and effects of various reference phosphodiesterase inhibitors and cardiotonic agents," Biochem. Pharmacol., 35:787-800 (1986).
Weng et al., "Insights into the Function of Rim Protein in Photoreceptors and Etiology of Stargardt's Disease from the Phenotype in aber Knockout Mice," Cell, 98(1):13-23 (1999).
Westphal et al., "Reactions with Pyridinium Pyruvic Acid Esters," Pharmazie 1976;31(11)770-773.
Westphal et al., "Reactions with Pryridinium Pyruvic Acid Esters," Pharmazie, 31(11)770-773 (1976) [English Translation].
Wieland et al., "Subtype selectivity and antagonistic profile of the nonpeptide Y1 receptor antagonist BIBP 3226," J. Pharmacol. Exp. Ther., 275:143-149 (1995).
Winfield and Richards, "Ophthalmic products," Pharmaceutical Practice, Churchill Livingstone. 2004;265-268.
Witt-Enderby et al., "Characterization and regulation of the human ML1A melatonin receptor stably expressed in Chinese hamster ovary cells," Mol. Pharmacol., 50:166-174 (1996).
Wolkenberg et al., "Design, synthesis, and evaluation of novel 3,6-diaryl-4-aminoalkoxyquinolines as selective agonists of somatostatin receptor subtype 2," J Med Chem, 54(7):2351-2358 (2011).

(56) References Cited

OTHER PUBLICATIONS

Wood et al., "Aldehyde Load in Ischemia-Reperfusion Brain Injury: Neuroprotection by Neutralization of reactive Aldehydes with Phenelzine," Brain Res, 1122(1):184-190 (2006).
Wood et al., "The concept of "aldehyde load" in neurodegenerative mechanisms: cytotoxicity of the polyamine degradation products hydrogen peroxide, acrolein, 3-aminopropanal, 3-acetamidiorioanal and 4-aminobutanal in a retinal ganglion cell line," Brain Research, 1145:150-156 (2007).
Wurch et al., "Sequence and functional analysis of cloned guinea pig and rat serotonin 5-HT1D receptors: common pharmacological features within the 5-HT1D receptor subfamily," J. Neurochem., 68:410-418 (1997).
Wynn, "Cellular and molecular mechanisms of fibrosis," J Pathol. 2008;214(2):199-210.
Yadav et al., "Regulation of NF-κB-Induced Inflammatory Signaling by Lipid Peroxidation-Derived Aldehydes," Oxidative Med & Cell Longev, 2013, Art ID 690545, 11 pages (2013).
Yarnell, "Light Flips the Lipid Switch: Palmitoylation—the reversible attachment of palmitate to proteins—gets a new role in vision," C&EN, 82(29):22-23 (2004).
Yokomizo et al., "Hydroxyeicosanoids bind to and activate the low affinity leukotriene B4 receptor, BLT2," J. Biol. Chem., 276:12454-12459 (2001).
Yu et al., "Injectable Chemically Crosslinked Hydrogel for the Controlled Release of Bevacizumab in Vitreous: A 6-Month In Vivo Study," Transl Vis Sci Technol, 4(2,5):1-11 (2015).
Zagol-Ikapitte et al., "Characterization of scavengers of γ-ketoaldehydes that do not inhibit prostaglandin biosynthesis," Chem Res Toxicol, 23(1):240-250 (2010).
Zarkovic "4-hydroxynonenal and neurodegenerative diseases," Molecular Aspects of Medicine, 2003; 24(4-5):293-303.
Zava et al., "Androgen receptor assay with [3H]methyltrienolone (R1881) in the presence of progesterone receptors," Endocrinology, 104:1007-1012 (1979).
Zhang et al., "Potent nonsteroidal progesterone receptor agonists: synthesis and SAR study of 6-aryl benzoxazines," Bioorg Med Chem Lett, 12(5):787-90 (Mar. 2002).
Zhang et al., "Practical ophthalmic pharmacology," People's Military Medical Press, 2015; p. 590.
Zhou et al., "Chemical and biological evidence for base propenals as the major source of the endogenous M1dG adduct in cellular DNA," J Biol Chem., 280(27):25377-82 (2005).
"Shin iyakuhin no kikaku oyobi shaken houhou no settei nituite nituite (Regarding the setting of the standard and test method of a new medical product" PMSB/ELD Notification No. 568, May 2001.
Aldeyra Press Release, "Aldeyra Therapeutics Announces First Patient Enrolled in Allergic Conjunctivitis Phase 2b Clinical Trial", Feb. 22, 2017, 2 pages.
Aldeyra Therapeutics, "Aldeyra Therapeutics Announces First Patient Enrolled in Allergic Conjunctivitis Phase 3 Clinical Trial", Press Release, May 1, 2018, 2 pages.
Aldeyra Therapeutics, "Positive Results from Phase IIa Clinical Trials in Subjects with Allergic Conjunctivitis", Press Release, Feb. 29, 2016, 3 pages.
Caira, "Crystalline Polymorphism of Organic Compounds", Topics in Current Chemistry, Jan. 1999, 198:163-208.
Kawaguchi et al., "Drug and crystal polymorphism," Journal of human environmental engineering, 2002, 4(2):310-317.
*Neptune Generics, LLC v. Auspex Pharmaceuticals, Inc.*, IPR2015-01313, Paper No. 25, Dec. 9, 2015, 23 pages.
Noriyuki Takada "Souyaku dankai ni okeru genyaku Form sukuri ningu to sentaku (Bulk drug screening and selection in a drug development phase," Pharm Stage, Jan. 2007, 6(10):20-25.
Ono, "Analysis of Salt Selection of Current Active Pharmaceutical Ingredients (API)," Journal of Pharmaceutical Science and Technology, 2013, 73(3):176-182.
Pearl et al., "Inherited disorders of gamma-aminobutyric acid metabolism and advances in ALDH5Al mutation identification," Dev Med Child Neurol., 2015, 57(7):611-617.

Peralta et al., "Distinct primary structures, ligand-binding properties and tissue-specific expression of four human muscarinic acetylcholine receptors," EMBO. J., 1987, 6(13):3923-3929.
Pickering, D.S., "Pharmacological characterization of melatonin binding sites in Syrian hamster hypothalamus," Eur. J. Pharmacol., 1990, 175(1):71-77.
Pubchem CID 149143404, Aug. 12, 2020, 2 pages.
Pubchem CID 4391047, Sep. 14, 2005, 2 pages.
Pufahl et al., "Development of a Fluorescence-based Enzyme Assay of Human 5-lipoxygenase," Anal. Biochem., 2007, 364:204-212.
Quinlan et al., "4-Hydroxy-2-Nonenal Levels Increase in the Plasma of Patients with Adult Respiratory Distress Syndrome as Linoleic Acid Appears to Fall," Free Radic Res. 1994, 21(2):95-106.
Radu et al., "Isotretinoin treatment inhibits lipofuscin accumulation in a mouse model of recessive Stargardt's macular degeneration," Novartis Foundation Symposium 2004, 25(51-63):177-178(Abstract Only).
Radu et al., "Treatment with isoretinin inhibits lipofusion accumulation in a mouse model of recessive Stargardt's macular degeneration," Proc Natl Acad Sci. USA, 2003, 100(8):4742-4747.
Rajewski et al., "Pharmaceutical applications of cyclodextrins. 2. In vivo drug delivery," J Pharm Sci, 1996; 85(11):1142-1169.
Rapp et al., "The effects of local anesthetics on retinal function," Vision Research, 1982, 22(9):1097-1103.
Rauli et al., "Validation of Malondialdehyde and 4-Hydroxy-2-trans-Nonenal Measurement in Plasma by NICI-GC-MS1," J Biochem, 1998, 123:918-923.
Reed, "Lipid peroxidation and neurodegenerative disease", Free Radical Biology and Medicine, 2011, 51(7):1302-1319.
Rees et al., "Cloning and characterisation of the human 5-HT5A serotonin receptor," FEBS Lett., 1994, 355:242-246.
Reynolds et al., "(−)-[3H] desmethoxyverapamil labels multiple calcium channel modulator receptors in brain and skeletal muscle membranes: differentiation by temperature and dihydropyridines," J. Pharmacol. Exp. Ther., 1986, 237: 731-738.
Ricca et al., "Amphetamine derivatives and obesity," Appetite, Apr. 2009, 52(2):405-409.
Rinaldi-Carmona et al., "Characterization of two cloned human CB1 cannabinoid receptor isoforms," J. Pharmacol. Exp. Ther., 1996, 278:871-878.
Rivkees et al., "Identification of domains of the human A 1 adenosine receptor that are important for binding receptor subtype-selective ligands using chimeric A 1 /A2a adenosine receptors," J. Biol. Chem., 270:20485-20490 (1995).
Rizzo et al., "Aldehyde Trapping Agent NS2 Blocks Formation of Fatty Aldehyde Adducts with Phosphatidylethanolamine and Suggests Potential Therapeutic Approach for Sjogren-Larsson Syndrome," Mol Genet and Metab, 114(3):362A (Mar. 2015) [Abstract Only].
Rizzo et al., "Ichthyosis in Sjogren-Larsson syndrome reflects defective barrier function due to abnormal lamellar body structure and secretion," Arch Dermatol Res, 2010, 302(6):443-451.
Rizzo et al., "Sjogren-Larsson syndrome: molecular genetics and biochemical pathogenesis of fatty aldehyde dehydrogenase deficiency," Mol Genet Metab. 2007, 90(1):1-9.
Rizzo et al., "Endogenous antioxidants and radical scavengers," Advances in Experimental Medicine and Biology, 2010, 698:52-56.
Rizzo, Fatty aldehyde and fatty alcohol metabolism: review and importance for epidermal structure and function, Biochim Biophys Acta, Mar. 2014, 1841(3):377-389.
Rizzo, "Genetics and prospective therapeutic targets for Sjogren-Larsson Syndrome," Expert Opin Orphan Druos. 2016, 4(4):395-406.
Rizzo, "The role of fatty aldehyde dehydrogenase in epidermal structure and function" Dermato-Endocrinol, 2011, 3(2):91-99.
Roat, "Allergic Conjunctivitis," Merck Manual Professional Version, 3 pages (2016), Available at: https://www.merckmanuals.com/professional/eye-disorders/conjunctival-and-scleral-disorders/allergic-conjunctivitis.
Roat, "Keratoconjunctivitis Sicca," Merck Manual Professional Version, 5 pages (2016), Available at: https://www.merckmanuals.com/professional/eye-disorders/corneal-disorders/keratoconjunctivitis-sicca.

(56) References Cited

OTHER PUBLICATIONS

Roat, "Ocular Mucous Membrane Pemphigoid," Merck Manual Professional Version, Available at: https://www.merckmanuals.com/professional/eye-disorders/conjunctival-and-scleral-disorders/ocular-mucous-membrane-pemphigoid, 2016, 3 pages.
Roat, "Scleritis," Merck Manual Professional Version, 3 pages (2016), Available at: https://www.merckmanuals.com/professional/eye-disorders/conjunctival-and-scleral-disorders/scleritis.
Roberts et al., "Basic Principles of Organic Chemistry," 2nd edition, copyright 1977 W. A. Benjamin, Inc., pp. 580-582.
Saal, et al. "Pharmaceutical salts: A summary on doses of salt formers from the Orange Book", European Journal of Pharmaceutical Sciences, Jul. 16, 2013, 49(4):614-623.
Serajuddin, "Salt formation to improve drug solubility," Adv Drug Deliv Rev., 2007, 59(7):603-616.
Smalley, Science of Synthesis, 2002, 11:289.
Tanna et al., "Stargardt disease: clinical features, molecular genetics, animal models and therapeutic options," Br J Ophthalmol. 2017; 101 (1):25-30.
Tripathi et al., "Monoamine oxidase-B inhibitors as potential neurotherapeutic agents: An overview and update", Med Res Rev. Sep. 2019, 39(5):1603-1706.
Wermuth, "The Practice of Medicinal Chemistry," Elsevier, Second vol. 1999, pp. 347-365.
Yamano, "Approach to Crystal Polymorph in Process Research of New Drug," Journal of Synthetic Organic Chemistry, 2007, 65:907-913.
Yoko et al., "Drug and Crystal Polymorphism", Journal of Human Environmental Engineering, 2002, 4(2):310-317.
Young et al., "NS2, a novel aldehyde trap, decreases aldehyde levels in dry skin and eye models," Aldeyra therapeutics, 2014, 1 page.
Extended European Search Report received for European Patent Application No. 13865015.5 dated Mar. 31, 2016, 9 pages.
Extended European Search Report received for European Patent Application No. 19891719.7 dated Jul. 27, 2022, 9 pages.
Partial Supplementary European Search Report received for European Patent Application No. 14743711.5 dated Jul. 20, 2016, 14 pages.
PCT International Preliminary Report on Patentability received for PCT/US2006/020320, dated Nov. 30, 2007, 8 pages.
PCT International Preliminary Report on Patentability received for PCT/US2010/059719, dated Jun. 21, 2012, 7 pages.
PCT International Preliminary Report on Patentability received for PCT/US2013/076592, dated Jul. 2, 2015, 7 pages.
PCT International Preliminary Report on Patentability received for PCT/US2014/012356, dated Jul. 28, 2015, 7 pages.
PCT International Preliminary Report on Patentability received for PCT/US2014/012762, dated Aug. 6, 2015, 9 pages.
PCT International Preliminary Report on Patentability received for PCT/US2016/048054, dated Feb. 27, 2018, 5 pages.
PCT International Preliminary Report on Patentability received for PCT/US2016/048064, dated Feb. 27, 2018, 6 pages.
PCT International Preliminary Report on Patentability received for PCT/US2017/020020, dated Sep. 7, 2018, 10 pages.
PCT International Preliminary Report on Patentability received for PCT/US2017/047945, dated Mar. 7, 2019, 7 pages.
PCT International Preliminary Report on Patentability received for PCT/US2017/047958, dated Mar. 7, 2019, 08 pages.
PCT International Preliminary Report on Patentability received for PCT/US2018/023000, dated Sep. 26, 2019, 7 pages.
PCT International Preliminary Report on Patentability received for PCT/US2018/055310, dated Apr. 23, 2020, 6 pages.
PCT International Preliminary Report on Patentability received for PCT/US2019/064669, dated Jun. 17, 2021, 10 pages.
PCT International Preliminary Report on Patentability received for PCT/US2020/024022, dated Oct. 7, 2021, 9 pages.
PCT International Preliminary Report on Patentability received for PCT/US2020/031138, dated Nov. 11, 2021, 6 pages.
PCT International Preliminary Report on Patentability received for PCT/US2020/031219, dated Nov. 11, 2021, 11 pages.
PCT International Preliminary Report on Patentability received for PCT/US2021/023884, dated Oct. 6, 2022, 8 pages.
PCT International Preliminary Report on Patentability received for PCT/US2021/027148, dated Oct. 27, 2022, 7 pages.
PCT International Preliminary Report on Patentability received for PCT/US2021/032335, dated Nov. 24, 2022, 9 pages.
PCT International Preliminary Report on Patentability received for PCT/US2021/035948, dated Dec. 15, 2022, 8 pages.
PCT International Search Report and Written Opinion received for PCT/CN2022/113284, dated Nov. 2, 2022, 6 pages.
PCT International Search Report and Written Opinion received for PCT/US2006/020320, dated Sep. 26, 2006, 10 pages.
PCT International Search Report and Written Opinion received for PCT/US2013/076592, dated Apr. 30, 2014, 10 pages.
PCT International Search Report and Written Opinion received for PCT/US2014/012356, dated May 30, 2014, 11 pages.
PCT International Search Report and Written Opinion received for PCT/US2016/040064, dated Sep. 2, 2016, 8 pages.
PCT International Search Report and Written Opinion received for PCT/US2017/047945, dated Oct. 20, 2017, 9 pages.
PCT International Search Report and Written Opinion received for PCT/US2018/055310, dated Jan. 29, 2019, 9 pages.
PCT International Search Report and Written Opinion received for PCT/US2019/044929, dated Nov. 20, 2019, 15 pages.
PCT International Search Report and Written Opinion received for PCT/US2019/052961, dated Dec. 10, 2019, 11 pages.
PCT International Search Report and Written Opinion received for PCT/US2019/069097 dated Dec. 10, 2019, 11 pages.
PCT International Search Report and Written Opinion received for PCT/US2020/050565, dated Dec. 22, 2020, 9 pages.
PCT International Search Report and Written Opinion received for PCT/US2021/035948, dated Oct. 26, 2021, 12 pages.
PCT International Search Report and Written Opinion received for PCT/US2022/011604, dated Mar. 25, 2022, 12 pages.
U.S. Appl. No. 15/437,699 of Jordan et al., filed Feb. 21, 2017.
U.S. Appl. No. 16/547,930 of Buist et al., filed Aug. 22, 2019.
U.S. Appl. No. 17/305,915 of Machatha et al., filed Jul. 16, 2021.

\* cited by examiner

PHARMACEUTICAL FORMULATIONS AND USES THEREOF

CROSS-REFERENCE TO RELATED APPLICATIONS

This application is a continuation of PCT International Application No. PCT/US2021/032335, filed May 13, 2021, which claims the benefit under 35 U.S.C. § 119(e) of U.S. Provisional Patent Application Ser. No. 63/024,193, filed on May 13, 2020. The entirety of each application is incorporated herein by reference thereto.

TECHNICAL FIELD

The present invention relates to pharmaceutical compositions and uses thereof comprising a quinoline compound, or pharmaceutically acceptable salt thereof, described herein. The present invention further relates to uses of such compositions, for example in treating, preventing, ameliorating, or lessening the severity of a disease, disorder, or condition.

BACKGROUND

The buildup or improper processing of toxic aldehyde species in the body underlies or is implicated in neurological, autoimmune, and inflammatory conditions, such as skin, lung, ocular, and systemic conditions. Metabolic and inflammatory processes in cells generate toxic aldehydes, such as malondialdehyde (MDA), 4-hydroxyl-2-nonenal (4-HNE), glyoxal, and methylglyoxal. These aldehydes are highly reactive with proteins, carbohydrates, lipids and DNA, leading to chemically modified biological molecules, activation of inflammatory mediators such as NF-kappa B, and damage in diverse organs. For example, retinaldehyde can react with phosphatidylethanolamine (PE) to form a highly toxic compound called A2E, which is a component of lipofuscin that is believed to be involved in the development and progression of Age-Related Macular Degeneration (AMD). Many bodily defense mechanisms function to remove or lower the levels of toxic aldehydes, including metabolism by aldehyde dehydrogenases, buffering by molecules such as glutathione (GSH) and removal from sites of potential toxicity by transporters such as ABCA4. Novel small molecule therapeutics can be used to scavenge "escaped" retinaldehyde in the retina, thus reducing A2E formation and lessening the risk of AMD (Jordan et al. (2006)).

Aldehydes are implicated in diverse pathological conditions such as dry eye, cataracts, keratoconus, Fuchs' endothelial dystrophy in the cornea, uveitis, allergic conjunctivitis, ocular cicatricial pemphigoid, conditions associated with photorefractive keratectomy (PRK) healing or other corneal healing, conditions associated with tear lipid degradation or lacrimal gland dysfunction, inflammatory ocular conditions such as ocular rosacea (with or without meibomian gland dysfunction), and non-ocular disorders or conditions such as skin cancer, psoriasis, contact dermatitis, atopic dermatitis, acne vulgaris, Sjögren-Larsson Syndrome, ischemic-reperfusion injury, inflammation, diabetes, neurodegeneration (e.g., Parkinson's disease), scleroderma, amyotrophic lateral sclerosis, autoimmune disorders (e.g., systemic lupus erythematosus [SLE] and rheumatoid arthritis), cardiovascular disorders (e.g., atherosclerosis), inflammatory bowel disease (e.g., Crohn's Disease and ulcerative colitis), non-alcoholic steatohepatitis (NASH), and conditions associated with the injurious effects of blister agents (Negre-Salvayre et al. (2008), Nakamura et al. (2007), Batista et al. (2012), Kenney et al. (2003), Int J Dermatol 43: 494 (2004), Invest Ophthalmol Vis Sci 48: 1552 (2007), Graefe's Clin Exp Ophthalmol 233: 694 (1994), Molecular Vision 18: 194 (2012)).

Thus, there remains a need for effective treatments for the varied disorders in which aldehyde toxicity is implicated.

SUMMARY

In one aspect, the present invention provides pharmaceutical compositions, formulations, and dosage forms comprising a quinoline compound, or a pharmaceutically acceptable salt thereof, described herein. In some embodiments of the present invention, the composition comprises a quinoline compound of general formula I:

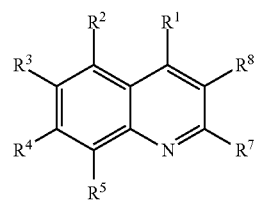

or a pharmaceutically acceptable salt thereof, wherein each variable is as defined herein.

In some embodiments, the quinoline compound is of the following structure:

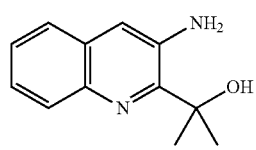

or a pharmaceutically acceptable salt thereof.

Unit dosage forms comprising a quinoline compound such as I-1 or a pharmaceutically acceptable salt thereof are suitable for administration to a patient for treating, ameliorating, or preventing a disease, disorder, or condition such as those described herein. Accordingly, in one aspect, the present invention provides a unit dosage form comprising a pharmaceutical composition comprising a disclosed quinoline compound, or a pharmaceutically acceptable salt thereof. In some embodiments, a unit dosage form of the invention comprises about 5 mg to about 400 mg of the quinoline compound such as I-1, or a pharmaceutically acceptable salt thereof. In some embodiments, a unit dosage form of the invention is suitable for oral administration. In some embodiments, a unit dosage form of the invention comprises one or more pharmaceutically acceptable excipients or carriers. In some embodiments, the one or more pharmaceutically acceptable excipients or carriers are selected from one or more of Eudragit L100, microcrystalline cellulose, lactose monohydrate, croscarmellose sodium, crospovidone (Kollidon CL), a vinylpyrrolidone-vinyl acetate copolymer such as Kollidon VA64, sodium lauryl sulfate, and magnesium stearate. In some embodiments, a unit dosage form of the invention exhibits pharmacokinetics results as described herein.

In another aspect, the present invention provides a method for reducing levels of one or more toxic aldehydes in a subject, comprising administering to a subject in need thereof a pharmaceutical composition, as described herein.

In some embodiments, the toxic aldehyde is selected from formaldehyde, acetaldehyde, acrolein, glyoxal, methylglyoxal, hexadecanal, octadecanal, hexadecenal, succinic semialdehyde, malondialdehyde, 4-hydroxynonenal, 4-hydroxy-2E-hexenal, 4-hydroxy-2E,6Z-dodecadienal, retinaldehyde, leukotriene B4 aldehyde, and octadecenal.

In some embodiments, the toxic aldehyde is formaldehyde. In some embodiments, the toxic aldehyde is acetaldehyde. In some embodiments, the toxic aldehyde is acrolein. In some embodiments, the toxic aldehyde is glyoxal. In some embodiments, the toxic aldehyde is methylglyoxal. In some embodiments, the toxic aldehyde is hexadecanal. In some embodiments, the toxic aldehyde is octadecanal. In some embodiments, the toxic aldehyde is hexadecenal. In some embodiments, the toxic aldehyde is succinic semialdehyde (SSA). In some embodiments, the toxic aldehyde is malondialdehyde (MDA). In some embodiments, the toxic aldehyde is 4-hydroxynonenal. In some embodiments, the toxic aldehyde is retinaldehyde. In some embodiments, the toxic aldehyde is 4-hydroxy-2E-hexenal. In some embodiments, the toxic aldehyde is 4-hydroxy-2E,6Z-dodecadienal. In some embodiments, the aldehyde is leukotriene B4 aldehyde. In some embodiments, the aldehyde is octadecenal.

In another aspect, the present invention provides a method for treating a disease, disorder, or condition described herein, comprising administering a pharmaceutical composition to a subject in need thereof, as described herein.

In some embodiments, the disease, disorder, or condition is an inflammatory condition. In some embodiments, the inflammatory disorder is systemic. In some embodiments, the inflammatory disorder is localized to a particular tissue or organ.

In some embodiments, the disease, disorder or condition for treatment with the compounds of the disclosure is fatty liver. In some embodiments, the disease, disorder or condition for treatment with the compounds of the disclosure is non-alcoholic fatty liver disease (NAFLD), non-alcoholic steatohepatitis (NASH), inflammatory bowel disease, Crohn's disease, ulcerative colitis (UC), psoriasis, IBS (irritable bowel syndrome or spastic colon), ankylosing spondylitis, osteoporosis, rheumatoid arthritis (RA), psoriatic arthritis, chronic obstructive pulmonary disease (COPD), atherosclerosis, pulmonary arterial hypertension, pyridoxine-dependent epilepsy, atopic dermatitis, atopic eczema, rosacea, multiple sclerosis (MS), systemic lupus erythematosus (SLE), lupus nephritis, sepsis, eosinophilic esophagitis, chronic kidney disease (CKD), fibrotic renal disease, chronic eosinophilic pneumonia, extrinsic allergic alveolitis, pre-eclampsia, endometriosis, polycystic ovary syndrome (PCOS), reduced female fertility, reduced sperm viability and motility, or cyclophosphamide-induced hemorrhagic cystitis.

In some embodiments, the disease, disorder, or condition for treatment with the compounds of the disclosure is lung-based chronic obstructive pulmonary disease (COPD), interstitial lung disease (ILD), idiopathic pulmonary fibrosis (IPF), cystic fibrosis (CF), emphysema due to alpha-1 antitrypsin deficiency, or pulmonary arterial hypertension (PAH).

In some embodiments, the disease, disorder, or condition for treatment with the compounds of the disclosure is light chain deposition disease, IgA nephropathy, end stage renal disease, gout, pseudogout, diabetic nephropathy, diabetic neuropathy, traumatic brain injury, noise-induced hearing loss, Alzheimer's Disease, Parkinson's Disease, Huntington Disease, amyotrophic lateral sclerosis, primary biliary cirrhosis, primary sclerosing cholangitis, uterine leiomyoma, sarcoidosis, or chronic kidney disease.

In some embodiments, the disease, disorder, or condition for treatment with the compounds of the disclosure is an ocular inflammatory disorder. In some embodiments, the ocular inflammatory disorder is diabetic macular edema (DME), atopic keratoconjunctivitis (AKC), vernal keratoconjunctivitis (VKC), age-related macular degeneration (AMD), dry eye disease (DED), allergic conjunctivitis (AC), dry eye disease with allergic conjunctivitis, noninfectious anterior uveitis, posterior uveitis, pan-uveitis, post-surgical ocular pain and inflammation. In some embodiments, the disease, disorder, or condition is neurotrophic keratitis. In some embodiments, the disease, disorder, or condition is corneal graft vs. host disease. In some embodiments, the disease, disorder, or condition is scleritis.

In some embodiments, the disease, disorder, or condition is chronic cough. In some embodiments, the disease, disorder, or condition is pneumonia. In some embodiments, the disease, disorder, or condition is asthma. In some embodiments, the disease, disorder, or condition is atopic asthma. In some embodiments, the disease, disorder, or condition is allergic asthma. In some embodiments, the disease, disorder, or condition is allergic rhinitis. In some embodiments, the disease, disorder, or condition is sinusitis. In some embodiments, the disease, disorder, or condition is hay fever.

In some embodiments, the atopic (or allergic) asthma is triggered by an allergen such as an indoor, outdoor, or occupational allergen, including pollen, dust, an animal (e.g., cat dander or dog hair), or dust mites. In some embodiments, the atopic asthma patient also has another condition selected from seasonal allergies, eczema, and a food allergy.

In some embodiments, the disease, disorder, or condition is pulmonary sepsis. In some embodiments, the disease, disorder, or condition is sepsis or septic shock. In some embodiments, the disease, disorder, or condition is keratitis. In some embodiments, the disease, disorder, or condition is graft vs. host disease, such as graft vs. host disease after a corneal or organ transplant. In some embodiments, the disease, disorder, or condition is arthritis, osteoarthritis, or rheumatoid arthritis. In some embodiments, the disease, disorder, or condition is multiple sclerosis. In some embodiments, the disease, disorder, or condition is amyotrophic lateral sclerosis. In some embodiments, the disease, disorder, or condition is Alzheimer's disease. In some embodiments, the disease, disorder, or condition is Huntington's disease. In some embodiments, the disease, disorder, or condition is Parkinson's disease. In some embodiments, the disease, disorder, or condition is fibrosis.

In some embodiments, the disease, disorder, or condition is alcohol induced hepatitis. In some embodiments, the disease, disorder, or condition is minimal change disease. In some embodiments, the disease, disorder, or condition is focal segmental glomerulosclerosis.

In some embodiments, the disease, disorder, or condition is acute respiratory distress syndrome (ARDS). In some embodiments, the ARDS is associated with a viral infection.

In some embodiments, the disease, disorder, or condition is a viral infection, such as SARS-CoV2.

In some embodiments, the disease, disorder, or condition is atopic dermatitis. In some embodiments, the disease, disorder, or condition is atopic eczema. In some embodiments, the disease, disorder, or condition is psoriasis.

In some embodiments, the disease, disorder, or condition is diabetic macular edema. In some embodiments, the disease, disorder, or condition is Stargardt's disease.

In some embodiments, the disease, disorder, or condition is keratitis. In some embodiments, the disease, disorder, or condition is neurotrophic keratitis. In some embodiments, the disease, disorder, or condition is scleritis.

In some embodiments, the unit dosage form is administered systemically.

In some embodiments, the unit dosage form is administered orally.

In some embodiments, the pharmaceutical composition is a liquid. In some embodiments, the pharmaceutical composition is administered as a liquid via nasogastric tube.

BRIEF DESCRIPTIONS OF THE DRAWINGS

Figure 5:
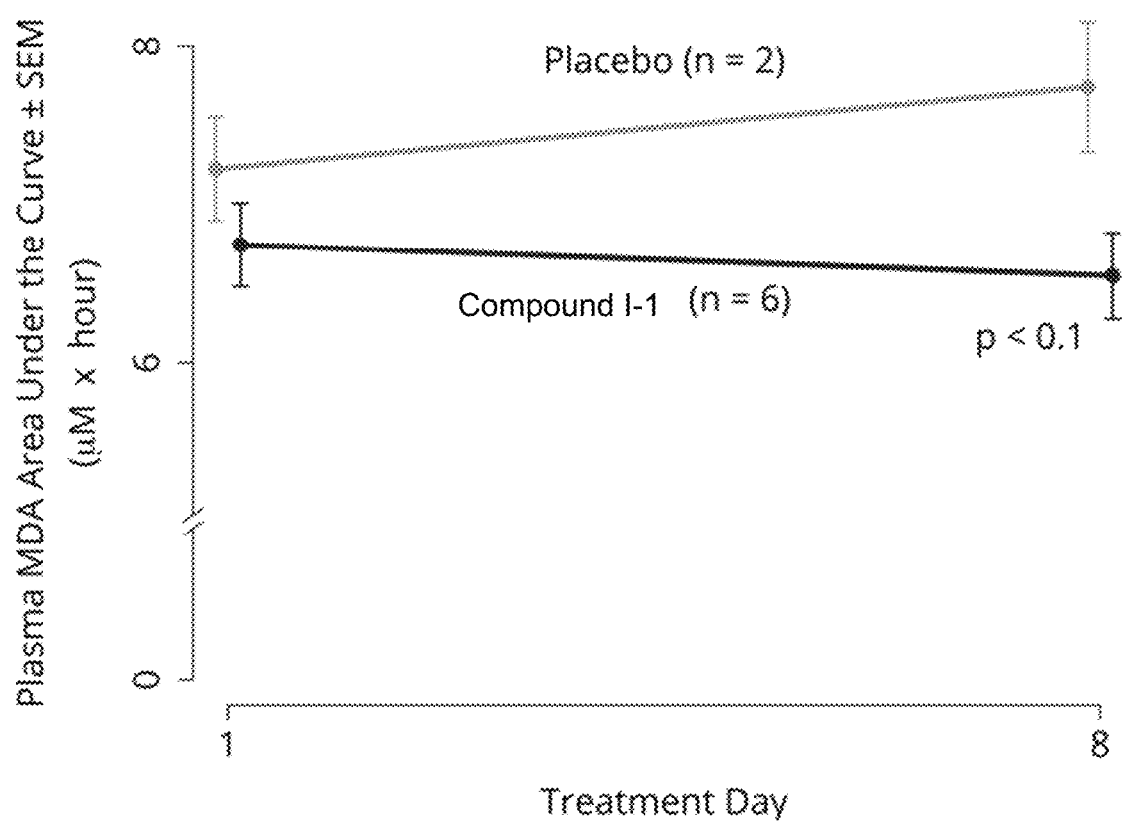

FIG. 5 shows area under the curve (AUC) of malondialdehyde (MDA) on day 1 and day 8 in plasma of human subjects administered I-1 orally in a Phase 1 trial. At the top dose (600 mg BID), a Cmax of 1700 ng/mL (approximately 8.5 mM) and an $AUC_{0-12}$ of 7220 h*ng/mL were observed.

Figure 6:
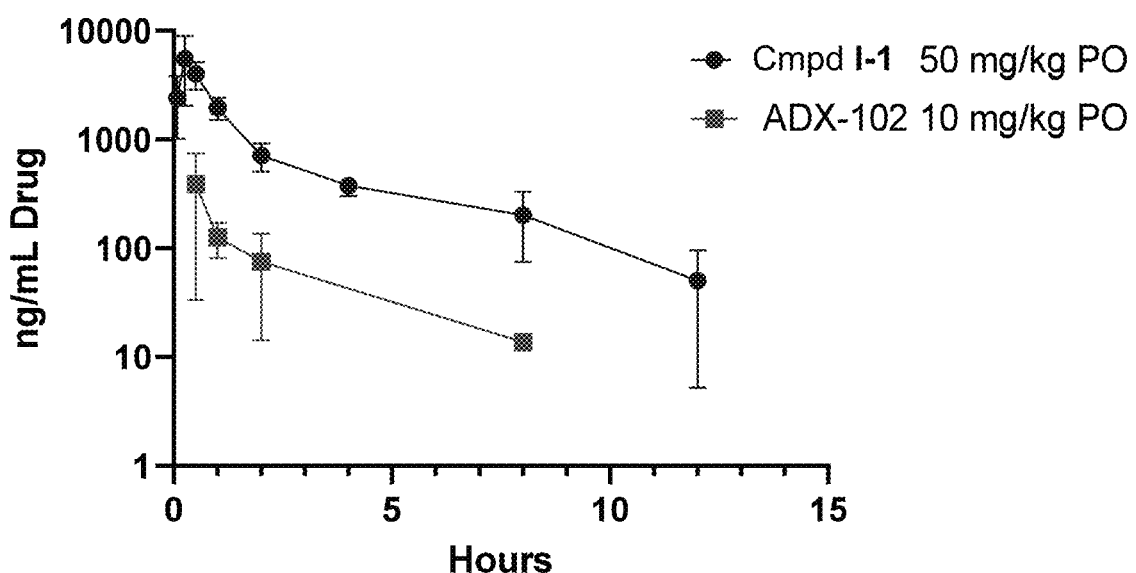

FIG. 6 shows the pharmacokinetic profiles of PO-dosed compound I-1 and ADX-102 (reproxalap) in Sprague-Dawley rats. The 10 mg/kg data for reproxalap is multiplied by five for comparison purposes since compound I-1 was dosed at 50 mg/kg.

Figure 7:
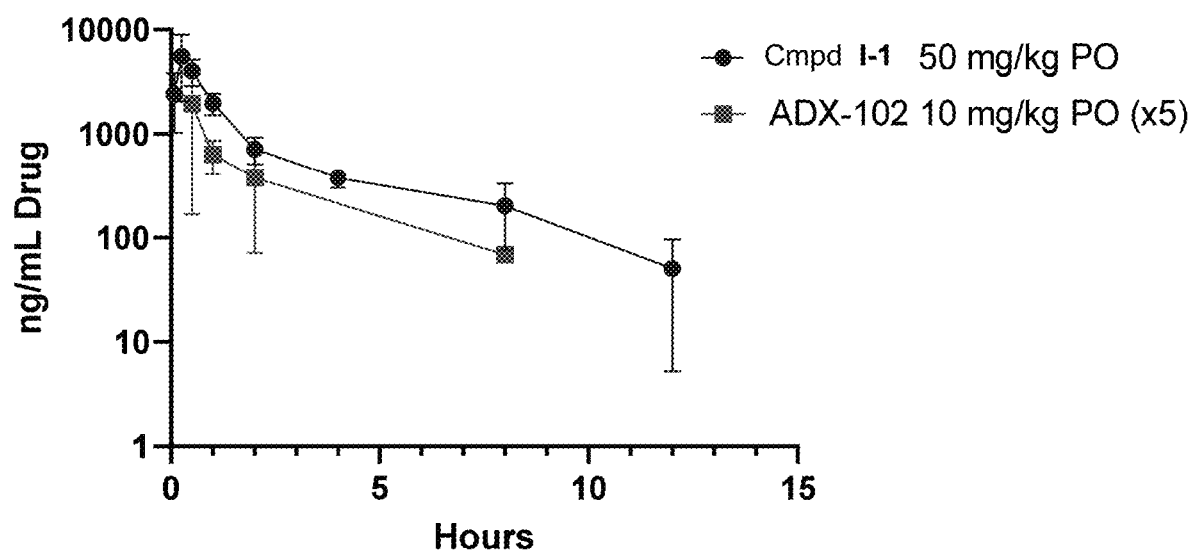

FIG. 7 shows the dose-normalized pharmacokinetic profiles of PO-dosed compound I-1 and ADX-102 (reproxalap) in Sprague-Dawley rats.

DETAILED DESCRIPTION

1. General Description of Certain Aspects of the Invention

In some aspects, the present disclosure provides pharmaceutical compositions, formulations, and unit dosage forms comprising a quinoline compound, or a pharmaceutically acceptable salt thereof, described herein. In some embodiments, the pharmaceutical composition is suitable for oral administration. In some embodiments, the unit dosage form is suitable for oral administration. In some embodiments, the unit dosage form is a capsule or tablet for oral administration. In some aspects, the present disclosure provides compounds, compositions, and methods for the treatment, amelioration, prevention, and/or reduction of a risk of a disease, disorder, or condition such as those described herein.

In one aspect, the present disclosure provides a pharmaceutical composition comprising a compound of Formula I.

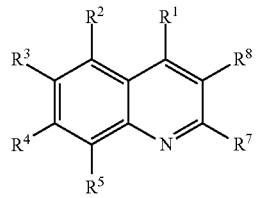

or a pharmaceutically acceptable salt thereof, wherein:
each of $R^1$, $R^7$, and $R^8$ is independently H, D, halogen, —$NH_2$, —CN, —OR, —SR, optionally substituted $C_{1-6}$ aliphatic, or

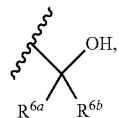

wherein one of $R^1$, $R^7$, and $R^8$ is —$NH_2$ and one of $R^1$ $R^7$, and $R^8$ is

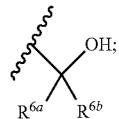

$R^2$ is selected from —R, halogen, —CN, —OR, —SR, —$N(R)_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^3$ is selected from —R, halogen, —CN, —OR, —SR, —$N(R)_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^4$ is selected from —R, halogen, —CN, —OR, —SR, —$N(R)_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^5$ is selected from —R, halogen, —CN, —OR, —SR, —$N(R)_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^{6a}$ is $C_{1-4}$ aliphatic optionally substituted with 1, 2, or 3 deuterium or halogen atoms;

$R^{6b}$ is $C_{1-4}$ aliphatic optionally substituted with 1, 2, or 3 deuterium or halogen atoms; or $R^{6a}$ and $R^{6b}$, taken together with the carbon atom to which they are attached, form a 3- to 8-membered cycloalkyl or heterocyclyl ring containing 1-2 heteroatoms selected from nitrogen, oxygen, and sulfur; and each R is independently selected from hydrogen, deuterium, and an optionally substituted group selected from $C_{1-6}$ aliphatic; a 3- to 8-membered saturated or partially unsaturated monocyclic carbocyclic ring; phenyl; an 8- to 10-membered bicyclic aryl ring; a 3- to 8-membered saturated or partially unsaturated monocyclic heterocyclic ring having 1-4 heteroatoms independently selected from nitrogen, oxygen, and sulfur; a 5- to 6-membered monocyclic heteroaryl ring having 1-4 heteroatoms independently selected from nitrogen, oxygen, and sulfur; a 6- to 10-membered bicyclic saturated or partially unsaturated heterocyclic ring having 1-5 heteroatoms independently selected from nitrogen, oxygen, and sulfur; and a 7- to 10-membered bicyclic heteroaryl ring having 1-5 heteroatoms independently selected from nitrogen, oxygen, and sulfur; and a pharmaceutically acceptable excipient or carrier.

In another aspect, the present disclosure provides a pharmaceutical composition comprising a compound of formula II:

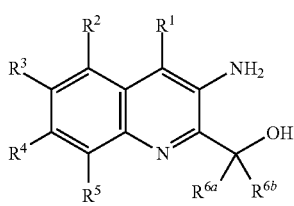

or a pharmaceutically acceptable salt thereof, wherein:
$R^1$ is H, D, or halogen;
$R^2$ is H, D, or halogen;
$R^3$ is H, D, or halogen;
$R^4$ is H, D, or halogen;
$R^5$ is H, D, or halogen;
$R^{6a}$ is $C_{1-4}$ aliphatic optionally substituted with 1, 2, or 3 deuterium or halogen atoms; and
$R^{6b}$ is $C_{1-4}$ aliphatic optionally substituted with 1, 2, or 3 deuterium or halogen atoms; and a pharmaceutically acceptable excipient or carrier.

2. Definitions

Compounds of the present invention include those described generally above, and are further illustrated by the classes, subclasses, and species disclosed herein. As used herein, the following definitions shall apply unless otherwise indicated. For purposes of the present disclosure, the chemical elements are identified in accordance with the Periodic Table of the Elements, CAS version, *Handbook of Chemistry and Physics*, 75th Ed. Additionally, general principles of organic chemistry are described in *Organic Chemistry*, Thomas Sorrell, University Science Books, Sausalito: 1999, and *March's Advanced Organic Chemistry*, 5th Ed., Ed.: Smith, M. B. and March, J., John Wiley & Sons, New York: 2001, the entire contents of which are hereby incorporated by reference.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In some embodiments, the term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. In certain embodiments of the compounds, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned for the compounds herein are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen, —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —($C_{1-4}$ straight or branched alkylene)O—$N(R°)_2$; or —($C_{1-4}$ straight or branched alkylene)C(O)O—$N(R°)_2$, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, and sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, and a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, and an unsubstituted 5- to 6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, and an unsubstituted 5 to 6-membered saturated, partially unsaturated, or aryl ring having 0-4 heteroatoms independently selected from nitrogen, oxygen, and sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, and sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5- to 6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3- to 12-membered saturated, partially unsaturated, or aryl mono- or bicyclic ring having 0-4 heteroatoms independently selected from nitrogen, oxygen, and sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, and sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, mesylate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Serum pharmacokinetic parameters can be computed using WinNonlin Version 3.2 (Pharsight®, Mountain View, CA) using standard non-compartmental or compartmental methods. As used herein, the term "Cmax" refers to the maximum observed serum concentration of test compound estimated directly from concentration versus time data. As used herein, the term "Tmax" refers to the time of the first occurrence of Cmax. As used herein, the term "AUC(0-tlast)" refers to the area under the serum concentration vs. time curve from time 0 to T$_{last}$ (the time of the last quantifiable concentration estimated using the linear/log trapezoidal approximation). The terminal elimination rate constant (kel) may be estimated using linear least-square regression analysis of the serum concentration-time data obtained during the terminal log-linear phase. As used herein, the term "AUC(0-inf)" refers to AUC(0-tlast) extrapolated to infinity, which is calculated as the sum of AUC(0-tlast) and Cest/kel, wherein Cest is the predicted plasma concentration obtained from the log linear regression analysis at the last quantifiable time point. As used herein, the term "t½" refers to terminal phase half-life calculated as ln(2)/kel. As used herein, the term "AUC(last-inf)" refers to the area under the serum concentration versus time curve from $T_{last}$ to infinity, which is estimated as Cpest/kel, wherein Cpest represented the estimated concentration at time $T_{last}$ based on the aforementioned regression analysis. As used herein, the term "AUCτ" refers to the area under the serum concentration versus time curve over the dosing interval. As used herein, the term "Rac" refers to the accumulation ratio of test compound in the serum, which is calculated as a measure of drug accumulation at steady state compared to Day 1.

Urine pharmacokinetic parameters can be used to assess the amount of parent drug excreted unchanged in the urine. The urine pharmacokinetic parameters can be calculated under the assumption that the amount of test compound excreted unchanged in the urine over the dosing interval was at steady state on the last day of dosing during a given oral administration period. As used herein, the term "$A_E$" refers to the amount of parent drug excreted from 0-12 hours post dose on the final day of oral dosing, calculated by (Urine Compound Concentration×Urine Volume). As used herein, the term "$A_E$/Dose" refers to percent of Dose renally excreted unchanged on final day of oral dosing, calculated by ($A_E$/Dose)×100. As used herein, the term "$CL_R$" refers to renal clearance on the final day of oral dosing, calculated by ($A_E$/AUCτ). As used herein, the term "$CL_R$/Fu" refers to renal clearance of unbound drug, calculated by ($CL_R$/Fu), where the fraction of drug in the serum not bound to proteins (Fu) is determined from in vitro human serum protein binding data.

As used herein, the terms "fasting state," "fasting condition," "fasted state," or "fasted condition," refer to a state or condition following at least about 8 hour fast from all food and drink (except water). In some embodiments, a subject is to fast from all food and drink (except water) for at least 8 hours prior to receiving dosing in the morning, and continue to fast until lunch.

As used herein, the terms "fed state" or "fed condition" refer to a state or condition following a standardized high-fat meal. In some embodiments, an administration in a fed state refers to an administration following a standard FDA high-fat breakfast. In some embodiments, subjects receiving the fed regimen fast from all food and drink (except water) for at least 8 hours prior to receiving a test meal. In some embodiments, prior to dosing on Day 1, subjects are served a standard FDA high-fat breakfast composed of 2 eggs fried in butter, 2 strips of bacon, 2 slices of toast with 2 pats of butter, 4 ounces of hash browns and 8 ounces of whole milk, to be ingested and completely consumed within 20 minutes. This breakfast contains approximately 150 protein kcal, 250 carbohydrate kcal, and 500-600 fat kcal. In some embodiments, an alternative meal may be given provided the meal has similar composition and caloric contents.

As used herein, "about" or "approximately" in reference to a numerical value means that the stated numerical value may vary by up to 10% of the stated value. For example, "about 10" refers to a value of 9.9 to 10.1 (10+/−0.1).

3. Detailed Description of Embodiments

The compounds described herein are quinoline compounds that have aldehyde trapping activity, and have been described for use in treating disorders and diseases associated with the effects of toxic aldehydes. See, e.g., PCT patent publication WO2006127945, WO2014116836, WO2017035077, and WO2017035082, each of which is hereby incorporated by reference. Synthesis of the compounds herein are described in PCT publications WO2006127945, WO2017035082, and WO2018039192; and U.S. patent application publication US 2013/0190500, each of which is hereby incorporated by reference. As described in the present disclosure, certain quinoline compounds are useful in treating a disease, disorder, or condition described herein.

In addition, the disclosures of the following patent applications are hereby incorporated by reference: WO 2019/075136, filed Oct. 10, 2018; and PCT/US2021/023884, filed Mar. 24, 2021. These applications provide additional disclosure related to the quinoline compounds described herein, including their use in treating certain diseases.

In some embodiments, compound I-1 is selected as the active pharmaceutical ingredient and is processed and manufactured to a solid form thereof, such as its most stable polymorph, prior to compounding into drug product. In some embodiments, the solid form, e.g., polymorph, is one of those described in PCT/US2020/031138, published as WO 2020/223685, hereby incorporated by reference.

Accordingly, in one aspect, the present disclosure provides a pharmaceutical composition comprising a compound of Formula I:

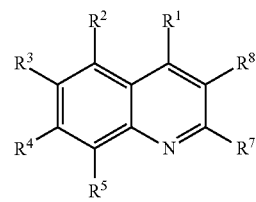

I or a pharmaceutically acceptable salt thereof, wherein:
    each of $R^1$, $R^7$, and $R^8$ is independently H, D, halogen, —NH₂, —CN, —OR, —SR, optionally substituted $C_{1-6}$ aliphatic, or

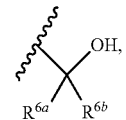

wherein one of $R^1$, $R^7$, and $R^8$ is —NH₂ and one of $R^1$, $R^7$, and $R^8$ is

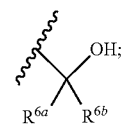

$R^2$ is selected from —R, halogen, —CN, —OR, —SR, —N(R)₂, —N(R)C(O)R, —C(O)N(R)₂, —N(R)C(O)N(R)₂, —N(R)C(O)OR, —OC(O)N(R)₂, —N(R)S(O)₂R, —SO₂N(R)₂, —C(O)R, —C(O)OR, —OC(O)R, —S(O)R, and —S(O)₂R;

$R^3$ is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^4$ is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^5$ is selected from —R, halogen, —CN, —OR, —SR, —N(R)$_2$, —N(R)C(O)R, —C(O)N(R)$_2$, —N(R)C(O)N(R)$_2$, —N(R)C(O)OR, —OC(O)N(R)$_2$, —N(R)S(O)$_2$R, —SO$_2$N(R)$_2$, —C(O)R, —C(O)OR, —OC(O)R, —S(O)R, and —S(O)$_2$R;

$R^{6a}$ is $C_{1-4}$ aliphatic optionally substituted with 1, 2, or 3 deuterium or halogen atoms;

$R^{6b}$ is $C_{1-4}$ aliphatic optionally substituted with 1, 2, or 3 deuterium or halogen atoms; or $R^{6a}$ and $R^{6b}$, taken together with the carbon atom to which they are attached, form a 3- to 8-membered cycloalkyl or heterocyclyl ring containing 1-2 heteroatoms selected from nitrogen, oxygen, and sulfur; and each R is independently selected from hydrogen, deuterium, and an optionally substituted group selected from $C_{1-6}$ aliphatic; a 3- to 8-membered saturated or partially unsaturated monocyclic carbocyclic ring; phenyl; an 8- to 10-membered bicyclic aryl ring; a 3- to 8-membered saturated or partially unsaturated monocyclic heterocyclic ring having 1-4 heteroatoms independently selected from nitrogen, oxygen, and sulfur; a 5- to 6-membered monocyclic heteroaryl ring having 1-4 heteroatoms independently selected from nitrogen, oxygen, and sulfur; a 6- to 10-membered bicyclic saturated or partially unsaturated heterocyclic ring having 1-5 heteroatoms independently selected from nitrogen, oxygen, and sulfur; and a 7- to 10-membered bicyclic heteroaryl ring having 1-5 heteroatoms independently selected from nitrogen, oxygen, and sulfur; and a pharmaceutically acceptable excipient or carrier.

In another aspect, the present disclosure provides a pharmaceutical composition comprising a compound of Formula II:

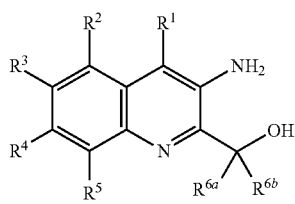

II or a pharmaceutically acceptable salt thereof, wherein:
$R^1$ is H, D, or halogen;
$R^2$ is H, D, or halogen;
$R^3$ is H, D, or halogen;
$R^4$ is H, D, or halogen;
$R^5$ is H, D, or halogen;
$R^{6a}$ is $C_{1-4}$ aliphatic optionally substituted with 1, 2, or 3 deuterium or halogen atoms; and
$R^{6b}$ is $C_{1-4}$ aliphatic optionally substituted with 1, 2, or 3 deuterium or halogen atoms; and a pharmaceutically acceptable excipient or carrier.

The following embodiments are applicable to Formula I.

In some embodiments of Formula I, $R^{6a}$ is $C_{1-4}$ aliphatic. In some embodiments, $R^{6a}$ is $C_{1-4}$ aliphatic optionally substituted with 1, 2, or 3 deuterium atoms. In some embodiments, $R^{6a}$ is $C_{1-4}$ aliphatic optionally substituted with 1, 2, or 3 halogen atoms.

In some embodiments of Formula I, $R^{6a}$ is $C_{1-4}$ alkyl. In some embodiments, $R^{6a}$ is $C_{1-4}$ alkyl optionally substituted with 1, 2, or 3 deuterium or halogen atoms. In some embodiments, $R^{6a}$ is $C_{1-4}$ alkyl optionally substituted with 1, 2, or 3 halogen atoms. In some embodiments, $R^{6a}$ is methyl or ethyl optionally substituted with 1, 2, or 3 halogen atoms. In some embodiments, $R^{6a}$ is methyl.

As defined generally above, $R^{6b}$ is $C_{1-4}$ aliphatic optionally substituted with 1, 2, or 3 deuterium or halogen atoms.

In some embodiments of Formula I, $R^{6b}$ is $C_{1-4}$ aliphatic. In some embodiments, $R^{6b}$ is $C_{1-4}$ aliphatic optionally substituted with 1, 2, or 3 deuterium atoms. In some embodiments, $R^{6b}$ is $C_{1-4}$ aliphatic optionally substituted with 1, 2, or 3 halogen atoms.

In some embodiments of Formula I, $R^{6b}$ is $C_{1-4}$ alkyl. In some embodiments, $R^{6b}$ is $C_{1-4}$ alkyl optionally substituted with 1, 2, or 3 deuterium or halogen atoms. In some embodiments, $R^{6b}$ is $C_{1-4}$ alkyl optionally substituted with 1, 2, or 3 halogen atoms. In some embodiments, $R^{6b}$ is methyl or ethyl optionally substituted with 1, 2, or 3 halogen atoms. In some embodiments, $R^{6b}$ is methyl.

As defined generally above, in some embodiments, $R^{6a}$ and $R^{6b}$, taken together with the carbon atom to which they are attached, form a 3- to 8-membered cycloalkyl or heterocyclyl ring containing 1-2 heteroatoms selected from nitrogen, oxygen, and sulfur.

In some embodiments of Formula I, $R^{6a}$ and $R^{6b}$, taken together with the carbon atom to which they are attached, form a 3- to 8-membered cycloalkyl. In some embodiments, $R^{6a}$ and $R^{6b}$, taken together with the carbon atom to which they are attached, form a 3- to 8-membered heterocyclyl ring containing 1-2 heteroatoms selected from nitrogen, oxygen, and sulfur.

In some embodiments of Formula I, $R^{6a}$ and $R^{6b}$, taken together with the carbon atom to which they are attached, form a cyclopropyl, cyclobutyl, or cyclopentyl ring. In some embodiments, $R^{6a}$ and $R^{6b}$, taken together with the carbon atom to which they are attached, form an oxirane, oxetane, tetrahydrofuran, or aziridine.

In some embodiments of Formula I, the —NH$_2$ on one of $R^1$, $R^7$, and $R^8$ and the carbinol on the other of $R^1$, $R^7$, and $R^8$ are on adjacent carbon atoms of the pyridine moiety.

In some embodiments, the compound is a compound of Formula I-a, I-b, or I-c:

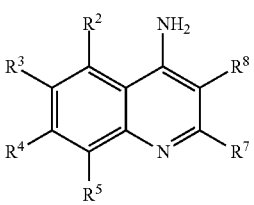

I-a

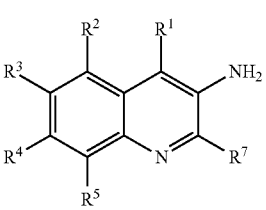

I-b

-continued

I-c

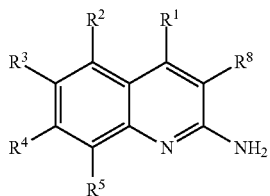

or a pharmaceutically acceptable salt thereof, wherein:
each of $R^1$, $R^7$, and $R^8$ when present is independently H, D, halogen, —CN, —OR, —SR, optionally substituted $C_{1-6}$ aliphatic, or

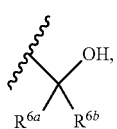

wherein one of $R^1$, $R^7$, and $R^8$ is

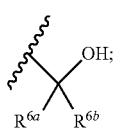

and
$R^2$, $R^3$, $R^4$, $R^5$, $R^{6a}$, $R^{6b}$, $R^7$, $R^8$, and R are as defined for Formula I.

In some embodiments, the compound for use in the method is a compound of Formula I-d, I-e, I-f or I-g:

I-d

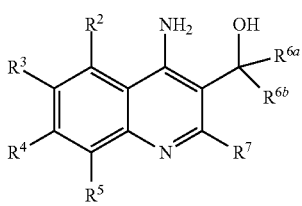

I-e

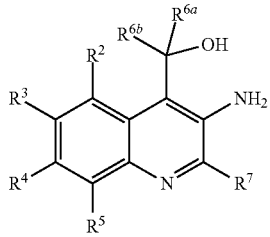

I-f

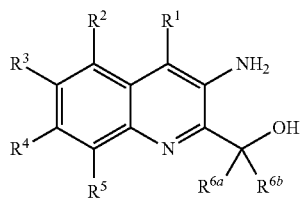

-continued

I-g

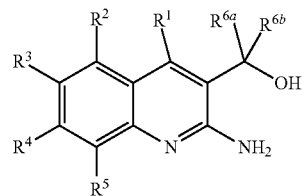

or a pharmaceutically acceptable salt thereof, wherein;
$R^1$ and $R^7$ is independently H, D, halogen, —CN, —OR, —SR, optionally substituted $C_{1-6}$ aliphatic; and
$R^2$, $R^3$, $R^4$, $R^5$, $R^{6a}$, $R^{6b}$, $R^7$, $R^8$, and R are as defined for Formula I.

The following embodiments are applicable to Formula II.
As defined generally above, $R^1$ is H, D, or halogen.
In some embodiments, $R^1$ is H. In some embodiments, $R^1$ is D. In some embodiments, $R^1$ is halogen. In some embodiments, $R^1$ is Cl. In some embodiments, $R^1$ is Br.
As defined generally above, $R^2$ is H, D, or halogen.
In some embodiments, $R^2$ is H. In some embodiments, $R^2$ is D. In some embodiments, $R^2$ is halogen. In some embodiments, $R^2$ is Cl. In some embodiments, $R^2$ is Br.
As defined generally above, $R^3$ is H, D, or halogen.
In some embodiments, $R^3$ is H. In some embodiments, $R^3$ is D. In some embodiments, $R^3$ is halogen. In some embodiments, $R^3$ is Cl. In some embodiments, $R^3$ is Br.
As defined generally above, $R^4$ is H, D, or halogen.
In some embodiments, $R^4$ is H. In some embodiments, $R^4$ is D. In some embodiments, $R^4$ is halogen. In some embodiments, $R^4$ is Cl. In some embodiments, $R^4$ is Br.
As defined generally above, $R^5$ is H, D, or halogen.
In some embodiments, $R^5$ is H. In some embodiments, $R^5$ is D. In some embodiments, $R^5$ is halogen. In some embodiments, $R^5$ is Cl. In some embodiments, $R^5$ is Br.
As defined generally above, $R^{6a}$ is $C_{1-4}$ aliphatic optionally substituted with 1, 2, or 3 deuterium or halogen atoms.
In some embodiments, $R^{6a}$ is $C_{1-4}$ aliphatic substituted with 1, 2, or 3 deuterium or halogen atoms. In some embodiments, $R^{6a}$ is $C_{1-4}$ aliphatic. In some embodiments, $R^{6a}$ is $C_{1-4}$ alkyl. In some embodiments, $R^{6a}$ is methyl, ethyl, n-propyl, or isopropyl. In some embodiments, $R^{6a}$ is methyl.
As defined generally above, $R^{6b}$ is $C_{1-4}$ aliphatic optionally substituted with 1, 2, or 3 deuterium or halogen atoms.
In some embodiments, $R^{6b}$ is $C_{1-4}$ aliphatic substituted with 1, 2, or 3 deuterium or halogen atoms. In some embodiments, $R^{6b}$ is $C_{1-4}$ aliphatic. In some embodiments, $R^{6b}$ is $C_{1-4}$ alkyl. In some embodiments, $R^{6b}$ is $C_{1-4}$ alkyl optionally substituted with 1, 2, or 3 fluorine atoms. In some embodiments, $R^{6b}$ is methyl, ethyl, n-propyl, or isopropyl. In some embodiments, $R^{6b}$ is methyl.
In some embodiments, $R^{6a}$ and $R^{6b}$ are methyl or ethyl. In some embodiments, $R^{6a}$ and $R^{6b}$ are methyl. In some embodiments, $R^{6a}$ and $R^{6b}$ are —$CD_3$.
In some embodiments, the compound is of Formula II-a:

II-a

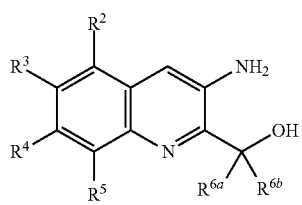

or a pharmaceutically acceptable salt thereof, wherein:
each of $R^2$, $R^3$, $R^4$, $R^5$, $R^{6a}$, and $R^{6b}$ is as defined as provided above and described in embodiments herein, both singly and in combination.

In some embodiments, the compound is of Formula II-b:

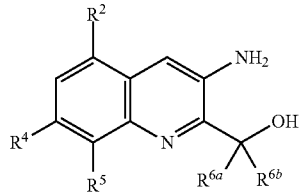

II-b or a pharmaceutically acceptable salt thereof, wherein:
each of $R^2$, $R^4$, $R^5$, $R^{6a}$, and $R^{6b}$ is as defined as provided above and described in embodiments herein, both singly and in combination.

In some embodiments, the compound is of any one of Formulae II-c, II-d, II-e, or II-f:

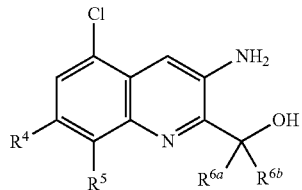

II-c

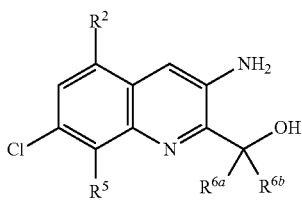

II-d

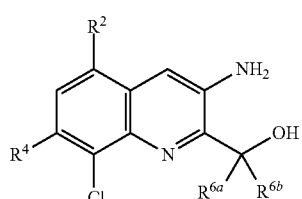

II-e

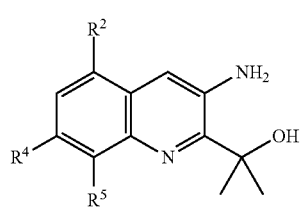

II-f or a pharmaceutically acceptable salt thereof, wherein:
each of $R^2$, $R^4$, $R^5$, $R^{6a}$, and $R^{6b}$ is as defined as provided above and described in embodiments herein, both singly and in combination.

In some embodiments, the compound is of Formula II-g:

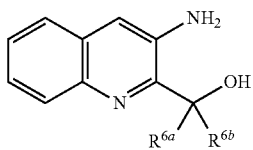

II-g or a pharmaceutically acceptable salt thereof, wherein:
each of $R^{6a}$ and $R^{6b}$ is as defined as provided above and described in embodiments herein, both singly and in combination.

In some embodiments, a disclosed pharmaceutical composition comprises a compound selected from one depicted in Table 1, below.

TABLE 1

Representative Compounds

| | |
|---|---|
| 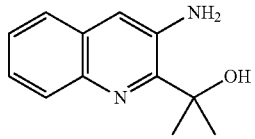 | I-1 |
| 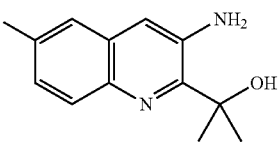 | I-2 |
| 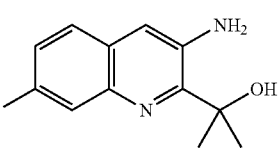 | I-3 |
| 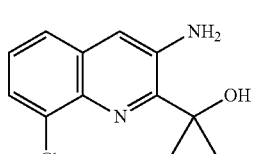 | I-4 |
| 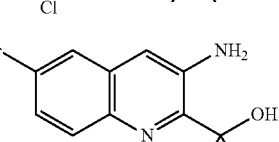 | I-5 |
| 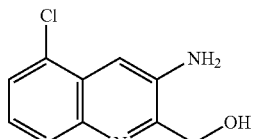 | I-6 |
| 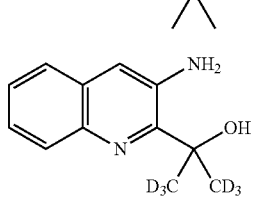 | I-7 |

TABLE 1-continued
Representative Compounds
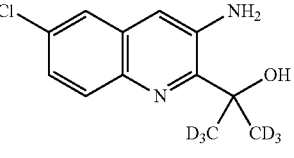 I-8
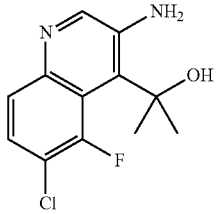 [SMILES: CC(C)(O)c1c(N)cnc2ccc(Cl)c(F)c12] I-9
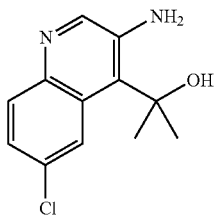 [SMILES: CC(C)(O)c1c(N)cnc2ccc(Cl)cc12] I-10
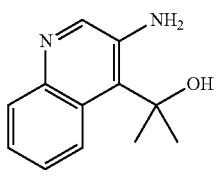 I-11
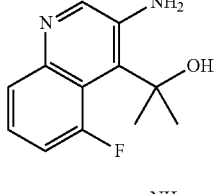 I-12
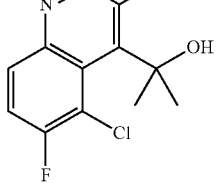 I-13
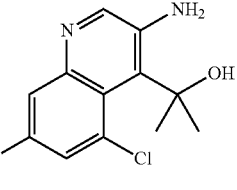 I-14
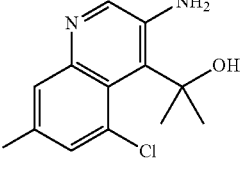 I-15
TABLE 1-continued
Representative Compounds
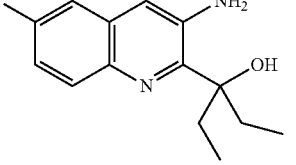 I-16
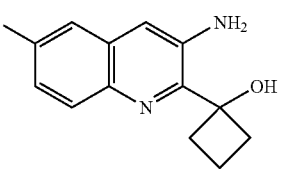 I-17
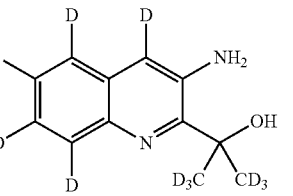 X-1
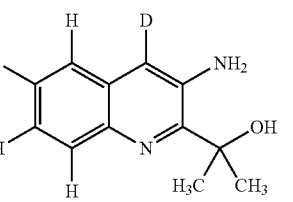 X-2
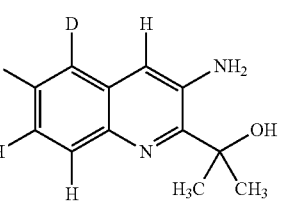 X-3
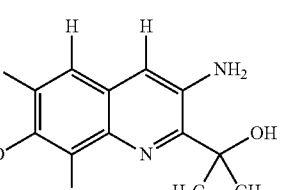 X-4
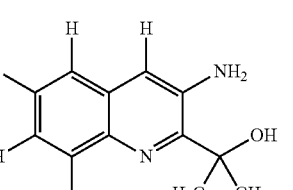 X-5
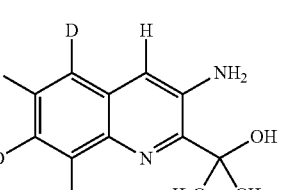 X-6

TABLE 1-continued

Representative Compounds

X-7 through X-20: structural diagrams of deuterated 6-chloro-3-amino-2-(2-hydroxypropan-2-yl)quinoline analogs with varying deuterium substitution patterns.

TABLE 1-continued

Representative Compounds

X-21

X-22

X-23

X-24

X-25

X-26

X-27

X-28

X-29

X-30

In some embodiments, the present disclosure provides a pharmaceutical composition comprising a compound depicted in Table 1, above, or a pharmaceutically acceptable salt thereof, and one or more pharmaceutically acceptable excipients or carriers.

In some embodiments, the present invention provides a unit dosage form comprising a disclosed pharmaceutical composition.

In some embodiments, the unit dosage form comprises a spray-dried pharmaceutical composition comprising compound I-1, or a pharmaceutically acceptable salt thereof. In some embodiments, the unit dosage form is in the form of an oral-powder-for-constitution (OPC) formulation.

In some embodiments, the unit dosage form comprises about 1 mg to about 2000 mg of a disclosed quinoline compound, or a pharmaceutically acceptable salt thereof.

In some embodiments, the unit dosage form comprises about 1 mg to about 2000 mg I-1, or a pharmaceutically acceptable salt thereof.

In some embodiments, the unit dosage form comprises about 1 mg to about 1000 mg I-1, or a pharmaceutically acceptable salt thereof.

In some embodiments, the unit dosage form comprises about 1 mg to about 800 mg, 5 mg to about 500 mg, 10 mg to about 600 mg, or about 10 mg to about 350 mg I-1, or a pharmaceutically acceptable salt thereof.

In some embodiments, the unit dosage form comprises about 1 mg, about 5 mg, about 10 mg, about 30 mg, about 40 mg, about 350 mg, or about 450 mg of compound I-1, or a pharmaceutically acceptable salt thereof.

In some embodiments, the unit dosage form comprises about 10 mg, about 25 mg, about 50 mg, about 75 mg, about 100 mg, about 150 mg, about 200 mg, about 250 mg, about 300 mg, about 400 mg, about 500 mg, about 750 mg, or about 1000 mg of compound I-1, or a pharmaceutically acceptable salt thereof.

In some embodiments, the unit dosage form is suitable for systemic administration.

In some embodiments, the unit dosage form is suitable for parenteral or oral administration.

In some embodiments, the unit dosage form is suitable for oral administration.

In some embodiments, the present invention provides a unit dosage form comprising a pharmaceutical composition, in liquid form, comprising about 1 mg to about 2000 mg I-1, or a pharmaceutically acceptable salt thereof, and water.

In some embodiments, the unit dosage form is a capsule or tablet.

In some embodiments, the one or more pharmaceutically acceptable excipients or carriers are selected from one or more of Eudragit L100, microcrystalline cellulose, lactose monohydrate, croscarmellose sodium, crospovidone (Kollidon CL), a vinylpyrrolidone-vinyl acetate copolymer such as Kollidon VA64, sodium lauryl sulfate, and magnesium stearate.

In one aspect, the present disclosure provides a pharmaceutical composition comprising:
a) compound I-1:

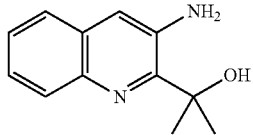

or a pharmaceutically acceptable salt thereof,
b) one or more fillers;
c) one or more binders;
d) one or more disintegrants;
e) one or more glidants;
f) one or more lubricants;
g) optionally, one or more surfactants; and
h) optionally, one or more effervescent components.

In some embodiments, compound I-1 or a pharmaceutically acceptable salt thereof is present in the pharmaceutical composition as a spray-dried solid (e.g., obtained from a spray drying dispersion (SDD)).

In some embodiments, the pharmaceutical composition exhibits pharmacokinetics results as described herein.

In some embodiments, the spray-dried solid comprises a concentration-enhancing polymer.

Exemplary concentration-enhancing polymers include those described in U.S. Pat. Nos. 7,780,988 and 10,004,719, each of which is hereby incorporated by reference. In some embodiments, the spray-dried solid is prepared substantially as described in U.S. Pat. No. 7,780,988 or 10,004,719, each of which is hereby incorporated by reference.

In some embodiments, the concentration-enhancing polymer is selected from selected from the group consisting of ionizable cellulosic polymers, non-ionizable cellulosic polymers, and ionizable non-cellulosic polymers, and blends thereof.

In some embodiments, the concentration-enhancing polymer is selected from the group consisting of hydroxypropyl methyl cellulose, hydroxypropyl cellulose, carboxymethyl ethyl cellulose, hydroxypropyl methyl cellulose acetate succinate, hydroxypropyl methyl cellulose phthalate, cellulose acetate phthalate, and cellulose acetate trimellitate, and blends thereof.

In some embodiments, the spray-dried solid comprises an anionic copolymer such as one based on methacrylic acid and methyl methacrylate. In some embodiments, the anionic copolymer is a Eudragit polymer. In some embodiments, the anionic copolymer is Eudragit L100.

In some embodiments, the pharmaceutical composition exhibits a PK result, after oral administration to a human subject, as described herein.

In some embodiments, the one or more fillers are selected from ammonium aliginate, calcium carbonate, calcium lactate, calcium phosphate, calcium silicate, calcium sulfate, cellulose acetate, compressible sugar (e.g., lactose, glucose, and sucrose), corn starch, dextrates, erythritol, ethyl cellulose, glyceryl palmitostearate, isomalt, kaolin, magnesium carbonate, magnesium oxide, maltodextrin, medium-chain triglycerides, microcrystalline cellulose, pre-gelatinized starch, polydextrose, polymethacrylates, silicic acid, simethicone, sodium alginate, sodium chloride, mannitol, sorbitol, starch, sugar spheres, sulfobutylether β-cyclodextrin, talc, tragacanth, trehalose, and xylitol, or a combination thereof.

In some embodiments, the filler is microcrystalline cellulose. In some embodiments, the filler is lactose. In some embodiments, the filler is starch. In some embodiments, the filler is a combination of starch and lactose.

In some embodiments, the filler is a combination of lactose, microcrystalline cellulose, and mannitol.

In some embodiments, the one or more binders are selected from acacia gum, agar, alginic acid, calcium carbonate, calcium lactate, carbomers (e.g., acrylic acid polymer, carboxy polymethylene, polyacrylic acid, carboxyvinyl polymer), carboxymethylcellulose sodium, carboxycellulose, carrageenan, cellulose acetate phthalate, *ceratonia*, chitosan, copovidone, corn starch, cottonseed oil, dextrates, dextrin, dextrose, ethylcellulose, gelatin, glyceryl behenate, guar gum, hydrogenated vegetable oil type I, hydroxyethylcellulose, hydroxyethylmethyl cellulose, hydroxypropyl cellulose, hydroxypropyl methylcellulose, hypromellose, inulin, lactose, magnesium aluminum silicate, maltodextrin, maltose, methylcellulose, microcrystalline cellulose, pectin, poloxamer, polycarbohil, polydextrose, polyethylene oxide, polymetharylates, polyvinylpyrrolidone, pre-gelatinized starch, povidone, sodium alginate, starch, stearic acid, sucrose, tricaprylin, vitamin E polyethylene glycol succinate, and zein.

In some embodiments, the binder is a vinylpyrrolidone-vinyl acetate copolymer. In some embodiments, the binder is Kollidon VA64.

In some embodiments, the one or more disintegrants are selected from agar, bentonite, celluloses (e.g., methylcellulose and carboxymethylcellulose), wood products, natural sponge, cation-exchange resins, alginic acid, gums (e.g., guar gum and Veegum HV), citrus pulp, cross-linked celluloses (e.g., croscarmellose), cross-linked polymers (e.g., crospovidone), cross-linked starches, calcium carbonate, microcrystalline cellulose (e.g., sodium starch glycolate), polacrilin potassium, starches (e.g., corn starch, potato starch, tapioca starch, and pre-gelatinized starch), clays, and aligns; and mixtures thereof.

In some embodiments, the one or more glidants are selected from colloidal silicon dioxide, CAB-O-SIL™ (Cabot Co. of Boston, MA), fumed silica (Aerosil), and asbestos-free talc.

In some embodiments, the one or more glidants are selected from colloidal silicon dioxide and fumed silica.

In some embodiments, the one or more lubricants are selected from calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. In some embodiments, the one or more lubricants are selected from a syloid silica gel (AEROSIL200), a coagulated aerosol of synthetic silica (marketed by Degussa Co. of Plano, Tex.), CAB-O-SIL™, and mixtures thereof.

In some embodiments, the one or more surfactants are selected from polyoxyethylene (20) sorbitan monolaurate (e.g., Tween-20), polyoxyethylene (20) sorbitan monooleate (e.g., Tween-80), sodium laurel sulfate, and sodium dodecyl sulfate.

In some embodiments, the surfactant comprises sodium lauryl sulfate.

In some embodiments, the one or more effervescent components are selected from a carbon dioxide-releasing component, such as a bicarbonate-containing component. In some embodiments, the effervescent component comprises sodium bicarbonate, such as a compressed mixture of sodium bicarbonate and an organic acid. In some embodiments, the organic acid is citric acid or tartaric acid.

In some embodiments, the pharmaceutical composition optionally comprises an antioxidant or chelating agent. In some embodiments, the antioxidant is ascorbyl palmitate, butylated hydroxyanisole, butylated hydroxytoluene (BHT), calcium stearate, citric acid, sodium thiosulfate, sodium metabisulfite, vitamin E, or 3,4-dihydroxybenzoic acid. In some embodiments, the chelating agent is EDTA (ethylenediamine tetraacetic acid) or disodium EDTA.

In some embodiments, the pharmaceutical composition optionally comprises one or more diluents. In some embodiments, the pharmaceutical composition comprises one or more diluents selected from dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol, and talc; or ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethylacrylates, simethicone, sodium alginate, sodium chloride, sorbitol, starch, pregelatinized starch, sucrose, sulfobutylether-β-cyclodextrin, talc, tragacanth, trehalose, and xylitol.

In some embodiments, the pharmaceutical composition optionally further comprises one or more additional binders, fillers, diluents, disintegrants, wetting agents, lubricants, glidants, coloring agents, dye-migration inhibitors, sweetening agents, flavoring agents, emulsifying agents, suspending and dispersing agents, preservatives, antioxidants, chelating agents, solvents, non-aqueous liquids, organic acids, and sources of carbon dioxide.

In one aspect, the present disclosure provides a pharmaceutical composition comprising:
a) compound I-1:

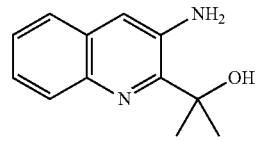

or a pharmaceutically acceptable salt thereof,
b) one or more fillers comprising at least one of microcrystalline cellulose, mannitol, and lactose monohydrate;
c) one or more binders comprising at least Kollidon VA64;
d) one or more disintegrants comprising at least one of croscarmellose sodium and crospovidone;
e) one or more glidants comprising fumed silica;
f) one or more lubricants comprising magnesium stearate;
g) optionally, one or more surfactants comprising lauryl sulfate; and
h) optionally, one or more effervescent components.

In some embodiments, compound I-1 or a pharmaceutically acceptable salt thereof is present in the pharmaceutical composition as a spray-dried solid (e.g., obtained from a spray drying dispersion (SDD)). In some embodiments, the spray-dried solid comprises an anionic copolymer such as one based on methacrylic acid and methyl methacrylate. In some embodiments, the anionic copolymer is a Eudragit polymer. In some embodiments, the anionic copolymer is Eudragit L100.

In some embodiments, the unit dosage form exhibits pharmacokinetics results as described herein.

In one aspect, the present disclosure provides a pharmaceutical composition comprising:
a) compound I-1:

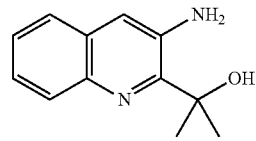

or a pharmaceutically acceptable salt thereof,
b) microcrystalline cellulose, mannitol, and lactose monohydrate;
c) Kollidon VA64;
d) croscarmellose sodium and crospovidone;
e) fumed silica;
f) magnesium stearate;
g) optionally, lauryl sulfate; and
h) optionally, one or more effervescent components.

In some embodiments, the lauryl sulfate is present. In some embodiments, the effervescent component is present and is a mixture of sodium bicarbonate and citric acid. In some embodiments, the effervescent component is Effersoda and citric acid.

In some embodiments, compound I-1 or a pharmaceutically acceptable salt thereof is present in the pharmaceutical composition as a spray-dried solid (e.g., obtained from a spray drying dispersion (SDD)). In some embodiments, the spray-dried solid comprises an anionic copolymer such as one based on methacrylic acid and methyl methacrylate. In some embodiments, the anionic copolymer is a Eudragit polymer. In some embodiments, the anionic copolymer is Eudragit L100.

In some embodiments, the unit dosage form exhibits pharmacokinetics results as described herein.

In one aspect, the present disclosure provides a pharmaceutical composition comprising:
a) a spray-dried solid comprising a mixture of Eudragit L100 and compound I-1:

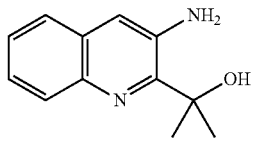

or a pharmaceutically acceptable salt thereof,
b) microcrystalline cellulose, mannitol, and lactose monohydrate;
c) Kollidon VA64;
d) croscarmellose sodium and crospovidone;
e) fumed silica;
f) magnesium stearate;
g) lauryl sulfate; and
h) optionally, one or more effervescent components.

In some embodiments, the effervescent component is not present. In some embodiments, the effervescent component is present and is a mixture of sodium bicarbonate, sodium carbonate, and citric acid.

In some embodiments, the pharmaceutical composition comprises about 5% to about 75% w/w of active ingredient. In some embodiments, the pharmaceutical composition comprises about 15% to about 60% w/w of active ingredient. In some embodiments, the pharmaceutical composition comprises about 20% to about 40% w/w of active ingredient. In some embodiments, the pharmaceutical composition comprises about 25% to about 37% w/w of active ingredient.

In some embodiments, the pharmaceutical composition comprises about 5%, 10%, 15%, 20%, 25%, 30%, 35%, 40%, 45%, 50%, 55%, 60%, 65%, 70%, 75%, 80%, 85%, 90%, or 95% w/w of active ingredient.

In some embodiments, the pharmaceutical composition comprises about 31% w/w of active ingredient.

In some embodiments, the active ingredient is compound I-1 or a pharmaceutically acceptable salt thereof.

In some embodiments, I-1 or a pharmaceutically acceptable salt thereof is provided as a spray-dried solid mixed with Eudragit L100. In some embodiments, about 0.9 mg to about 3.6 mg of Eudragit L100 is mixed with each 1 mg of I-1 or pharmaceutically acceptable salt thereof. In some embodiments, about 1.0 mg to about 3.0 mg of Eudragit L100 is mixed with each 1 mg of I-1 or pharmaceutically acceptable salt thereof. In some embodiments, about 1.5 mg to about 2.2 mg of Eudragit L100 is mixed with each 1 mg of I-1 or pharmaceutically acceptable salt thereof. In some embodiments, about 1.8 mg of Eudragit L100 is mixed with each 1 mg of I-1 or pharmaceutically acceptable salt thereof.

In some embodiments, the pharmaceutical composition comprises about 16% to 40% w/w I-1 or pharmaceutically acceptable salt thereof and about 29.3% to about 80% w/w Eudragit L100.

In some embodiments, the unit dosage form exhibits pharmacokinetics results as described herein.

In some embodiments, the pharmaceutical composition comprises about 1% to about 20% w/w of a filler described herein.

In some embodiments, the pharmaceutical composition comprises about 1% to about 20% w/w of a disintegrant described herein.

In some embodiments, the pharmaceutical composition comprises about 2% to about 18% w/w of a binder described herein. In some embodiments, the pharmaceutical composition comprises about 4% to about 16% w/w of a binder described herein. In some embodiments, the pharmaceutical composition comprises about 5% to about 10% w/w of a binder described herein. In some embodiments, the pharmaceutical composition comprises about 7% w/w of a binder described herein.

In some embodiments, the pharmaceutical composition comprises about 0.05% to about 2.0% w/w of a lubricant described herein. In some embodiments, the pharmaceutical composition comprises about 0.1% to about 1.0% w/w of a lubricant described herein. In some embodiments, the pharmaceutical composition comprises about 0.25% to about 0.75% w/w of a lubricant described herein. In some embodiments, the pharmaceutical composition comprises about 0.5% w/w of a lubricant described herein.

In some embodiments, the pharmaceutical composition comprises about 0.05% to about 2.0% w/w of a glidant described herein. In some embodiments, the pharmaceutical composition comprises about 0.1% to about 1.0% w/w of a glidant described herein. In some embodiments, the pharmaceutical composition comprises about 0.25% to about 0.75% w/w of a glidant described herein. In some embodiments, the pharmaceutical composition comprises about 0.5% w/w of a glidant described herein.

In some embodiments, the pharmaceutical composition comprises about 0.05% to about 2.0% w/w of a surfactant described herein. In some embodiments, the pharmaceutical composition comprises about 0.1% to about 1.0% w/w of a surfactant described herein. In some embodiments, the pharmaceutical composition comprises about 0.25% to about 0.75% w/w of a surfactant described herein. In some embodiments, the pharmaceutical composition comprises about 0.5% w/w of a surfactant described herein.

In some embodiments, the pharmaceutical composition comprises about 0.05% to about 2.0% w/w of an effervescent component described herein. In some embodiments, the pharmaceutical composition comprises about 0.1% to about 1.0% w/w of an effervescent component described herein. In some embodiments, the pharmaceutical composition comprises about 0.25% to about 0.75% w/w of an effervescent component described herein. In some embodiments, the pharmaceutical composition comprises about 0.5% w/w of an effervescent component described herein.

In one aspect, the present disclosure provides a pharmaceutical composition comprising:

| Component | Quantity (mg/unit) | % (w/w) of Total |
|---|---|---|
| Compound I-1 | 100 | 31.5% |
| Eudragit L100 | 185.7 | 58.5% |
| Pearlitol 200 SD (Mannitol) | 6.4 | 2.0% |
| Kollidon ® VA 64 Fine | 22.2 | 7.0% |
| Aerosil 200 Pharma (Fumed Silica) | 1.6 | 0.50% |
| Magnesium Stearate | 1.6 | 0.50% |
| Total | 317.5 | — |

In one aspect, the present disclosure provides a pharmaceutical composition comprising:

| No. | Component | Function |
|---|---|---|
| 1 | I-1 Crystalline: Eudragit L100 | active ingredient and anionic copolymer excipient |
| 2 | Microcrystalline cellulose (Avicel PH102) | Filler |
| 3 | Mannitol (Pearlitol 200 SD) | Filler |
| 4 | Lactose Monohydrate | Filler |
| 5 | Croscarmellose sodium (Ac-Di-Sol) | Disintegrant |
| 6 | Crospovidone (Kollidon CL) | Disintegrant |
| 7 | Kollidon VA64 | Binder |
| 8 | Magnesium Stearate | Lubricant |
| 9 | Fumed Silica (Aerosil) | Glidant |
| 10 | Sodium Lauryl Sulphate | Surfactant |
| 11 | Citric Acid | Acidity regulator for effervescent component |
| 12 | Effer-soda (surface modified sodium bicarbonate/carbonate) | Effervescent component |
| 13 | Gelatin capsule | Encapsulation |
| 14 | Hydroxypropyl methylcellulose (HPMC) capsule | Encapsulation |

In some embodiments, the present disclosure provides a unit dosage form comprising a pharmaceutical composition described herein.

In some embodiments, the unit dosage form is in the form of a capsule or tablet. In some embodiments, the capsule is a gelatin capsule. In some embodiments, the capsule is a hydroxypropyl methylcellulose (HPMC) capsule.

In some embodiments, the unit dosage form comprises about 1 mg to about 800 mg, 5 mg to about 500 mg, 10 mg to about 600 mg, or about 10 mg to about 350 mg I-1, or a pharmaceutically acceptable salt thereof.

In some embodiments, the unit dosage form comprises about 10 mg of compound I-1 or a pharmaceutically acceptable salt thereof. In some embodiments, the unit dosage form comprises about 100 mg of compound I-1 or a pharmaceutically acceptable salt thereof. In some embodiments, the unit dosage form comprises about 300 mg of compound I-1 or a pharmaceutically acceptable salt thereof.

In some embodiments, the present invention provides a pharmaceutical composition comprising:
(a) Compound I-1:

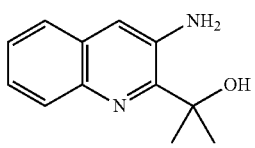

I-1 or a pharmaceutically acceptable salt thereof, as about 15% to about 60% by weight of the composition;
(b) a Eudragit polymer as about 27.5% to about 80% by weight of the composition;
(c) a filler comprising one or more of mannitol, lactose, and microcrystalline cellulose as about 1.0% to about 6.0% by weight of the composition;
(d) a binder comprising a Kollidon® binder as about 3.5% to about 14% by weight of the composition;
(e) a glidant comprising a silica glidant as about 0.25% to about 2% by weight of the composition;
(f) a lubricant comprising magnesium stearate as about 0.25% to about 2.0% by weight of the composition; and (g) optionally, croscarmellose sodium as 0% to about 8.0% by weight of the composition.

In some embodiments, the present invention provides a pharmaceutical composition comprising:
(a) Compound I-1:

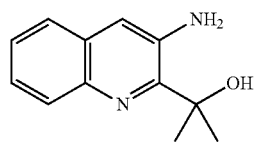

I-1 or a pharmaceutically acceptable salt thereof, as about 25% to about 40% by weight of the composition;
(b) a Eudragit polymer as about 40% to about 68% by weight of the composition;
(c) a filler comprising one or more of mannitol, lactose, and microcrystalline cellulose as about 1.0% to about 4.0% by weight of the composition;
(d) a binder comprising a Kollidon® binder as about 4.0% to about 10% by weight of the composition;
(e) a glidant comprising a silica glidant as about 0.25% to about 2.0% by weight of the composition;
(f) a lubricant comprising magnesium stearate as about 0.25% to about 2% by weight of the composition; and
(g) optionally, croscarmellose sodium as 0% to about 8.0% by weight of the composition.

In some embodiments, the present invention provides a unit dosage form comprising a pharmaceutical composition comprising all or substantially all components as described in any one of Tables F, G, H, I, and J.

In some embodiments, a unit dosage form is a capsule, tablet, or powder-in-bottle form.

In some embodiments, a unit dosage form of the present disclosure exhibits pharmacokinetics results as described herein.

In some embodiments, a unit dosage form described herein that comprises compound I-1, or a pharmaceutically acceptable salt thereof, upon oral administration to a human subject in a daily dose of 20 mg, 50 mg, 100 mg, 200 mg, 400 mg, 700 mg, or 1200 mg (or about such doses, as the case may be), provides a pharmacokinetic result shown in the table below:

TABLE 2

| | Exemplary PK Results | | | | | | |
|---|---|---|---|---|---|---|---|
| | 20 mg | 50 mg | 100 mg | 200 mg | 400 mg | 700 mg | 1200 mg |
| $C_{max}$ (ng/mL) | 26.4 | 56.7 | 140 | 459 | 869 | 2020 | 4220 |
| $AUC_{inf}$ (ng * h/mL) | 50.0 | 156 | 433 | 1140 | 2730 | 6710 | 14500 |
| $t_{1/2}$ (h) | NC | NC | 3.52 | 6.04 | 6.15 | 7.33 | 7.69 |
| $C_{max}$ (ng/mL) | about 26.4 | about 56.7 | about 140 | about 459 | about 869 | about 2020 | about 4220 |
| $AUC_{inf}$ (ng * h/mL) | about 50.0 | about 156 | about 433 | about 1140 | about 2730 | about 6710 | about 14500 |
| $t_{1/2}$ (h) | | | about 3.52 | about 6.04 | about 6.15 | about 7.33 | about 7.69 |

In some embodiments, a unit dosage form described herein that comprises as an active ingredient compound I-1, or a pharmaceutically acceptable salt thereof, upon oral administration to a human subject in a dose of 50 mg BID, 150 mg BID, 350 mg BID, or 600 mg BID (or about such doses, as the case may be), provides a pharmacokinetic result shown in the table below:

TABLE 3

Exemplary PK Results

| Day | Dose | Mean $C_{max}$ (ng/mL) | Mean $AUC_{0-12}$ (h * ng/mL) | Mean $t_{1/2}$ (h) |
|---|---|---|---|---|
| 1 | 50 mg BID | 70.2 | 148 | 3.49 |
|   | 150 mg BID | 343 | 809 | 4.86 |
|   | 350 mg BID | 1190 | 2950 | 5.67 |
|   | 600 mg BID | 2230 | 6450 | 4.15 |
| 10 | 50 mg BID | 85.9 | 252 | 5.25 |
|   | 150 mg BID | 320 | 1170 | 6.34 |
|   | 350 mg BID | 1230 | 4340 | 6.83 |
|   | 600 mg BID | 1700 | 7220 | 4.66 |
| 1 | about 50 mg BID | about 70.2 | about 148 | about 3.49 |
|   | about 150 mg BID | about 343 | about 809 | about 4.86 |
|   | about 350 mg BID | about 1190 | about 2950 | about 5.67 |
|   | about 600 mg BID | about 2230 | about 6450 | about 4.15 |
| 10 | about 50 mg BID | about 85.9 | about 252 | about 5.25 |
|   | about 150 mg BID | about 320 | about 1170 | about 6.34 |
|   | about 350 mg BID | about 1230 | about 4340 | about 6.83 |
|   | about 600 mg BID | about 1700 | about 7220 | about 4.66 |

In some embodiments, the human subject is a healthy human subject.

In some embodiments, the pharmacokinetic result described herein is obtained in a healthy human subject.

In some embodiments, a disclosed unit dosage form that comprises as an active ingredient compound I-1, or a pharmaceutically acceptable salt thereof, upon oral administration to a human subject in a dose of about 50 mg BID, 150 mg BID, 350 mg BID, or 600 mg BID, provides a pharmacokinetic result shown in the table above on day 1 of administration.

In some embodiments, a disclosed unit dosage form that comprises as an active ingredient compound I-1, or a pharmaceutically acceptable salt thereof, upon oral administration to a human subject in a dose of about 50 mg BID, 150 mg BID, 350 mg BID, or 600 mg BID, provides a pharmacokinetic result shown in the table above after day 1 but before day 10 of administration.

In some embodiments, a disclosed unit dosage form that comprises as an active ingredient compound I-1, or a pharmaceutically acceptable salt thereof, upon oral administration to a human subject in a dose of about 50 mg BID, 150 mg BID, 350 mg BID, or 600 mg BID, provides a pharmacokinetic result shown in the table above on day 10 of administration.

In some embodiments, a disclosed unit dosage form that comprises as an active ingredient compound I-1, or a pharmaceutically acceptable salt thereof, upon oral administration to a human subject in a dose of about 50 mg BID, 150 mg BID, 350 mg BID, or 600 mg BID, provides a pharmacokinetic result shown in the table above after day 10 of administration.

In some embodiments, the $t_{1/2}$ in a human subject after administration of a disclosed unit dosage form is from about 3 to about 8 hours.

In some embodiments, the $t_{1/2}$ in a human subject after administration of a disclosed unit dosage form is from about 3.5 to about 7.5 hours.

In some embodiments, the $t_{1/2}$ in a human subject after administration of a disclosed unit dosage form is about 3.5, about 4.8, about 6.0, about 6.4, about 6.15, about 6.8, about 7.3, or about 7.7 hours.

In some embodiments, a disclosed unit dosage form comprising compound I-1, or a pharmaceutically acceptable salt thereof, provides an oral bioavailability of at least 70%.

In some embodiments, a disclosed unit dosage form comprising compound I-1, or a pharmaceutically acceptable salt thereof, provides an oral bioavailability of at least 75%.

In some embodiments, a disclosed unit dosage form comprising compound I-1, or a pharmaceutically acceptable salt thereof, provides an oral bioavailability of at least 80%.

In some embodiments, a disclosed unit dosage form comprising compound I-1, or a pharmaceutically acceptable salt thereof, provides an oral bioavailability of at least 80%, 85%, 90%, or 95%.

In some embodiments, the present disclosure provides a pharmaceutical formulation comprising a compound described herein, or a pharmaceutically acceptable salt thereof, for use in a disclosed method of treatment of a disease, disorder, or condition. As used herein, the terms "treatment," "treat," and "treating" refer to reversing, alleviating, delaying the onset of, or inhibiting the progress of a disease, disorder, or condition; or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). In some cases, treatment is continued after symptoms have resolved, for example to prevent, delay or lessen the severity of their recurrence.

In another aspect, the present invention provides a method for reducing levels of one or more toxic aldehydes in a subject, comprising administering to a subject in need thereof a pharmaceutical composition, as described herein.

In another aspect, the present invention provides a method for reducing levels of one or more toxic aldehydes in a biological sample, comprising contacting the biological sample with a pharmaceutical composition, as described herein. In some embodiments, the method is carried out in vitro.

In another aspect, the present invention provides a method for treating a disease, disorder, or condition, comprising administering to a subject in need thereof a pharmaceutical composition, as described herein.

In some embodiments, the disease, disorder, or condition is a viral infection.

In some embodiments, the viral infection is caused by a coronavirus, hepatitis A virus, hepatitis B virus, dengue virus, yellow fever virus, Zika virus, influenza virus, respiratory syncytial virus (RSV), norovirus, herpesvirus, human immunodeficiency virus (HIV), Ebola virus, human T-lymphotropic virus (HTLV)-1 and -2, Epstein-Barr virus, Lassa virus, or Crimean-Congo hemorrhagic fever virus.

In some embodiments, the viral infection is caused by a coronavirus. In some embodiments, the coronavirus is an alpha, beta, gamma, or delta coronavirus. In some embodiments, the coronavirus is one associated with severe respiratory symptoms such as SARS.

In some embodiments, the viral infection is caused by a coronavirus, wherein the coronavirus is 229E (alpha coronavirus), NL63 (alpha coronavirus), OC43 (beta coronavirus), HKU1 (beta coronavirus), MERS-CoV (the beta coronavirus that causes Middle East Respiratory Syndrome, or MERS), SARS-CoV (the beta coronavirus that causes severe acute respiratory syndrome, or SARS), or SARS-CoV-2 (coronavirus disease 2019, or COVID-19).

In some embodiments, the viral infection is caused by SARS-CoV-2.

In some embodiments, the viral infection is caused by an influenza virus.

In some embodiments, the viral infection is caused by an influenza virus, wherein the viral infection is selected from influenza type A and influenza type B. In some embodiments, the influenza virus is B/Yamagata or B/Victoria.

In some embodiments, the viral infection is caused by an influenza virus selected from H5N1, H1N1 and H3N2.

In some embodiments, the viral infection is caused by a Zika virus.

In some embodiments, a second therapeutic agent is administered to the patient, wherein the second therapeutic agent is selected from an antiviral agent, an antibiotic, and an NSAID.

In some embodiments, the second therapeutic agent is an antiviral agent, wherein the antiviral agent is appropriate for treating the viral infection.

In some embodiments, the second therapeutic agent is selected from chloroquine, remdesivir, hydroxychloroquine, interferon, ribavirin, umifenovir, teicoplanin, lopinavir, ritonavir, nitazoxanide, camostat, favipiravir, tocilizumab, and a passive antibody therapy.

In some embodiments, the present invention provides a method of treating, preventing, and/or reducing risk of a skin disease, disorder, or condition selected from atopic dermatitis, atopic eczema, and psoriasis, or an ocular disease, disorder, or condition selected from diabetic macular edema and Stargardt's disease, comprising administering to a patient in need thereof a disclosed pharmaceutical composition comprising a disclosed quinoline compound.

In some embodiments, the present disclosure provides use of the pharmaceutical composition described herein in the manufacture of a medicament for the treatment, prevention, and/or reduction of a risk of a skin disease, disorder or condition selected from atopic dermatitis, atopic eczema, and psoriasis, or an ocular disease, disorder or condition selected from diabetic macular edema and Stargardt's disease.

In some embodiments, a method of the disclosure is directed to treatment of atopic dermatitis. In some embodiments, a method of treating or reducing the risk of atopic dermatitis comprises administering to a patient in need thereof an effective amount of a compound disclosed herein. Generally, atopic dermatitis is characterized as an inflammatory condition of the skin presenting erythema, pruritus, scaling, lichenification, and papulovesicles. The pathogenesis of atopic dermatitis is multifactorial and involves a complex immunologic cascade, including disruption of the epidermal barrier, IgE dysregulation, defects in the cutaneous cell-mediated immune response, and genetic factors.

In some embodiments, the patient treated has a history of atopy (atopic disease). Generally, atopy refers to personal or family history of atopic eczema, asthma, and allergies.

In some embodiments, the atopic dermatitis treated is relapsing atopic dermatitis. Relapsing atopic dermatitis is a flare, exacerbation, or recurrence of atopic dermatitis following a remission of the disease, disorder or condition.

In some embodiments, the patient treated is identified as having a loss of function of profilaggrin (FLG) mutation. The inactive precursor profilaggrin protein is a large, complex, highly phosphorylated polypeptide that is the main constituent of the keratohyalin F granules that are visible in the granular cell layer of the epidermis. Various mutations in the FLG gene have been identified in individuals of atopic dermatitis and is a risk factor for atopic dermatitis (see, e.g., O'Regan et al., J Allergy Clinical Immunol., 2009; 124(3) Supplement 2:R2-R6).

In some embodiments, the patient has a loss of function of profilaggrin (FLG) mutation resulting in reduction of FLG protein expression.

In some embodiments, the atopic dermatitis treated is mild to moderate atopic dermatitis.

In some embodiments, the atopic dermatitis treated is moderate to severe atopic dermatitis.

In some embodiments, the atopic dermatitis treated is in the acute phase. In some embodiments, acute atopic dermatitis presents with a vesicular, weeping, crusting eruption.

In some embodiments, the atopic dermatitis treated is in the subacute phase. In some embodiments, subacute atopic dermatitis presents with dry, scaly, erythematous papules and plaques.

In some embodiments, the atopic dermatitis treated is in the chronic phase. In some embodiments, chronic atopic dermatitis demonstrates lichenification from repeated scratching.

In some embodiments, a method of the disclosure is directed to treatment of psoriasis. In some embodiments, a method of treating or reducing the risk of psoriasis comprises administering to a patient in need thereof an effective amount of a compound disclosed herein. Generally, psoriasis is a chronic, immune mediated disease characterized by raised, red, scaly patches on the skin. These conditions arise in part from acceleration of the growth cycle of skin cells.

In some embodiments, the psoriasis treated is plaque psoriasis. Plaque psoriasis usually presents as raised, inflamed, red lesions, covered by silvery, white scales, most often on the elbows, knees, scalp, and lower back.

In some embodiments, the psoriasis treated is guttate psoriasis. Guttate psoriasis often starts in childhood or young adulthood. It presents as small, red, individual spots on the skin, where the spots are not usually as thick or as crusty as the lesions in plaque psoriasis.

In some embodiments, the psoriasis treated is inverse psoriasis. Inverse psoriasis presents as red lesions, usually without the scales that occur in plaque psoriasis. The lesions can be smooth and shiny, and can occur in the armpits, groin, breast, and in skin folds.

In some embodiments, the psoriasis treated is pustular psoriasis. Pustular psoriasis presents as white pustules, or blisters of noninfectious pus, with red skin surrounds. It can affect certain areas of the body, such as the hands and feet, or most of the body.

In some embodiments, the psoriasis treated is erythrodermic psoriasis. Erythrodermic psoriasis is inflammatory and presents as exfoliation, or peeling of the skin with severe itching and pain. Edema may also be present.

In some embodiments, the psoriasis treated is mild psoriasis. Mild forms affect about 10% or less of total skin surface.

In some embodiments, the psoriasis treated is moderate to severe psoriasis. Moderate to severe forms affect >10% or more of total skin surface, and may require oral or systemic administration of therapeutic agents.

In some embodiments, the psoriasis treated is early onset psoriasis (type I psoriasis).

In some embodiments, the psoriasis treated is late onset psoriasis (type II psoriasis).

In some embodiments, a method of the disclosure is directed to treatment of diabetic macular edema (DME). In some embodiments, a method of treating or reducing the risk of diabetic macular edema (DME) comprises administering to a patient in need thereof an effective amount of a compound disclosed herein. Generally, DME is complication of diabetes and sometimes referred to a diabetic retinopathy. Damage to the small blood vessels of the retina arising from diabetes can result in leakage of fluid into the retina, which can lead to swelling of the surrounding tissue, including the macula, thereby leading to loss of vision.

In some embodiments, the patient treated is diagnosed with type 1 diabetes.

In some embodiments, the patient treated is diagnosed with type 2 diabetes.

In some embodiments, the DME treated is clinically significant macular edema (CSME). Clinically, CSME is defined as DME meeting at least one of the criteria presented as follows: (a) thickening of the retina at or within 500 μm of the center of the macula; (b) hard exudates at or within 500 μm of the center of the macula, if associated with thickening of adjacent retina (not counting residual hard exudates remaining after disappearance of retinal thickening); and (c) any zone(s) of retinal thickening 1 disc area or larger, any part of which is within 1 disc diameter of the center of the macula.

In some embodiments, the DME treated is center-involved DME. In center-involved DME, the central macula is generally the thickest portion of the retina and is an inversion of the normal morphology.

In some embodiments, the DME treated is non-center-involved DME. Non-central DME lack involvement of the center of the macula.

In some embodiments, the DME treated is focal DME. Focal edema often occurs associated with a cluster of microaneurysms, sometimes surrounded by an incomplete ring of hard exudates. It may be associated with less macular thickening, better visual acuity, and less severe retinopathy severity.

In some embodiments, the DME treated is diffuse type DME. Diffuse macular edema occurs from dilated retinal capillaries in the retina and involve a larger area of retinal thickening.

In some embodiments, the DME treated is accompanied by retinal detachment or severe non-clearing vitreous hemorrhage.

In some embodiments, the patient treated has undergone focal laser photocoagulation therapy.

In some embodiments, the patient treated has undergone grid laser photocoagulation therapy.

In some embodiments, a method of the disclosure is directed to treatment of Stargardt's disease. In some embodiments, a method of treating or reducing the risk of Stargardt's disease comprises administering to a patient in need thereof an effective amount of a compound disclosed herein. Generally, Stargardt's disease is inherited form of macular dystrophy characterized by bilateral vision loss, including dyschromatopsia and central scotomata, with characteristic macular atrophy and yellow-white flecks at the level of the retinal pigment epithelium (RPE) at the posterior pole. Stargardt's disease may also be referred to as Stargardt macular dystrophy, juvenile macular degeneration, or fundus flavimaculatus. Onset of Stargardt's disease occurs most commonly in childhood, with the next peak being early adulthood, and least frequently in later adulthood. Better prognosis is generally associated with a later onset.

In some embodiments, the Stargardt's disease treated is childhood-onset Stargardt's disease.

In some embodiments, the Stargardt's disease treated is adult-onset or late onset Stargardt's disease.

In some embodiments, the severity of Stargardt's disease can be classified based on electrophysiological assessment (see, e.g., Tanna et al., British Journal of Ophthalmology 2017; 101:25-30).

In some embodiments, the Stargardt's disease treated is classified in Group 1. Stargardt's disease in Group 1 display a severe pattern electroretinogram (ERG) abnormality (macular dysfunction) with normal full-field ERGs.

In some embodiments, the Stargardt's disease treated is classified in Group 2. Stargardt's disease in Group 2 display the characteristics of Group 1 and have in addition generalised loss of cone function. Patients in Group 2 have intermediate variable prognosis.

In some embodiments, the Stargardt's disease treated is classified in Group 3. Stargardt's disease in Group 3 display an additional generalised loss of both cone and rod function. Patients in Group 3 show the worst prognosis.

In some embodiments, the patient treated is identified as having a mutation in retina-specific ATP-binding cassette transporter (ABCA4) gene resulting in reduction or defect in ABCA4 function. Mutations in ABCA4 are the most common forms of inherited Stargardt's disease.

In some embodiments, the patient treated is identified as having mutation in ABCA4 gene that are associated with childhood-onset Stargardt's disease. Exemplary mutations associated with childhood-onset Stargardt's disease include, among others, 634C>T, 768G>T, 1317G>A, 1531C>T, 1557C>A, 5308T>G, 6088C>T, or 6449G>A.

In some embodiments, the patient treated is identified as having mutation in ABCA4 gene that are associated with adult-onset or late onset Stargardt's disease. Exemplary mutations associated with adult-onset or late onset Stargardt's disease include, among others, 769-784C>T, 2486C>T, 5603A>T, or 5882G>A.

As further discussed below, the compound or pharmaceutically acceptable salt thereof described herein can be administered systemically to treat the indications described herein. In some embodiments, the compound or pharmaceutically acceptable salt thereof is administered orally as part of a solid pharmaceutical composition. In some embodiments, the pharmaceutical composition is a liquid. In some embodiments, the pharmaceutical composition is administered as a liquid via nasogastric tube.

In some embodiments, for the ocular indications of diabetic macular edema or Stargardt's disease, the compound or pharmaceutically acceptable salt thereof is administered intravitreally.

In some embodiments, the compound is I-1 or a pharmaceutically acceptable salt thereof. In some embodiments, the compound is I-2 or a pharmaceutically acceptable salt thereof.

In some embodiments, the disease, disorder, or condition is acute respiratory distress syndrome (ARDS). In some embodiments, the ARDS is associated with a viral infection. In some embodiments, the viral infection is accompanied by viral sepsis.

In some embodiments, the viral infection is accompanied by viral pneumonia.

In some embodiments, a method of treating ARDS comprises administering to a patient with ARDS resulting from or associated with a viral infection an effective amount of the pharmaceutical composition disclosed herein.

In some embodiments, the viral infection is caused by a coronavirus, hepatitis A virus, hepatitis B virus, dengue virus, yellow fever virus, Zika virus, influenza virus, norovirus, herpesvirus, respiratory syncytial virus (RSV), human immunodeficiency virus (HIV), Ebola virus, human T-lymphotropic virus (HTLV)-1 and -2, Epstein-Barr virus, Lassa virus, or Crimean-Congo hemorrhagic fever virus.

In some embodiments, the viral infection is caused by a coronavirus. In some embodiments, the viral infection is caused by a coronavirus selected from 229E, NL63, OC43, HKUT, MERS-CoV, SARS-CoV, and SARS-CoV-2.

In some embodiments, the viral infection is caused by a coronavirus. In some embodiments, the coronavirus is an alpha, beta, gamma, or delta coronavirus. In some embodiments, the coronavirus is one associated with severe respiratory symptoms such as SARS.

In some embodiments, the viral infection is caused by a coronavirus, wherein the coronavirus is 229E (alpha coronavirus), NL63 (alpha coronavirus), OC43 (beta coronavirus), HKU1 (beta coronavirus), MERS-CoV (the beta coronavirus that causes Middle East Respiratory Syndrome, or MERS), SARS-CoV (the beta coronavirus that causes severe acute respiratory syndrome, or SARS), or SARS-CoV-2 (coronavirus disease 2019, or COVID-19).

In some embodiments, the viral infection is by a respiratory syncytial virus (RSV), influenza virus, coronavirus, or herpesvirus.

In some embodiments, the viral infection is by a coronavirus.

In some embodiments, the coronavirus is selected from 229E, NL63, OC43, HKU1, MERS-CoV, SARS-CoV, and SARS-CoV-2.

In some embodiments, the viral infection is by SARS-CoV-2.

In some embodiments, the viral infection is by an influenza virus.

In some embodiments, the influenza virus is influenza type A or influenza type B.

In some embodiments, the influenza virus is B/Yamagata or B/Victoria.

In some embodiments, the influenza virus is H5N1, H1N1 or H3N2.

In some embodiments, the ARDS is associated with a bacterial infection.

In some embodiments, the bacterial infection is accompanied by bacterial sepsis.

In some embodiments, the bacterial infection is accompanied by bacterial pneumonia.

In some embodiments, the bacterial infection is by *Streptococcus pneumoniae, Staphylococcus aureus, Legionella pneumophila, Pneumocystis jirovecii,* or *Haemophilus influenza.*

In some embodiments, the ARDS is associated with acute injury to the lungs caused by a chemical toxin or physical trauma.

In some embodiments, the acute injury to the lungs is by a chemical toxin.

In some embodiments, the chemical toxin that causes acute lung injury is a choking agent, vesicant, or nerve agent.

In some embodiments, the chemical toxin is a choking agent, wherein the choking agent is chlorine gas, phosgene, carbonyl chloride, hydrogen sulfide, or ammonia.

In some embodiments, the chemical toxin is a vesicant, wherein the vesicant is sulfur mustard or nitrogen mustard.

In some embodiments, the chemical toxin is a nerve agent, wherein the nerve agent is tabun, sarin, soman, or VX.

In some embodiments, the ARDS is associated with acute injury to the lungs caused by a biological toxin.

In some embodiments, the biological toxin is ricin, botulinum toxin, or staphylococcal enterotoxin B.

In some embodiments, the patient is being treated by mechanical ventilation.

In some embodiments, the disease, disorder, or condition is an inflammatory condition. In some embodiments, the inflammatory disorder is systemic. In some embodiments, the inflammatory disorder is localized to a particular tissue or organ. In some embodiments, the disease, disorder or condition for treatment with the compounds of the disclosure is non-alcoholic fatty liver disease (NAFLD), non-alcoholic steatohepatitis (NASH), inflammatory bowel disease, Crohn's disease, ulcerative colitis (UC), psoriasis, IBS (irritable bowel syndrome or spastic colon), including spastic colon, ankylosing spondylitis, osteoporosis, rheumatoid arthritis (RA), psoriatic arthritis, chronic obstructive pulmonary disease (COPD), atherosclerosis, pulmonary arterial hypertension, pyridoxine-dependent epilepsy, atopic dermatitis, atopic eczema, rosacea, multiple sclerosis (MS), systemic lupus erythematosus (SLE), lupus nephritis, sepsis, eosinophilic esophagitis, chronic kidney disease (CKD), fibrotic renal disease, chronic eosinophilic pneumonia, extrinsic allergic alveolitis, pre-eclampsia, endometriosis, polycystic ovary syndrome (PCOS), reduced female fertility, reduced sperm viability and motility, or cyclophosphamide-induced hemorrhagic cystitis.

In some embodiments, the disease, disorder, or condition for treatment with the compounds of the disclosure is lung-based chronic obstructive pulmonary disease (COPD), interstitial lung disease (ILD), idiopathic pulmonary fibrosis (IPF), cystic fibrosis (CF), emphysema due to alpha-1 antitrypsin deficiency, or pulmonary arterial hypertension (PAH).

In some embodiments, the disease, disorder, or condition for treatment with the compounds of the disclosure is light chain deposition disease, IgA nephropathy, end stage renal disease, gout, pseudogout, diabetic nephropathy, diabetic neuropathy, traumatic brain injury, noise-induced hearing loss, Alzheimer's Disease, Parkinson's Disease, Huntington Disease, amyotrophic lateral sclerosis, primary biliary cirrhosis, primary sclerosing cholangitis, uterine leiomyoma, sarcoidosis, or chronic kidney disease.

In some embodiments, the disease, disorder, or condition for treatment with the compounds of the disclosure is an ocular inflammatory disorder. In some embodiments, the ocular inflammatory disorder is diabetic macular edema (DME), atopic keratoconjunctivitis (AKC), vernal keratoconjunctivitis (VKC), age-related macular degeneration (AMD), dry eye disease (DED), allergic conjunctivitis (AC), dry eye disease with allergic conjunctivitis, noninfectious anterior uveitis, posterior uveitis, pan-uveitis, post-surgical ocular pain and inflammation. In some embodiments, the disease, disorder, or condition is one of those described in WO 2019/075136, which is hereby incorporated by reference.

In some embodiments, the dose of the compound or pharmaceutically acceptable salt thereof is about 10 mg to about 10,000 mg per day.

In some embodiments, the dose of the compound or pharmaceutically acceptable salt thereof is about 10 mg to about 7500 mg per day.

In some embodiments, the dose of the compound or pharmaceutically acceptable salt thereof is about 50 mg to about 3600 mg per day.

In some embodiments, the dose of the compound or pharmaceutically acceptable salt thereof is about 150 mg to about 1200 mg per day.

In some embodiments, the dose of the compound or pharmaceutically acceptable salt thereof is about 250 mg to about 2400 mg per day.

In some embodiments, the dose of the compound or pharmaceutically acceptable salt thereof is about 600 mg to about 5000 mg per day.

In some embodiments, the dose of the compound or pharmaceutically acceptable salt thereof is about 1000 mg to about 7500 mg per day.

In some embodiments, the dose of the compound or pharmaceutically acceptable salt thereof is about 400 mg to about 1200 mg per day.

In some embodiments, the dose of the compound or pharmaceutically acceptable salt thereof is about 500 mg to about 1000 mg per day.

In some embodiments, the dose of the compound or pharmaceutically acceptable salt thereof is about 300 mg to about 1000 mg per day.

In some embodiments, the dose of the compound or pharmaceutically acceptable salt thereof is about 400 mg to about 800 mg per day.

In some embodiments, the dose of the compound or pharmaceutically acceptable salt thereof is about 500 mg to about 700 mg per day.

In some embodiments, the dose of the compound or pharmaceutically acceptable salt thereof is about 600 mg to about 1200 mg per day.

In some embodiments, the dose of the compound or pharmaceutically acceptable salt thereof is about 250 mg to about 2400 mg per day.

In some embodiments, the dose of the compound or pharmaceutically acceptable salt thereof is about 600 mg to about 5000 mg per day.

In some embodiments, the dose of the compound or pharmaceutically acceptable salt thereof is about 1000 mg to about 7500 mg per day.

In some embodiments, the compound or pharmaceutically acceptable salt thereof is administered once, twice, thrice, or four times per day. In some embodiments, the compound or pharmaceutically acceptable salt thereof is administered twice per day.

In some embodiments, the dose of the compound or pharmaceutically acceptable salt thereof is about 600 mg BID (i.e., twice per day); 1.2 g BID; or about 2.4 g BID.

In some embodiments, the dose of the compound or pharmaceutically acceptable salt thereof is about 200 mg BID, 300 mg BID, 400 mg BID, 500 mg BID, 600 mg BID, 700 mg BID, or about 800 mg BID.

In some embodiments, the dose of the compound or pharmaceutically acceptable salt thereof is about 300 mg BID.

In some embodiments, the dose of the compound or pharmaceutically acceptable salt thereof is about 10 mg, 25 mg, 50 mg, 75 mg, 100 mg, 125 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3500 mg, 4000 mg, 5500 mg, 6000 mg, 6500 mg, 7000 mg, 7500 mg, or about 8000 mg per day.

In some embodiments, the dose of the compound or pharmaceutically acceptable salt thereof is administered systemically.

In some embodiments, the dose of the compound or pharmaceutically acceptable salt thereof is administered orally.

In some embodiments, the dose of the compound or pharmaceutically acceptable salt thereof is administered to the patient in a fasted state. In some embodiments, the patient has consumed no food for at least 2 hours prior to dosing and at least 1 hour after dosing.

In some embodiments, the compound is I-1 or a pharmaceutically acceptable salt thereof. In some embodiments, the compound is I-2 or a pharmaceutically acceptable salt thereof.

In some embodiments, the compound reduces systemic inflammation in the patient.

In some embodiments, the compound reduces plasma levels of a biomarker selected from IL-1, IL-6, IL-10, and tumor necrosis factor alpha. In some embodiments, the compound reduces plasma levels of a biomarker selected from a RASP. In some embodiments, the RASP is malondialdehyde (MDA) and/or 4-hydroxynonenal (4-HNE).

In some embodiments, the method further comprises a reduction in the level of a reactive aldehyde species (RASP) in the patient's blood, such as malondialdehyde (MDA) or 4-hydroxynonenal (HNE).

In some embodiments, the level of RASP is reduced by at least 30%, at least 40%, or at least 50%. In some embodiments, the level of RASP is reduced by about 30% to 75%. In some embodiments, the level of RASP is reduced by about 20% to about 60%, or about 20% to about 50%, or about 20% to about 30%.

In some embodiments, the pharmaceutical composition is a liquid. In some embodiments, the pharmaceutical composition is administered as a liquid via nasogastric tube.

In some embodiments, the method further comprises administering to the patient an effective amount of a second therapeutic agent suitable for treating ARDS.

In some embodiments, the second therapeutic agent is an anti-inflammatory agent selected from a steroid, anti-GM-CSF antibody, and a lung surfactant.

Chronic cough, pneumonia, and pulmonary sepsis are clinically distinct respiratory diseases, disorders, or conditions. Chronic cough is generally defined as cough lasting longer than 8 weeks and excluding cough with an underlying fever, such as from a bacterial or viral infection; chronic obstructive pulmonary disease (COPD) and other non-asthmatic pulmonary diseases; cancer of the lung or esophagus; pneumonia; interstitial lung disease; and obstructive sleep apnea. Pneumonia is an infection of the lungs by a pathogen, such as a bacteria, virus, or fungi. It is distinguished from Acute Respiratory Distress Syndrome, which can be caused by acute injury to the lung unrelated to infection by a pathogen. Pneumonia is usually diagnosed by a combination of clinical history, physical examination and/or laboratory tests, and clinical diagnosis from a chest X-ray (CXR), which can distinguish pneumonia from other respiratory tract infections. Pulmonary sepsis also affects the lungs but can arise from sepsis due to the sensitivity of the lungs and because sepsis can develop from infection of the lungs by a pathogen.

Alcohol induced hepatitis, minimal change disease, and focal segmental glomerulosclerosis affect the liver or kidneys rather than the lungs. Alcohol induced hepatitis is attributed to chronic abuse of alcohol, and is characterized by injury to the liver. Defining characteristics include hyperbilirubinemia and levels of liver function markers aspartate aminotransferase (AST) and alanine aminotransferase (ALT). Minimal change disease and focal segmental glomerulosclerosis are diseases, disorders, or conditions affecting the kidney. Both minimal change disease and focal segmental glomerulosclerosis are within the broader disorder of nephrotic syndrome, and are characterized by proteinuria. Minimal change disease can progress into focal segmental glomerulosclerosis, where the latter involve injury and scarring to the kidney in a focal, segmental pattern.

In some embodiments, the pharmaceutical compositions described herein are used for the treatment, prevention, and/or reduction of a risk of respiratory disease, disorder, or condition selected from chronic cough, atopic asthma, allergic rhinitis, sinusitis, hay fever, pneumonia, and pulmonary sepsis, or an organ disease, disorder, or condition selected from alcohol induced hepatitis, minimal change disease, and focal segmental glomerulosclerosis.

As noted above, in one aspect the present disclosure provides a method of treating, preventing, and/or reducing of a risk of respiratory disease, disorder, or condition selected from chronic cough, atopic asthma, allergic rhinitis, sinusitis, hay fever, pneumonia, and pulmonary sepsis, or an organ disease, disorder, or condition selected from alcohol induced hepatitis, minimal change disease, and focal segmental glomerulosclerosis, the method comprising administering an effective amount of a pharmaceutical composition described herein.

In some embodiments, the present disclosure provides use of the pharmaceutical composition described herein in the manufacture of a medicament for the treatment, prevention, and/or reduction of a risk of respiratory disease, disorder, or condition selected from chronic cough, atopic asthma, allergic rhinitis, sinusitis, hay fever, pneumonia, and pulmonary sepsis, or an organ disease, disorder, or condition selected from alcohol induced hepatitis, minimal change disease, and focal segmental glomerulosclerosis.

In some embodiments, the compound for use in treating, preventing, and/or reducing risk of a respiratory disease, disorder, or condition selected from chronic cough, atopic asthma, allergic rhinitis, sinusitis, hay fever, pneumonia, and pulmonary sepsis, or an organ disease, disorder, or condition selected from alcohol induced hepatitis, minimal change disease, and focal segmental glomerulosclerosis, is compound I-1, or a pharmaceutically acceptable salt thereof.

In some embodiments, a method of the disclosure is directed to treatment of chronic cough. In some embodiments, a method of treating or reducing the risk of chronic cough comprises administering to a patient in need thereof an effective amount of a pharmaceutical composition disclosed herein. Generally, chronic cough is characterized as cough lasting greater than 8 weeks duration (see, e.g., Irwin et al., Chest, 2018; 153(1):196-209; Morice, A. H., European Respiratory J., 2004; 24:481-492). Chronic cough can be triggered by and/or arise from different underlying causes, such as asthma, gastroesophageal reflux disease (GERD), non-asthmatic eosinophilic bronchitis (NAEB), and upper airway cough syndrome, otherwise known as postnasal drip syndrome. A differential diagnosis of chronic cough excludes cough accompanied by fever, such as from a bacterial or viral infection; chronic obstructive pulmonary disease (COPD) and other non-asthmatic pulmonary diseases; cancer of the lung or esophagus; pneumonia; interstitial lung disease; and obstructive sleep apnea (see, e.g., Perotin et al., Ther Clin Risk Manag, 2018: 14:1041-1051).

In some embodiments, the chronic cough for treatment is associated with upper airway cough syndrome.

In some embodiments, the chronic cough for treatment is associated with gastroesophageal reflux disease or laryngopharyngeal reflux disease.

In some embodiments, the chronic cough for treatment is associated with asthma.

In some embodiments, the chronic cough for treatment is associated with non-asthmatic eosinophilic bronchitis.

In some embodiments, the patient treated has a history of one or more of the following: treatment with angiotensin-converting enzyme (ACE) inhibitor, smoking, asthma, exposure to environmental respiratory irritants, and bronchitis.

In some embodiments, a method of the disclosure is directed to treatment of pneumonia. In some embodiments, the pneumonia is not associated or concurrent with acute respiratory distress syndrome (ARDS).

In some embodiments, the patient treated has pneumonia, wherein the pneumonia has a differential diagnosis from eosinophilic pneumonia (i.e., the pneumonia is not associated with eosinophilic pneumonia).

In some embodiments, the pneumonia treated is community-acquired pneumonia.

In some embodiments, the pneumonia treated is nocosomial pneumonia.

In some embodiments, the pneumonia treated is bacterial pneumonia or viral pneumonia.

In some embodiments, the patient treated is diagnosed with a bacterial infection by, among others, *Streptococcus pneumoniae, Haemophilus influenzae, S. aureus*, Group A streptococci, *Moraxella catarrhalis, Klebsiella pneumoniae, Pseudomonas aeruginosa, Legionella* spp, *Mycoplasma pneumoniae, Chlamydia pneumoniae*, or *C. psittaci*.

In some embodiments, the patient treated is diagnosed with a viral infection by influenza virus (e.g., influenza A or influenza B), respiratory syncytial virus (RSV), parainfluenza, metapneumovirus, coronavirus, rhinovirus, hantavirus, or adenovirus.

In some embodiments, the pneumonia treated is lobar pneumonia.

In some embodiments, the pneumonia treated is upper, middle or lower lobe pneumonia.

In some embodiments, the pneumonia treated is focal pneumonia, alveolar pneumonia, or interstitial pneumonia.

In some embodiments, the pneumonia treated is bronchial pneumonia.

In some embodiments, the method of the disclosure is directed to treatment of atopic asthma. In some embodiments, the method of the disclosure is directed to treatment of allergic rhinitis.

In some embodiments, a method of the disclosure is directed to treatment or reducing the risk of sepsis. In some embodiments, a method of the disclosure is directed to treatment of pulmonary sepsis or sepsis-induced lung injury. In some embodiments, a method of treating or reducing the risk of pulmonary sepsis or sepsis-induced lung injury comprises administering to a patient in need thereof an effective amount of a compound disclosed herein, such as compound I-1 or a pharmaceutically acceptable salt thereof. Generally, pulmonary sepsis or sepsis induced lung injury is characterized as lung injury arising from sepsis. The lung is the organ most often affected by sepsis primarily because pneumonia is often the starting point of the septic process, and disseminated infectious process is associated with a systemic inflammatory response (SIRS) in which the first organ to be affected is usually the lung.

In some embodiments, the pulmonary sepsis or sepsis induced lung injury treated is without (i.e., not associated with) acute respiratory distress syndrome (ARDS).

In some embodiments, a method of the disclosure is directed to treatment of alcohol poisoning. In some embodiments, a method of the disclosure is directed to treatment of alcohol-induced hepatitis. In some embodiments, a method of treating or reducing the risk of alcohol-induced hepatitis comprises administering to a patient in need thereof an effective amount of a compound disclosed herein, such as compound I-1 or a pharmaceutically acceptable salt thereof. Generally, alcohol-induced hepatitis includes liver injury and associated inflammatory condition arising from chronic alcohol abuse. A prominent feature or marker for the disease is hyperbilirubinemia. In some embodiments, alcohol-induced hepatitis is distinguished from cirrhosis in that the former appears reversible while the latter is a permanent injury to the liver.

In some embodiments, the alcohol-induced hepatitis is without cirrhosis (i.e., not accompanied by cirrhosis).

In some embodiments, the patient treated for alcohol-induced hepatitis is determined to have elevated levels of aspartate aminotransferase (AST) and/or alanine aminotransferase (ALT) as compared to levels in a control group not afflicted with alcohol induced hepatitis.

In some embodiments, the levels of AST in the control group (i.e., without alcohol induced hepatitis) is about 8 to 48 IU/L and the levels of ALT in the control group is about 7 to 55 IU/L.

In some embodiments, the patient treated has an AST: ALT ratio of greater than 2:1. This ratio is characteristic in patients with alcoholic liver disease. Patients with a history of alcohol abuse but no significant alcoholic hepatitis or cirrhosis of the liver usually have an AST/ALT ratio less than 1.0.

In some embodiments, a method of the disclosure is directed to treatment of minimal change disease, sometimes referred to as lipoid nephrosis or nil disease. In some embodiments, a method of treating or reducing the risk of minimal change disease comprises administering to a patient in need thereof an effective amount of a compound disclosed herein. Generally, minimal change disease is a kidney disease arising from a histopathologic lesion in the glomerulus and is characterized by proteinuria leading to edema and intravascular volume depletion. Minimal change disease is a common form of nephrotic syndrome.

In some embodiments, the minimal change disease treated is associated with nephrotic syndrome.

In some embodiments, the minimal change disease treated is concurrent with proteinuria, particularly excessive proteinuria.

Minimal change disease can also advance to focal segmental glomerulosclerosis. Accordingly, in some embodiments, a method of the disclosure is directed to treatment of focal segmental glomerulosclerosis (FGS). In some embodiments, a method of treating or reducing the risk of FGS comprises administering to a patient in need thereof an effective amount of a compound disclosed herein. Generally, FGS describes both a common lesion in progressive kidney disease and excessive proteinuria and podocyte injury. The injury and scarring of the kidney is characterized by focal involvement in a segmental pattern. FGS is also a common cause of nephrotic syndrome.

In some embodiments, the FSGS treated is primary FSGS.

In some embodiments, the FSGS treated is secondary FSGS.

In some embodiments, the FSGS treated is familial FSGS. Autosomal dominant FSGS is associated with mutations in the gene encoding Inverted Formin 2 (INF2), alpha-actinin-4 gene ACTN4; the gene encoding TRPC6 cation channel protein; and the gene ARHGAP24 encoding the FilGAP protein (see, e.g., Pollak, M. R., Adv Chronic Kidney Dis., 2014, 21(5): 422-425). Recessive forms of FSGS are associated with mutations in the gene NPHS1 encoding nephrin; and the gene PLCE1 encoding phospholipase C epsilon 1 (see, e.g., Pollak, supra).

In some embodiments, the FSGS treated is associated with nephrotic syndrome.

In some embodiments, the FSGS treated is concurrent with kidney failure and/or proteinuria, particularly excessive proteinuria.

In some embodiments, the patient treated for FSGS has a prior history of minimal change disease.

In some embodiments, the pharmaceutical composition of the present disclosure comprising a compound or pharmaceutically acceptable salt thereof described herein is administered systemically to treat the indications described herein. In some embodiments, the pharmaceutical composition is administered orally.

In some embodiments, the pharmaceutical composition is a liquid. In some embodiments, the pharmaceutical composition is administered as a liquid via nasogastric tube.

In some embodiments, the compound is I-1 or a pharmaceutically acceptable salt thereof. In some embodiments, the compound is I-2 or a pharmaceutically acceptable salt thereof.

4. Pharmaceutical Compositions, Administration, and Dosages

The compounds and compositions, according to the methods of the present invention, are administered using any amount and any route of administration effective for treating or lessening the severity of a disease described above. The exact amount required will vary from subject to subject, depending on the species, age, and general condition of the subject, the severity of the infection, the particular agent, its mode of administration, and the like. Compounds of the invention are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intrathecally, transdermally, transmucosally, opthalmically, via inhalation, intravaginally, intraperitoneally, topically (as by powders, ointments, or drops), buccally, intranasally, as an oral or nasal spray, or the like, depending on the severity of the disease being treated. In certain embodiments, the compounds of the invention are administered orally or parenterally at dosage levels of about 0.01 mg/kg to about 50 mg/kg and for example from about 1 mg/kg to about 25 mg/kg, of subject body weight per day, one or more times a day, to obtain the desired therapeutic effect.

A unit dosage form of the invention can be formulated for oral administration. Pharmaceutical compositions/formulations that are suitable for oral administration can be provided as discrete dosage forms, such as, but not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In some embodiments, such dosage forms contain predetermined amounts of active ingredients, and may be prepared by methods of pharmacy known to those skilled in the art. See generally, Remington's Pharmaceutical Sciences, 18$^{th}$ ed., Mack Publishing, Easton Pa. (1990). As used herein, oral administration also includes buccal, lingual, and sublingual administration.

In some embodiments, the formulation further comprises one or more pharmaceutically acceptable excipients or carriers.

A person of ordinary skill would recognize that pharmaceutical formulation ingredients may serve multiple purposes within a formulation. Accordingly, a person of ordinary skill would recognize that certain formulation components may be classified according to multiple functions (e.g., a component may be both a filler and a binder).

In some embodiments, a unit dosage form provided herein are prepared by combining the active ingredients in an intimate admixture with one or more pharmaceutically acceptable excipients or carriers, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide, according to conventional pharmaceutical compounding techniques. Excipients or carriers can take a wide variety of forms depending on the form of preparation desired for administration. For example, excipients or carriers suitable for use in oral liquid or aerosol dosage forms include, but are not limited to, water, glycols, oils, alcohols, flavoring agents, preservatives, and coloring agents. Examples of excipients or carriers suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In some embodiments, the active ingredient, such as compound I-1 or a pharmaceutically acceptable salt thereof, is incorporated into the pharmaceutical composition as spray-dried powder or granules. The use of spray-drying to produce powders from fluid feed stocks is well known, with applications ranging from powdered milk to bulk chemicals and pharmaceuticals. See U.S. Pat. No. 4,187,617 and Mujumbar et al., 91 Drying, pages 56-73 (1991). The use of spray-drying to form solid amorphous dispersions of drugs and concentration-enhancing polymers is also known. See commonly owned European Patent Applications Nos. 0 901 786, 1 027 886, 1 027 887, 1 027 888, and commonly owned PCT Applications Nos. WO 00/168092 and WO 00/168055, each of which is hereby incorporated by reference. A typical spray-drying apparatus comprises a drying chamber, atomizing means for atomizing a solvent-containing liquid feed into the drying chamber, a source of heated drying gas directed into the drying chamber and dried product collection means for separating the dried product from the cooled drying gas and vaporized solvent stream following its exit from the drying chamber. Examples of such apparatus include Niro Models PSD-1, PSD-2 and PSD-4 (Niro A/S, Soeborg, Denmark).

The spray-dried powder or granules generally include the active compound in combination with a polymer such as a concentration-enhancing polymer. One class of polymers suitable for use with the present invention comprises non-ionizable (neutral) non-cellulosic polymers. Exemplary polymers include: vinyl polymers and copolymers having at least one substituent selected from the group consisting of hydroxyl, alkylacyloxy, and cyclicamido; polyvinyl alcohols that have at least a portion of their repeat units in the unhydrolyzed (vinyl acetate) form; polyvinyl alcohol polyvinyl acetate copolymers; polyvinyl pyrrolidone; and polyethylene polyvinyl alcohol copolymers; and polyoxyethylene-polyoxypropylene copolymers.

Exemplary neutral non-cellulosic polymers are comprised of vinyl copolymers of at least one hydrophilic, hydroxyl-containing repeat unit and at least one hydrophobic, alkyl- or aryl-containing repeat unit. Such neutral vinyl copolymers are termed "amphiphilic hydroxyl-functional vinyl copolymers." Amphiphilic hydroxyl-functional vinyl copolymers are believed to provide high concentration enhancements due to the amphiphilicity of these copolymers which provide both sufficient hydrophobic groups to interact with the hydrophobic, low-solubility drugs and also sufficient hydrophilic groups to have sufficient aqueous solubility for good dissolution. The copolymeric structure of the amphiphilic hydroxyl-functional vinyl copolymers also allows their hydrophilicity and hydrophobicity to be adjusted to maximize performance with a specific low-solubility drug.

Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGIT™ series manufactured by Rohm Tech Inc., of Malden, Mass.; amine-functionalized polyacrylates and polymethacrylates; proteins such as gelatin and albumin; and carboxylic acid functionalized starches such as starch glycolate.

Non-cellulosic polymers that are amphiphilic are copolymers of a relatively hydrophilic and a relatively hydrophobic monomer. Examples include acrylate and methacrylate copolymers. Exemplary commercial grades of such copolymers include the EUDRAGIT™ series, which are copolymers of methacrylates and acrylates.

An additional class of polymers comprises ionizable and neutral (or non-ionizable) cellulosic polymers with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate groups attached via ester linkages to a significant fraction of the cellulosic polymer's hydroxyl groups. Generally, the degree of substitution of each substituent group can range from 0.05 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate-substituted, the phthalate degree of substitution is 3. Also included within each polymer family type are cellulosic polymers that have additional substituents added in relatively small amounts that do not substantially alter the performance of the polymer.

Amphiphilic cellulosics comprise polymers in which the parent cellulosic polymer has been substituted at any or all of the 3 hydroxyl groups present on each saccharide repeat unit with at least one relatively hydrophobic substituent. Hydrophobic substituents may be essentially any substituent that, if substituted to a high enough level or degree of substitution, can render the cellulosic polymer essentially aqueous-insoluble. Examples of hydrophobic substituent include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic regions of the polymer can be either those portions that are relatively unsubstituted, since the unsubstituted hydroxyls are themselves relatively hydrophilic, or those regions that are substituted with hydrophilic substituents. Hydrophilic substituents include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary nonionizable cellulosic polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

An exemplary class of neutral cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

A particular class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester-linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic substituent may itself be ionizable, such as phthalate or trimellitate substituents.

Exemplary cellulosic polymers that are at least partially-ionized at physiologically relevant pHs include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, carboxymethyl ethyl cellulose, ethyl carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Exemplary cellulosic polymers that meet the definition of amphiphilic, having hydrophilic and hydrophobic regions include polymers such as cellulose acetate phthalate and cellulose acetate trimellitate where the cellulosic repeat units that have one or more acetate substituents are hydrophobic relative to those that have no acetate substituents or have one or more ionized phthalate or trimellitate substituents.

A further subset of cellulosic ionizable polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxylpropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another subset of cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, hydroxyethyl cellulose acetate succinate and carboxymethyl ethyl cellulose. Of these cellulosic polymers that are at least partially ionized at physiologically relevant pHs, the inventors have found the following to be most preferred: hydroxypropyl methyl cellulose acetate succinate, hydroxypropyl methyl cellulose phthalate, cellulose acetate phthalate, cellulose acetate trimellitate and carboxymethyl ethyl cellulose. The most preferred is hydroxypropyl methyl cellulose acetate succinate (HPMCAS).

Another class of polymers consists of neutralized acidic polymers. By "neutralized acidic polymer" is meant any acidic polymer for which a significant fraction of the "acidic moieties" or "acidic substituents" have been "neutralized"; that is, exist in their deprotonated form. By "neutralized acidic cellulosic polymers" is meant any cellulosic "acidic polymer" in which a significant fraction of the "acidic moieties" or "acidic substituents" have been "neutralized." By "acidic polymer" is meant any polymer that possesses a significant number of acidic moieties. In general, a significant number of acidic moieties would be greater than or equal to about 0.1 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer that has a pKa of less than about 10. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents."

The amount of concentration-enhancing polymer relative to the amount of drug present in the spray-dried dispersions depends on the drug and concentration-enhancing polymer and may vary widely from a drug-to-polymer weight ratio of 0.01 to 5. However, in most cases, except when the drug dose is quite low, e.g., 25 mg or less, it is preferred that the drug-to-polymer ratio is greater than 0.05 and less than 2.5 and often the enhancement in drug concentration or relative bioavailability is observed at drug-to-polymer ratios of 1 or less or for some drugs even 0.2 or less. In cases where the drug dose is about 25 mg or less, the drug-to-polymer weight ratio may be significantly less than 0.05. In general, regardless of the dose, enhancements in drug concentration or relative bioavailability increase with decreasing drug-to-polymer weight ratio. However, due to the practical limits of keeping the total mass of a tablet, capsule or suspension low, it is often desirable to use a relatively high drug-to-polymer ratio as long as satisfactory results are obtained. The maximum drug:polymer ratio that yields satisfactory results varies from drug to drug and is best determined in the in vitro and/or in vivo dissolution tests described below.

A spray-dried solid as described herein can be a solid dispersion that contains a compound described herein and a pharmaceutically acceptable polymer. Certain compounds described herein generally have low aqueous solubility, and their absorption in vivo is dissolution-rate limited. A solid dispersion containing a compound can increase the compound solubility/dissolution, thereby improving the bioavailability of the compound.

The term "solid dispersion" herein refers to the dispersion of a pharmaceutically active ingredient, e.g., the compound described herein, in an inert polymer matrix at solid state. A solid dispersion can be prepared by methods well known in the art, e.g., spray-drying or hot-melt extrusion. The matrix can be either crystalline or amorphous. A solid dispersion contains a co-precipitate of a pharmaceutically active ingredient and one or more water-soluble polymers, in which the pharmaceutically active ingredient is dispersed uniformly within a polymer matrix formed from the polymers. The pharmaceutically active ingredient can be present in an amorphous state, a crystalline dispersed form, or a combination thereof. It can also be finely dispersed or dissolved as single molecules in the polymer matrix. The solid dispersion is typically prepared by a spray-drying method or a hot-melt extrusion method.

The method for preparing the solid dispersion includes steps of (i) mixing a compound described herein and a polymer in an organic solvent to provide a feeder solution and (ii) spray-drying the feeder solution through a nozzle as a fine spray into a chamber where the solvent is evaporated quickly to generate particles containing the compound and polymer. Following formation of a solid dispersion, the resulting spray-dried particle can undergo a secondary drying step to remove residual solvents. The secondary drying step can take place in a static dryer or an agitated dryer. Gas, humidified gas, vacuum can be applied to the secondary drying step and such application is useful in more rapidly removing residual solvents that remain in the spray-dried particle.

Any organic solvent that can easily dissolve or disperse the compound and the polymer described above can be used. Examples of the organic solvent include lower carbon-number alcohols, e.g., methanol, ethanol, propanol, and isopropanol; ketones, e.g., methylethyl ketone and butanone; and a combination thereof.

In some embodiments, the pharmaceutically acceptable excipients and carriers are selected from fillers, binders, diluents, disintegrants, glidants, and lubricants.

In some embodiments, the present invention provides a capsule or tablet which comprises a provided pharmaceutical composition in the form of a solid dosage form. In some embodiments, the present invention provides a capsule. In some embodiments, the present invention provides a tablet.

In certain embodiments, the dosage form is a tablet, wherein the tablet is manufactured using standard, art-recognized tablet processing procedures and equipment. In certain embodiments, the method for forming the tablets is direct compression of a powdered, crystalline and/or granular composition comprising a solid form provided herein, alone or in combination with one or more excipients or carriers, such as, for example, carriers, additives, polymers, or the like. In certain embodiments, as an alternative to direct compression, the tablets may be prepared using wet granulation or dry granulation processes. In certain embodiments, the tablets are molded rather than compressed, starting with a moist or otherwise tractable material. In certain embodiments, compression and granulation techniques are used.

In certain embodiments, the dosage form is a capsule, wherein the capsules may be manufactured using standard, art-recognized capsule processing procedures and equipments. In certain embodiments, soft gelatin capsules may be prepared in which the capsules contain a mixture comprising a solid form provided herein and vegetable oil or non-aqueous, water miscible materials, such as, for example, polyethylene glycol and the like. In certain embodiments, hard gelatin capsules may be prepared containing granules of solid forms provided herein in combination with a solid pulverulent carrier, such as, for example, lactose, saccharose, sorbitol, mannitol, potato starch, corn starch, amylopectin, cellulose derivatives, or gelatin. In certain embodiments, a hard gelatin capsule shell may be prepared from a capsule composition comprising gelatin and a small amount of plasticizer such as glycerol. In certain embodiments, as an alternative to gelatin, the capsule shell may be made of a carbohydrate material. In certain embodiments, the capsule composition may additionally include polymers, colorings, flavorings and opacifiers as required. In certain embodiments, the capsule comprises HPMC.

In some embodiments, the pharmaceutical composition comprises one or more fillers. In certain embodiments, the filler is selected from ammonium aliginate, calcium carbonate, calcium lactate, calcium phosphate, calcium silicate, calcium sulfate, cellulose acetate, compressible sugar (e.g., lactose, glucose, and sucrose), corn starch, dextrates, erythritol, ethyl cellulose, glyceryl palmitostearate, isomalt, kaolin, magnesium carbonate, magnesium oxide, maltodextrin, medium-chain triglycerides, microcrystalline cellulose, pre-gelatinized starch, polydextrose, polymethacrylates, silicic acid, simethicone, sodium alginate, sodium chloride, sorbitol, starch, sugar spheres, sulfobutylether β-cyclodextrin, talc, tragacanth, trehalose, and xylitol, or a combination thereof.

In some embodiments, the filler is selected from talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

In some embodiments, the filler is microcrystalline cellulose. In some embodiments, the filler is lactose. In some embodiments, the filler is starch. In some embodiments, the filler is a combination of starch and lactose. In some embodiments, the filler is a combination of lactose and microcrystalline cellulose. In some embodiments, the filler is a combination of two or three components recited above. In some embodiments, the filler comprises at least microcrystalline cellulose, lactose, and mannitol.

In certain embodiments, dosage forms provided herein comprise one or more diluents. Diluents may be used, e.g., to increase bulk so that a practical size tablet or capsule is ultimately provided. Suitable diluents include dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol and talc, among others. Diluents also include, e.g., ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethylacrylates, simethicone, sodium alginate, sodium chloride, sorbitol, starch, pregelatinized starch, sucrose, sulfobutylether-β-cyclodextrin, talc, tragacanth, trehalose, and xylitol.

In some embodiments, the pharmaceutical composition comprises one or more binders. Binders may be used, e.g., to impart cohesive qualities to a tablet or a capsule, and thus ensure that the formulation remains intact after compression. In some embodiments, the binder is selected from acacia gum, agar, alginic acid, calcium carbonate, calcium lactate, carbomers (e.g., acrylic acid polymer, carboxy polymethylene, polyacrylic acid, carboxyvinyl polymer), carboxymethylcellulose sodium, carrageenan, cellulose acetate phthalate, *ceratonia*, chitosan, copovidone, corn starch, cottonseed oil, dextrates, dextrin, dextrose, ethylcellulose, gelatin, glyceryl behenate, guar gum, hydrogenated vegetable oil type I, hydroxyethylcellulose, hydroxyethylmethyl cellulose, hydroxypropyl cellulose, hydroxypropyl methylcellulose, hypromellose, inulin, lactose, magnesium aluminum silicate, maltodextrin, maltose, methylcellulose, microcrystalline cellulose, pectin, poloxamer, polycarbohil, polydextrose, polyethylene oxide, polymetharylates, polyvinylpyrrolidone, pre-gelatinized starch, povidone, sodium alginate, starch, stearic acid, sucrose, tricaprylin, vitamin E polyethylene glycol succinate, and zein.

Suitable binders include, but are not limited to, starch (including potato starch, corn starch, and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone (PVP), cellulosic polymers (including hydroxypropyl cellulose (HPC), hydroxypropylmethylcellulose (HPMC), methyl cellulose, ethyl cellulose, hydroxyethyl cellulose (HEC), carboxymethyl cellulose and the like), veegum, carbomer (e.g., carbopol), sodium, dextrin, guar gum, hydrogenated vegetable oil, magnesium aluminum silicate, maltodextrin, polymethacrylates, povidone (e.g., KOLLIDON, PLASDONE), microcrystalline cellulose, among others. Binding agents also include, e.g., acacia, agar, alginic acid, cabomers, carrageenan, cellulose acetate phthalate, *ceratonia*, chitosan, confectioner's sugar, copovidone, dextrates, dextrin, dextrose, ethylcellulose, gelatin, glyceryl behenate, guar gum, hydroxyethyl cellulose, hydroxyethylmethyl cellulose, hydroxypropyl cellulose, hydroxypropyl starch, hypromellose, inulin, lactose, magnesium aluminum silicate, maltodextrin, maltose, methylcellulose, poloxamer, polycarbophil, polydextrose, polyethylene oxide, polymethylacrylates, povidone, sodium alginate, sodium carboxymethylcellulose, starch, pregelatinized starch, stearic acid, sucrose, and zein.

Suitable forms of microcrystalline cellulose include, but are not limited to, the materials sold as AVICEL-PH-101, AVICEL-PH-103 AVICEL RC-581, AVICEL-PH-105 (FMC Corporation, Marcus Hook, Pa.), and mixtures thereof. In some embodiment, a specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

In some embodiments, the pharmaceutical composition comprises one or more disintegrants. In certain embodiments, the disintegrant is selected from alginic acid, calcium alginate, carboxymethylcellulose calcium, carboxymethylcellulose sodium, cellulose, chitosan, colloidal silicon dioxide, corn starch, croscarmellose sodium, crospovidone, docusate sodium, glycine, guar gum, hydroxypropyl cellulose, magnesium aluminum silicate, methylcellulose, microcrystalline cellulose, pre-gelatinized starch, polacrilin potassium, povidone, silicates, sodium aliginate, sodium carbonate, and sodium starch glycolate.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof.

In some embodiments, the pharmaceutical composition comprises one or more surfactants. In some embodiments, the surfactant is selected from polyoxyethylene (20) sorbitan monolaurate (e.g., Tween-20), polyoxyethylene (20) sorbitan monooleate (e.g., Tween-80), sodium lauryl sulfate, and sodium dodecyl sulfate.

In some embodiments, the pharmaceutical composition comprises one or more pore formers. In some embodiments, the pore former is selected from hydroxypropylcellulose, hydroxypropylmethylcellulose, polyethyleneglycol, poloaxamer 188, povidone (e.g., Kollidon K25/K30), or sugar (e.g., glucose, mannose, fructose, and sucrose).

In some embodiments, the pharmaceutical composition comprises one or more glidants. In some embodiments, the glidant is selected from calcium phosphate, cellulose, colloidal silicon dioxide, fumed silica, magnesium oxide, magnesium silicate, magnesium stearate, magnesium trisilicate, and talc. Suitable glidants include, but are not limited to, colloidal silicon dioxide, CAB-O-SIL™ (Cabot Co. of Boston, MA), and asbestos-free talc.

In some embodiments, the pharmaceutical composition comprises one or more lubricants. In some embodiments, the lubricant is selected from calcium stearate, glycerin monosterate, glyceryl behenate, glyceryl palmitostearate, hydrogenated castor oil, hydrogenated vegetable oil, light mineral oil, myristic acid, poloxamer, polyethylene glycol, sodium benzoate, sodium chloride, sodium lauryl sulfate, sodium stearyl fumarate, solid polyethylene glycols, stearic acid, and talc.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof.

In some embodiments, the pharmaceutical composition comprises one or more film coating agents. In some embodiments, the film coating comprises a poly(vinyl alcohol) base. In some embodiments, the film coating includes a coloring agent or pigment. In some embodiments, the film coating is Opadry II® such as Opadry II® yellow.

Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye.

Suitable flavoring agents include, but are not limited to, natural flavors extracted from plants, such as fruits, and synthetic blends of compounds which produce a pleasant taste sensation, such as peppermint and methyl salicylate.

Suitable sweetening agents include, but are not limited to, sucrose, lactose, mannitol, syrups, glycerin, and artificial sweeteners, such as saccharin and aspartame.

Suitable emulsifying agents include, but are not limited to, gelatin, acacia, tragacanth, bentonite, and surfactants, such as polyoxyethylene sorbitan monooleate (Tween-20), polyoxyethylene sorbitan monooleate 80 (Tween-80), and triethanolamine oleate.

Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone.

Suitable preservatives include, but are not limited to, glycerin, methyl and propylparaben, benzoic acid, sodium benzoate, and alcohol.

Suitable wetting agents include, but are not limited to, propylene glycol monostearate, sorbitan monooleate, diethylene glycol monolaurate, and polyoxyethylene lauryl ether.

Suitable solvents include, but are not limited to, glycerin, sorbitol, ethyl alcohol, and syrup.

Suitable non-aqueous liquids utilized in emulsions include, but are not limited to, mineral oil and cottonseed oil.

Suitable organic acids include, but are not limited to, citric and tartaric acid.

Suitable sources of carbon dioxide include, but are not limited to, sodium bicarbonate and sodium carbonate.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

A tablet dosage form can be prepared from the active ingredient in powdered, crystalline, or granular forms, alone or in combination with one or more carriers or excipients described herein, including binders, disintegrants, controlled-release polymers, lubricants, diluents, and/or colorants.

A tablet of the present disclosure can be formulated for rapid, sustained, extended, or modified release.

In some embodiments, a unit dosage form of the invention comprises one or more pharmaceutically acceptable excipients selected from microcrystalline cellulose, lactose monohydrate (modified), croscarmellose sodium, hydroxypropyl cellulose, and magnesium stearate.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, the present invention is directed to a composition, as described herein, comprising a prodrug of a disclosed compound. The term "prodrug," as used herein, means a compound that is convertible in vivo by metabolic means (e.g. by hydrolysis) to a compound. Various general forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). *Design and Application of Prodrugs, Textbook of Drug Design and Development*, Chapter 5, 113-191 (1991), Bundgaard, et al., Journal of Drug Delivery Reviews, 8:1-38(1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is hereby incorporated by reference in its entirety.

For oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrants include, without limitation, starch, methyl cellulose, agar, bentonite, xanthan gum starches, agar, alginic acid or its sodium salt, or effervescent mixtures, croscarmellose or its sodium salt, and the like. Diluents include, e.g., lactose, dextrose, sucrose, mannitol, sorbitol, cellulose and/or glycine.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A therapeutically effective dose, of a compound described herein in an oral formulation, may vary from 0.01 mg/kg to 50 mg/kg patient body weight per day, more particularly 0.01 to 10 mg/kg, which can be administered in single or multiple doses per day. For oral administration, the drug can be delivered in the form of tablets or capsules containing 1 mg to 500 mg of the active ingredient specifically, 1 mg, 5 mg, 10 mg, 20 mg, 50 mg, 100 mg, 250 mg, and 500 mg, or in the forms of tables or capsules containing at least 1%, 2%, 5%, 10%, 15%, 20%, 25%, 30%, 40%, 50% (w/w) of the active ingredient. For example, the capsules may contain 50 mg of the active ingredient, or 5-10% (w/w) of the active ingredient. For example, the tablets may contain 100 mg of the active ingredient, or 20-50% (w/w) of the active ingredient. For example, the tablet may contain, in addition to the active ingredient, a disintegrant or emollient (e.g., croscarmellose or its sodium salt and methyl cellulose), a diluent (e.g., microcrystalline cellulose), and a lubricant (e.g., sodium stearate and magnesium stearate). The drug can be administered on a daily basis either once, twice or more per day.

For administration by inhalation, the compounds can be delivered in the form of an aerosol spray from pressured container or dispenser, which contains a suitable propellant, e.g., a gas such as carbon dioxide, or a nebulizer.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. Penetration enhancers promote the penetration of drugs through the corneal barrier and change the integrity of the epithelial cell layer. Frequently used penetration enhancers in ocular formulations include cyclodextrin, dimethylsulphoxide (DMSO), ethylenediaminetetraacetic acid (EDTA), sodium glycocholate and related cholates, Tween 20 (a non-ionic polysorbate surfactant), Brij 35 (polyoxyethylene lauryl ether), saponins and bile salts. Generally, penetration enhancers such as EDTA and cholates transiently loosen the tight junctions between adjacent cells of the corneal epithelium. Thus, penetration enhancers, when applied topically to the eye, have been successfully applied to the delivery of protein and peptides through the corneal epithelium. In some embodiments, a formulation described herein includes a penetration enhancer such as polyoxyethylene-9-lauryl ether, sodium deoxycholate, sodium glycocholate, or sodium taurocholate.

In some embodiments, a pharmaceutically acceptable excipient in an ophthalmic solution or transmucosal formulation of the invention is a cyclodextrin. Cyclodextrins are known to act as permeation enhancers and mucoadhesive agents. In some embodiments, the cyclodextrin is $\alpha$-, $\beta$- or $\gamma$-cyclodextrin. In some embodiments, the cyclodextrin is a pharmaceutically acceptable derivative of a cyclodextrin, including, but not limited to, the hydroxyalkyl derivatives of $\alpha$-, $\beta$- and $\gamma$-cyclodextrin (especially the hydroxyethyl and hydroxypropyl derivatives of $\beta$-cyclodextrin and $\gamma$-cyclodextrin), randomly methylated $\beta$-cyclodextrin, sulfobutylether $\beta$-cyclodextrin, sulfobutylether $\gamma$-cyclodextrin, and the so-called branched 0- and $\gamma$-cyclodextrin derivatives such as glucosyl-$\beta$-cyclodextrin and glucosyl-$\gamma$-cyclodextrin. The natural cyclodextrins are either used alone or in a mixture of two or more cyclodextrins, by way of non-limiting example, a mixture of the $\gamma$-cyclodextrin and the more water-soluble hydroxypropyl $\gamma$-cyclodextrin, or $\gamma$-cyclodextrin and sulfobutylether $\gamma$-cyclodextrin, or $\beta$-cyclodextrin and hydroxypropyl-$\beta$-cyclodextrin, or $\beta$-cyclodextrin and sulfobutylether $\beta$-cyclodextrin.

In some embodiments, a cyclodextrin in an ophthalmic solution or transmucosal formulation of the invention is at a concentration of 0 to 20% w/v. In some embodiments, a cyclodextrin in an ophthalmic solution of the invention is at a concentration of 1 to 18% w/v, 1 to 16% w/v, 1 to 14% w/v, 2 to 12% w/v, 4 to 10% w/v, 5 to 9% w/v, or 6 to 8% w/v. In some embodiments, the cyclodextrin in an ophthalmic solution of the invention is at a concentration of 7% to 11% w/v. In some embodiments, a cyclodextrin in an ophthalmic solution of the invention is at a concentration of about 1% w/v, 2% w/v, 3% w/v, 4% w/v, 5% w/v, 6% w/v, 7% w/v, 8% w/v, 9% w/v, 10% w/v, 11% w/v, 12% w/v, 13% w/v, 14% w/v, 15% w/v, 16% w/v, 17% w/v, 18% w/v, 19% w/v, or 20% w/v.

In some embodiments, a pharmaceutically acceptable excipient in an ophthalmic solution or transmucosal formulation of the invention is sulfobutylether-$\beta$-cyclodextrin, in particular at any of the specified concentrations and ranges of concentrations above, such as about 7% w/v. In some embodiments, a pharmaceutically acceptable excipient in an ophthalmic solution of the invention is hydroxypropyl-β-cyclodextrin, in particular at any of the specified concentrations and ranges of concentrations specified above, such as about 7% w/v.

In some embodiments, an ophthalmic solution of the invention comprises a pharmaceutically acceptable buffering agent. In some embodiments, a pharmaceutically acceptable buffering agent is a phosphate buffer, citrate buffer, tris buffer, histidine buffer or acetate buffer.

In some embodiments, a pharmaceutically acceptable buffering agent is sodium phosphate, dibasic. In some embodiments, a pharmaceutically acceptable buffering agent is sodium phosphate, monobasic. In some embodiments, a pharmaceutically acceptable buffering agent is a mixture of sodium phosphate, dibasic, and sodium phosphate, monobasic. In some embodiments, an ophthalmic solution of the invention comprises about 0.083% w/v sodium phosphate, dibasic, and about 0.017% w/v sodium phosphate, monobasic.

In some embodiments, the ophthalmic solution of the invention is at an approximately neutral pH. In some embodiments, an ophthalmic solution of the invention is at a pH of 6.5 to 8. In some embodiments, an ophthalmic solution of the invention is at a pH of 6.9 to 7.7. In some embodiments, an ophthalmic solution of the invention is at a pH of 7.1 to 7.5. In some embodiments, an ophthalmic solution of the invention is at a pH of about 7.3.

Pharmaceutically acceptable acids and/or bases may be used in the ophthalmic solution to adjust pH. In some embodiments, an ophthalmic solution of the invention comprises a pharmaceutically acceptable acid. In some embodiments, an ophthalmic solution of the invention comprises a pharmaceutically acceptable base. In some embodiments, an ophthalmic solution of the invention comprises a pharmaceutically acceptable acid and base. In some embodiments, a pharmaceutically acceptable acid is hydrochloric acid. In some embodiments, pharmaceutically acceptable base is sodium hydroxide.

In some embodiments, an ophthalmic solution of the invention comprises a tonicity agent. In some embodiments, a tonicity agent is selected from the group consisting of dextrose, potassium chloride, propylene glycol, and sodium chloride. In some embodiments, an ophthalmic solution of the invention comprises a tonicity agent at a concentration of less than about 0.5% w/v. In some embodiments, an ophthalmic solution of the invention comprises a tonicity agent at a concentration of about 0.45%, 0.4%, 0.35%, 0.3%, 0.25%, 0.2%, 0.15%, or 0.10% w/v. In some embodiments, a tonicity agent is sodium chloride.

Parenteral formulations comprising a compound described herein can be prepared in aqueous isotonic solutions or suspensions, and suppositories are advantageously prepared from fatty emulsions or suspensions. The formulations may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional methods, and may contain about 0.1 to 75%, preferably about 1 to 50%, of a compound described herein.

The phrases "parenteral administration" and "administered parenterally" are art-recognized terms, and include modes of administration other than enteral and topical administration, such as by injection, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

Formulations for topical administration to the skin can include, for example, ointments, creams, gels and pastes comprising the primary amine compound in a pharmaceutical acceptable carrier. The formulation of the primary amine compound for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

The formulations for topical administration may contain the compound used in the present application at a concentration in the range of 0.001-10%, 0.05-10%, 0.1-10%, 0.2-10%, 0.5-10%, 1-10%, 2-10%, 3-10%, 4-10%, 5-10%, or 7-10% (weight/volume), or in the range of 0.001-2.0%, 0.001-1.5%, or 0.001-1.0%, (weight/volume), or in the range of 0.05-2.0%, 0.05-1.5%, or 0.05-1.0%, (weight/volume), or in the range of 0.1-5.0%, 0.1-2.0%, 0.1-1.5%, or 0.1-1.0% (weight/volume), or in the range of 0.5-5.0%, 0.5-2.0%, 0.5-1.5%, or 0.5-1.0% (weight/volume), or in the range of 1-5.0%, 1-2.0%, or 1-1.5% (weight/volume). The formulations for topical administration may also contain the compound used in the present application at a concentration in the range of 0.001-2.5%, 0.01-2.5%, 0.05-2.0%, 0.1-2.0%, 0.2-2.0%, 0.5-2.0%, or 1-2.0% (weight/weight), or in the range of 0.001-2.0%, 0.001-1.5%, 0.001-1.0%, or 0.001-5% (weight/weight).

In some embodiments, the compound or pharmaceutically acceptable salt thereof is administered systemically. In some embodiments, the compound or pharmaceutically acceptable salt thereof is administered orally as part of a solid pharmaceutical composition. In some embodiments, the pharmaceutical composition is a liquid. In some embodiments, the pharmaceutical composition is administered as a liquid via nasogastric tube.

In some embodiments, the dose of the compound or pharmaceutically acceptable salt thereof is about 10 mg to about 10,000 mg per day. In some embodiments, the dose of the compound or pharmaceutically acceptable salt thereof is about 10 mg to about 7500 mg per day. In some embodiments, the dose of the compound or pharmaceutically acceptable salt thereof is about 50 mg to about 3600 mg per day. In some embodiments, the dose of the compound or pharmaceutically acceptable salt thereof is about 250 mg to about 2400 mg per day. In some embodiments, the dose of the compound or pharmaceutically acceptable salt thereof is about 600 mg to about 5000 mg per day. In some embodiments, the dose of the compound or pharmaceutically acceptable salt thereof is about 1000 mg to about 7500 mg per day.

In some embodiments, the compound or pharmaceutically acceptable salt thereof is administered once, twice, thrice, or four times per day. In some embodiments, the compound or pharmaceutically acceptable salt thereof is administered twice per day.

In some embodiments, the dose of the compound or pharmaceutically acceptable salt thereof is about 600 mg BID (i.e., twice per day); 1.2 g BID; or 2.4 g BID.

In some embodiments, the pharmaceutical composition is administered daily in one or more divided doses. In some embodiments, the composition is administered once per day (qua diem; QD). In some embodiments, the composition is administered twice per day (bis in die; BID). In some embodiments, the composition is administered thrice per day (ter in die; TID). In some embodiments, the composition is administered four times per day (quater in die; QID). In some embodiments, the composition is administered every four (4) hours (quaque four hours; q4h).

In some embodiments, compound I-1 is selected as the active pharmaceutical ingredient and is processed and manufactured to a solid form thereof, such as its most stable polymorph, prior to compounding into drug product. In some embodiments, the solid form, e.g., polymorph, is one of those described in PCT/US2020/031138, published as WO 2020/223685, hereby incorporated by reference.

In some embodiments, the solid form of compound I-1 is substantially amorphous or crystalline, or is a mixture thereof. In some embodiments, the solid form is substantially free of impurities.

In certain embodiments, compound I-1 is a crystalline solid. In some embodiments, compound I-1 is a crystalline solid substantially free of amorphous compound I-1. As used herein, the term "substantially free of amorphous compound I-1" means that the compound contains no significant amount of amorphous compound I-1. In some embodiments, at least about 95% by weight of crystalline compound I-1 is present. In still other embodiments of the invention, at least about 99% by weight of crystalline compound I-1 is present.

It has been found that compound I-1 can exist in a variety of solid forms. Exemplary such forms include polymorphs such as those described below.

In some embodiments, compound I-1 is amorphous. In some embodiments, compound I-1 is amorphous, and is substantially free of crystalline compound I-1.

In some embodiments, compound I-1 is a solid form in PCT/US2020/031138 selected from Compound 5:

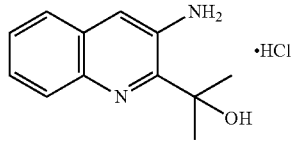

wherein the form is of Form A or Form B. In some embodiments, the compound is crystalline. In some embodiments, the compound is a crystalline solid substantially free of amorphous compound 5. In some embodiments, the compound is substantially free of impurities. In some embodiments, the compound has one or more peaks in its XRPD selected from those at about 13.9, about 15.8 and about 24.3 degrees 2-theta. In some embodiments, the compound has at least two peaks in its XRPD selected from those at about 13.9, about 15.8 and about 24.3 degrees 2-theta. In some embodiments, the compound is of Form A. In some embodiments, the compound has an XRPD substantially similar to that depicted in FIG. 21 of PCT/US2020/031138. In some embodiments, the compound has one or more peaks in its XRPD selected from those at about 10.2, about 17.0 and about 28.8 degrees 2-theta. In some embodiments, the compound has at least two peaks in its XRPD selected from those at about 10.2, about 17.0 and about 28.8 degrees 2-theta. In some embodiments, the compound is of Form B. In some embodiments, the compound has an XRPD substantially similar to that depicted in FIG. 23 of PCT/US2020/031138.

In some embodiments, compound I-1 is a solid form described in PCT/US2020/031138 selected from the group consisting of:

Compound A

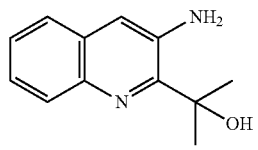

of Form A;

Compound 1

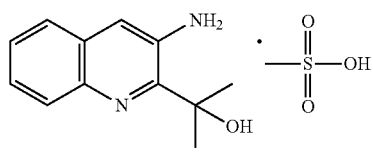

of Form A or Form B;

Compound 2

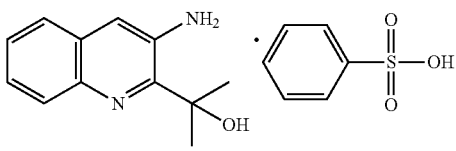

of Form A;

Compound 3

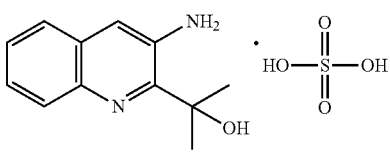

of Form A, Form B, Form C or Form D;

Compound 4

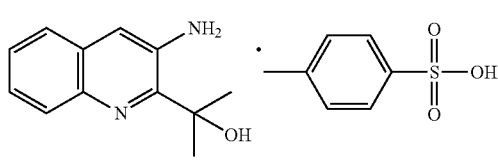

of Form A or Form B;

Compound 6

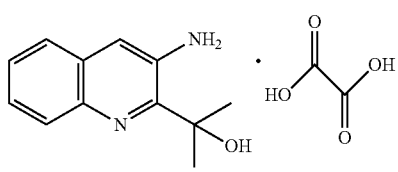

of Form A or Form B;

Compound 7

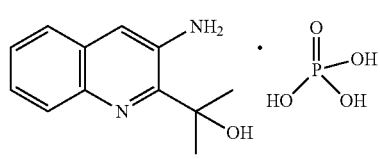

of Form A or Form B;

Compound 8

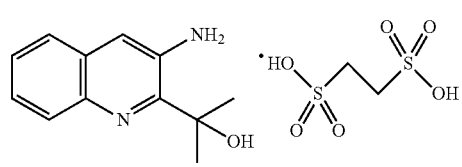

of Form A;

Compound 9

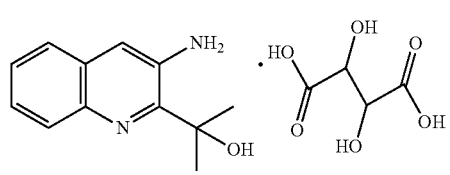

of Form A, Form B or Form C;

Compound 10

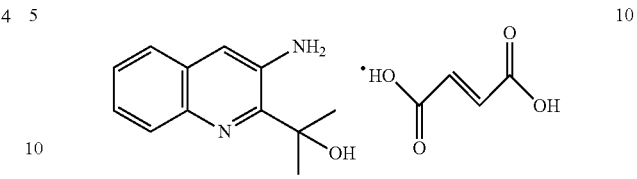

of Form A; and

Compound 11

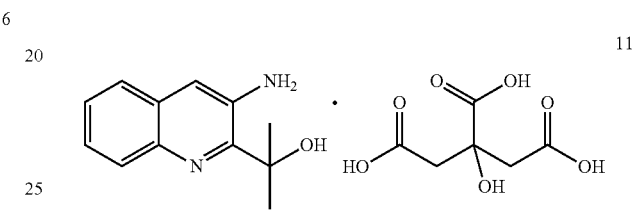

of Form A.

In some embodiments, the present invention provides a pharmaceutical composition or unit dosage form comprising a solid form of compound I-1 in the form of Compound A, wherein Compound A has one or more peaks in its XRPD selected from those at about 10.4, about 17.5, and about 20.9 degrees 2-theta. In some such embodiments, the present invention provides Compound A, wherein the compound has at least two peaks in its XRPD selected from those at about 10.4, about 17.5, and about 20.9 degrees 2-theta. In some such embodiments, the present invention provides Compound A, wherein the compound is of Form A. In some embodiments, the present invention provides Compound A, wherein the compound has an XRPD substantially similar to that depicted in FIG. 1 of PCT/US2020/031138.

In some embodiments, the quinoline compound is a deuterium-enriched compound described in U.S. Pat. No. 10,550,085, the entirety of which is hereby incorporated by reference.

All publications, patents, patent applications and other documents cited in this application are hereby incorporated by reference in their entireties for all purposes to the same extent as if each individual publication, patent, patent application or other document were individually indicated to be incorporated by reference for all purposes.

All features of each of the aspects of the invention apply to all other aspects mutatis mutandis.

EXEMPLIFICATION

Example 1: Solid Oral Dosage Formulation

Compound I-1 was selected as the active pharmaceutical ingredient. In this case, the most stable polymorph of I-1 was used for the formulation. All excipients used in the I-1 drug product comply with their respective compendial monographs. None of the excipients used are of human or animal origin.

Formulation Development

Compound I-1 was formulated into 10 mg and 100 mg unit dose capsules. The proposed clinical formulation has been developed to allow for the potential of future introduction of additional strengths.

Spray-drying was selected for formulation of this compound. By co-precipitating the compound with a polymer in a stable amorphous solid dispersion, spray-drying improved the dissolution rates and enhanced the bioavailability. The I-1 drug substance is a hydrophobic substance with poor solubility in aqueous media but increased solubility in non-polar solvents. This made I-1 an appropriate candidate for the application of formulation through spray drying dispersion (SDD).

Excipient Compatibility Study and Selection:

Eudragit L100 was selected as the polymer that was compatible with I-1 and demonstrated acceptable stability and dispersion characteristics when spray dried with I-1. I-1 and Eudragit L100 were dissolved in methanol and spray dried to generate the spray dried intermediate (SDI) which was then applied in the excipient selection study.

Multiple excipients were tested with the I-1 SDI for compatibility as well as compatibility with gelatin and hydroxypropyl methylcellulose (HPMC) capsules. Excipients were selected based on the known physical properties and manufacturability on blending (Table A).

TABLE A

Formulation of Compound I-1

| No. | Component | Function |
|---|---|---|
| 1 | I-1 SDI | Intermediate |
| 2 | I-1 Crystalline: Eudragit L100 | SDI composition |
| 3 | Microcrystalline cellulose (Avicel PH102) | Filler |
| 4 | Mannitol (Pearlitol 200 SD) | Filler |
| 5 | Lactose Monohydrate | Filler |
| 6 | Croscarmellose sodium (Ac-Di-Sol) | Disintegrant |
| 7 | Crospovidone (Kollidon CL) | Disintegrant |
| 8 | Kollidon VA64 | Binder |
| 9 | Magnesium Stearate | Lubricant |
| 10 | Fumed Silica (Aerosil) | Glidant |
| 11 | Sodium Lauryl Sulphate | Surfactant |
| 12 | Citric Acid | Acidity regulator for effervescent component |
| 13 | Effer-soda (surface modified sodium bicarbonate/carbonate) | Effervescent component |
| 14 | Gelatin capsule | Encapsulation |
| 15 | Hydroxypropyl methylcellulose (HPMC) capsule | Encapsulation |

The SDI and excipient mixtures were prepared and evaluated for chemical and physical stability. Samples of each blend were stored at 25° C./60% RH (open for only 2 weeks), 40° C./75% RH (open), and 60° C. (closed), and tested out to 28 days. Samples were analyzed for physical stability (visually), structural stability by x-ray powder diffraction (XRPD), and purity by high-performance liquid chromatography (HPLC).

Capsules comprising 100 mg of compound I-1 were manufactured as a non-sterile spray dried, granulated powder blend. The blend was then filled into capsules for oral delivery. The capsules were packaged in high-density polyethylene bottles. The quantitative composition of the 100 mg capsule is presented in Table B.

TABLE B

Quantitative Composition of 100 mg Capsule

| Component | Quality/Grade | Quantity (mg/unit) | % (w/w) of Total |
|---|---|---|---|
| Compound I-1 | GMP | 100 | 31.5% |
| Eudragit L100 | USP, EP | 185.7 | 58.5% |
| Pearlitol 200 SD (Mannitol) | USP, EP | 6.4 | 2.0% |
| Kollidon ® VA 64 Fine | USP, EP | 22.2 | 7.0% |
| Aerosil 200 Pharma (Fumed Silica) | NF, EP, JP | 1.6 | 0.50% |
| Magnesium Stearate | NF, BP, EP, JP | 1.6 | 0.50% |
| Total | — | 317.5 | — |

USP = United States Pharmacopeia;
EP = European Pharmacopeia;
JP = Japanese Pharmacopeia;
NF = National Formulary.

Example 2: Pharmacokinetics of Compound I-1 in the Dog by the Intravenous, Oral (Capsule) and Oral (Gavage) Routes of Administration List of Abbreviations

| GLP | Good Laboratory Practice |
|---|---|
| t1/2 | Half-life |
| C0 | Concentration at time zero |
| CL | Clearance |
| AUC 0-t | Area under the curve from time 0 to end |
| AUC o-inf | Area under the curve from time zero to infinity |
| Vss | Volume of distribution at steady state |
| AUC/Dose | Area under the cure normalized by dose |
| Tmax | Time of maximum concentration |
| Cmax | Maximum concentration |
| BioA | Bioavailability |
| SBECD | sulfobutylether-β-cyclodextrin |
| PO | Per Os (oral administration) |
| mpk | Milligrams per kilogram |
| mg/kg | Milligrams per kilogram |
| h | Hours |
| Subj. | Subject |

A pharmacokinetic study was conducted to compare the bioavailability of capsule and suspension oral formulations vs. an intravenous formulations.

Bioanalytical Summary

The standard curve was prepared from 1 to 2,000 ng/mL. QC samples were prepared at 30, 30, and 750 ng/mL. Dilution QCs were prepared at 10-fold dilution. Deuterated ($d_6$) I-1 (compound 1-7) was used as an internal standard. A 50 μL aliquot of sample was added to 150 μL of cold internal standard in acetonitrile to effect protein precipitation. The resulting supernatants were analyzed by LCMS. Diluted sample data was utilized only for over-the-curve results.

Pharmacokinetic Summary

The intravenous data were analyzed to determine a half-life (t½) of 1.82 hours. The Clearance (CL) was moderate at 12.2 ml/kg/min. The steady-state volume of distribution was estimated to be 1,385 mL/kg. The bioavailability results for the capsules and oral gavage routes were similar at 83% and 75% respectively. Within the error of the experiment, there was no difference between the capsule and gavage routes with regard to bioavailability. The Tmax of the Capsule route was 2.37 hours and the Tmax of the oral gavage route was 0.518 hours.

Experimental Design

Briefly, 9 male non-naïve beagle dogs were assigned in groups of 3 to 3 dose groups. Group 1 was dosed 3 mg/kg by the intravenous route in a vehicle of 20% sulfobutylether-β-cyclodextrin (SBECD). Group 2 was dosed 10 mg/kg by the oral gavage route in a vehicle of 0.5% methylcellulose (MC). Group 3 was dosed with 100 mg capsules.

The I-1 100 mg capsules are manufactured as a non-sterile spray dried, granulated powder blend. The blend is then filled into capsules for oral delivery. The capsules are packaged in high-density polyethylene bottles. The quantitative composition of the I-1 100 mg capsule is presented above in Table B.

Dosing

Formulations will be administered to the animals at time 0 on the appropriate day.

Procedure: (PO) gavage: formulations will be administered via a rubber oral gavage tube followed by a 10 mL flush with drinking water. (PO) tablet: tablets will be administered orally by placing the tablet in the back of the throat followed by a 10 mL flush with water.

Sampling

Frequency: Pre-dose, 5, 15, 30 min, 1, 2, 4, 8, and 12 hrs post-dose (IV); pre-dose, 15, 30 min, 1, 2, 4, 8, and 12 hrs post-dose (PO by gavage and PO by capsule).

Blood collection: each blood sample will be collected from the dog's jugular vein or other accessible vein via direct venepuncture, placed into a pre-labeled tube containing $K_2$EDTA and kept on ice until centrifugation.

Plasma preparation and storage: Certifuged at 4 C at 3,000× for 5 mm. Stored in a freezer until analysed.

Pharmacokinetics

Pharmacokinetics package PKSolver2.0™ has been validated against WinNonLin™ as a tool for non-GLP studies and was used to process the pharmacokinetic data.

For each route, the average data were processed with non-compartmental, one compartment, and two compartment models. The models were assessed for goodness of fit and the accuracy of the model to assess the biphasic data, with either a) no weighting, b) 1/concentration observed, or c) 1/concentration observed squared. 1/concentration predicted, and 1/concentration predicted squared weightings were also assessed for best fit. For the capsule data, one animal was observed at 71.5 ng/mL at the 0.25 hour timepoint and the other two subjects were zero. The zeros were averaged with the 71.5 value for a resulting average of 23.8. For the In Group 2 (PO Gavage) subject 3 experienced 30 mL of emesis, so the dose assigned to that subject was 7.46. In all cases, the subjects were modelled individually, and the individual PK parameters were averaged to provide final parameters.

For group 1 (intravenous) the final model selected was a two compartment model with 1/concentration observed squared weighting. Subjects 1, 2, and 3 had an R2 value of 0.9942, 0.9941, and 0.9905 respectively and an AIC of −5.68, −8.67, and −3.18 respectively.

For group 2 (oral gavage) the final model was a two compartment extravascular model with 1/concentration predicted squared weighting. Subjects 1, 2, and 3 had an R2 value of 0.9641, 0.9807, and 0.9397 respectively and an AIC of −3.75, −7.63, and 2.29 respectively.

For group 3 (oral capsule) the final model was a one compartment extravascular model with a lag time and no weighting. Subjects 1, 2, and 3 had an R2 value of 0.8561, 0.8738, and 0.7615 respectively and an AIC of 87.9, 96.5, and 99.4 respectively. The body weight of each animal was used to assign a mg/kg dose to each individual. Subject 1 was dosed at 7.69 mg/kg. Subject 2 was 6.94 mg/kg, and Subject 3 was 6.99 mg/kg.

Results

Figure 1:
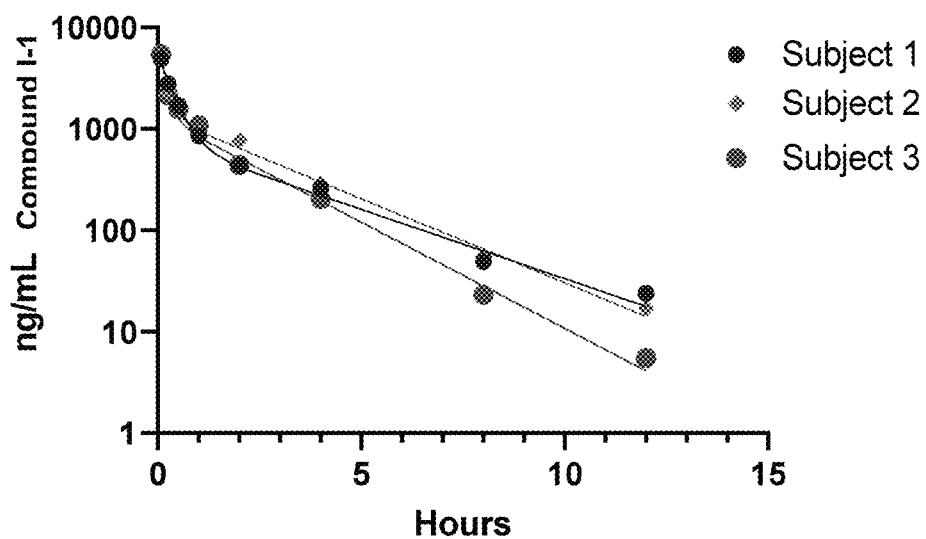
FIG. 1 shows the blood time-concentration profile in beagle dogs administered compound I-1 (Group 1; intravenous administration) with data points (markers) and model prediction (solid lines).
Figure 2:
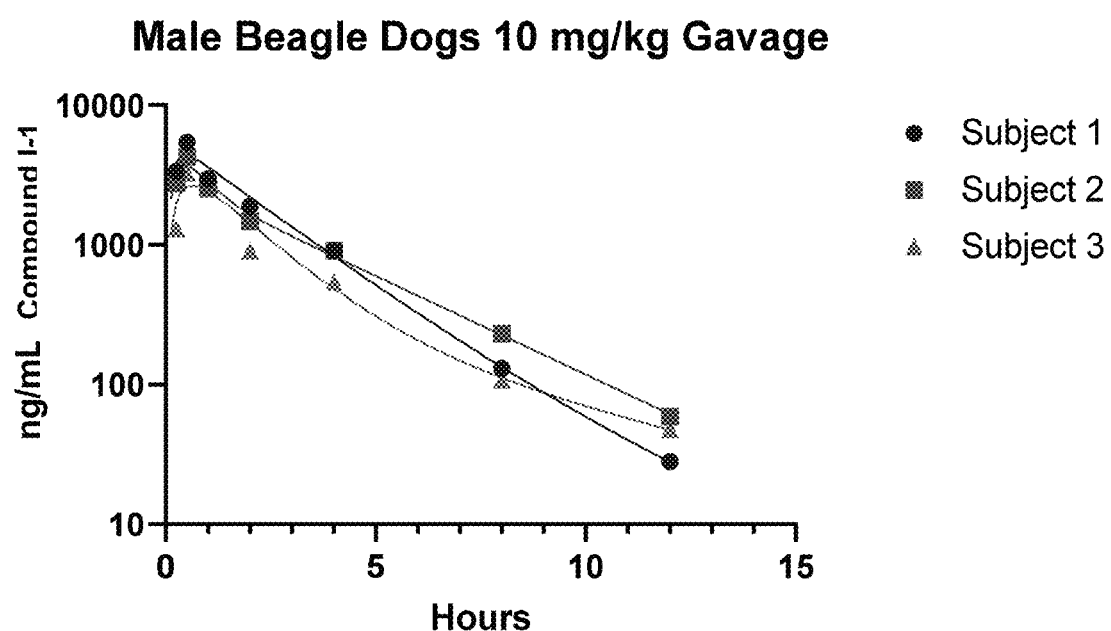
FIG. 2 shows the blood time-concentration profile in beagle dogs administered compound I-1 (Group 2; oral gavage) with data points (markers) and model prediction (solid lines).
Figure 3:
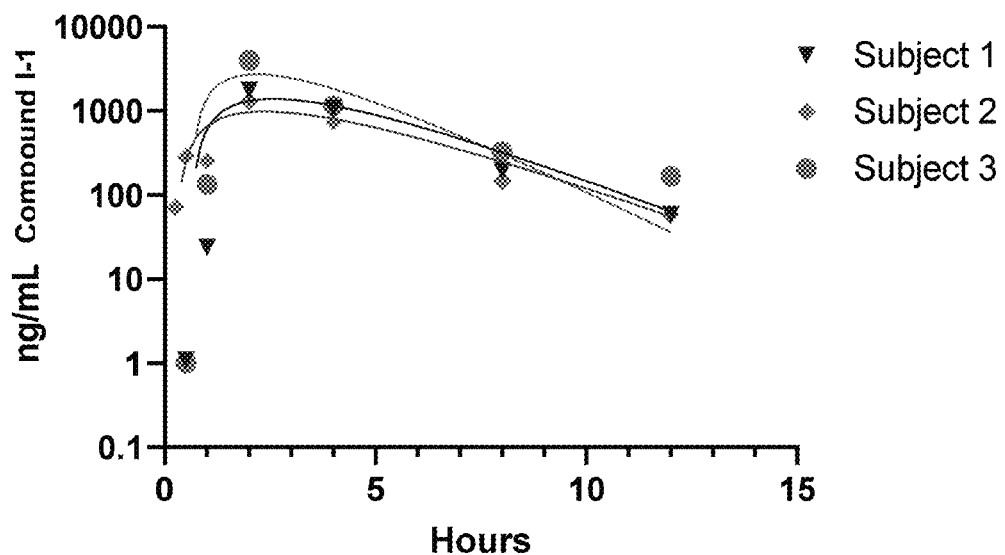
FIG. 3 shows the blood time-concentration profile in beagle dogs administered compound I-1 (Group 3; capsule) with data points (markers) and model prediction (solid lines).

The individual time-concentration profiles are detailed in Table C. The time-concentration profiles plots are depicted in FIGS. 1, 2, and 3. The PK parameters are detailed in Table C.

TABLE C

Time-Concentration Profiles for Groups 1, 2, and 3

| Time (h) | Subject 1 | Subject 2 | Subject 3 | Average |
|---|---|---|---|---|
| Group 1: IV 3 mg/kg | | | | |
| 0.083 | 4908 | 4896 | 5427 | 5077 |
| 0.25 | 2780 | 2300 | 2146 | 2409 |
| 0.5 | 1722 | 1699 | 1566 | 1662 |
| 1 | 857 | 908 | 1088 | 951 |
| 2 | 436 | 766 | 443 | 548 |
| 4 | 259 | 287 | 203 | 250 |
| 8 | 49.0 | 55.4 | 23.1 | 42.5 |
| 12 | 23.9 | 17.0 | 5.50 | 15.5 |
| Group 2: PO Gavage 10 mg/kg | | | | |
| 0.25 | 3363 | 2757 | 1309 | 2476 |
| 0.5 | 5402 | 4286 | 3264 | 4317 |
| 1 | 2972 | 2608 | 2515 | 2698 |
| 2 | 1888 | 1473 | 908 | 1423 |
| 4 | 909 | 909 | 541 | 787 |
| 8 | 131 | 233 | 108 | 157 |
| 12 | 28.1 | 59.1 | 48.1 | 45.1 |
| Group 3: PO Capsule 7 mg/kg | | | | |
| 0.25 | 0 | 71.5 | 0 | 23.8 |
| 0.5 | 1.10 | 290 | 1.00 | 97.4 |
| 1 | 24 | 254 | 134 | 137 |
| 2 | 1745 | 1318 | 3987 | 2350 |
| 4 | 1067 | 736 | 1151 | 985 |
| 8 | 195 | 147 | 327 | 223 |
| 12 | 58.7 | 58.0 | 167 | 94.5 |

TABLE D

Pharmacokinetic Parameters

| Parameter | Unit | Subj1 | Subj2 | Subj3 | Average | % RSD |
|---|---|---|---|---|---|---|
| Intravenous - 3 mg/kg | | | | | | |
| t1/2 | h | 2.20 | 1.82 | 1.44 | 1.82 | 21% |
| C0 | ng/ml | 5597 | 6672 | 7893 | 6721 | 17% |
| CL | mL/kg/min | 12.2 | 11.0 | 13.3 | 12.2 | 9% |
| AUC 0-t | ng/ml * h | 4028 | 4523 | 3759 | 4103 | 9% |
| AUC 0-inf | ng/ml * h | 4084 | 4560 | 3768 | 4137 | 10% |
| Vss | mL/kg | 1508 | 1395 | 1252 | 1385 | 9% |
| AUC/Dose | ng/ml * h/mL/kg | 1361 | 1520 | 1256 | 1379 | 10% |
| Oral Gavage 0.5% Methylcellulose 10 mg/kg | | | | | | |
| t1/2 | h | 2.85 | 2.13 | 4.08 | 3.02 | 33% |
| Tmax | h | 0.459 | 0.460 | 0.635 | 0.518 | 20% |
| Cmax | ng/ml | 4351 | 3671 | 2651 | 3558 | 24% |

TABLE D-continued

Pharmacokinetic Parameters

| AUC 0-t | ng/ml * h | 11119 | 9913 | 7052 | 9361 | 22% |
|---|---|---|---|---|---|---|
| AUC 0-inf | ng/ml * h | 11209 | 10103 | 7326 | 9546 | 21% |
| AUC/Dose | ng/ml * h/mg/kg | 1121 | 1010 | 982 | 1038 | 7% |
| BioA | % | | | | 75% | |

100 mg Capsule, average dose 7.2 mg/kg

| Parameter | Unit | Subj1 | Subj2 | Subj3 | Average | STDev |
|---|---|---|---|---|---|---|
| t1/2 | h | 1.38 | 1.49 | 1.10 | 1.33 | 15% |
| Tmax | h | 2.57 | 2.37 | 2.16 | 2.37 | 9% |
| Cmax | ng/ml | 1391 | 986 | 2729 | 1702 | 54% |
| AUC 0-t | ng/ml * h | 7238 | 5491 | 11511 | 8080 | 38% |
| AUC 0-inf | ng/ml * h | 7348 | 5614 | 11556 | 8173 | 37% |
| AUC/Dose | ng/ml * h/mg/kg | 955 | 809 | 1653 | 1139 | 40% |
| BioA | % | | | | 83% | |

Conclusions

The bioavailability between the capsule and 0.5% methylcellulose suspension formulations is similar within the margin of error of the experiment at 75% and 83% respectively. The Tmax is greater for the capsule at 2.37 hours relative to the suspension at 0.518 hours.

Example 3: Phase 1 Clinical Trial of Compound I-1

This Phase 1 trial was a first-in-human, randomized, double-blind, placebo-controlled trial with a 3:1 randomization of I-1 and placebo. The trial was comprised of single ascending dose (SAD) and multiple ascending dose (MAD) protocols. MAD drug exposure was 10 days of twice-per-day (BID) administration.

Overall, I-1 was found to be safe and tolerable. The adverse event profile of I-1 was favorable compared to placebo: A total of 6 (9.4%) subjects receiving I-1 had treatment emergent adverse events (TEAEs), compared to 4 (19.1%) subjects who received placebo. There were no interruptions or discontinuations of study drug administration.

No clinically meaningful changes were observed in hepatic or renal analytes, including transaminases (ALT and AST), AlkPhos (ALP), amylase, GGT, bilirubin, creatinine kinase and creatinine. No changes in serum glucose were observed. No clinically meaningful changes were observed in heart rate (HR), blood pressure (systolic, diastolic and orthostatic changes), respiratory rate, pulse oximetry, or temperature. No clinically significant hematological changes were observed. I-1 did not lead to QTcF prolongation. There were no subjects who had QTcF ≥500 msec or a change of ≥60 msec from baseline. Five subjects had a change of >30 msec from baseline, but did not require intervention or study drug interruption or discontinuation, and all subjects remained asymptomatic. Three of these five subjects were in the SAD portion of the study (one each in the 100 mg, 200 mg and 700 mg dose cohorts) and the remaining two subjects were in the MAD portion of the study (one each in the 150 mg BID and 300 mg BID dose cohorts).

A linear correlation was observed in $C_{max}$ and AUC as dose increased. The half-life ($t_{1/2}$) was consistent across cohorts and days, and mean values in multiple day exposures ranged between 3.49 to 6.83 hours. Little to no accumulation of the drug was seen across all cohorts.

Figure 4:
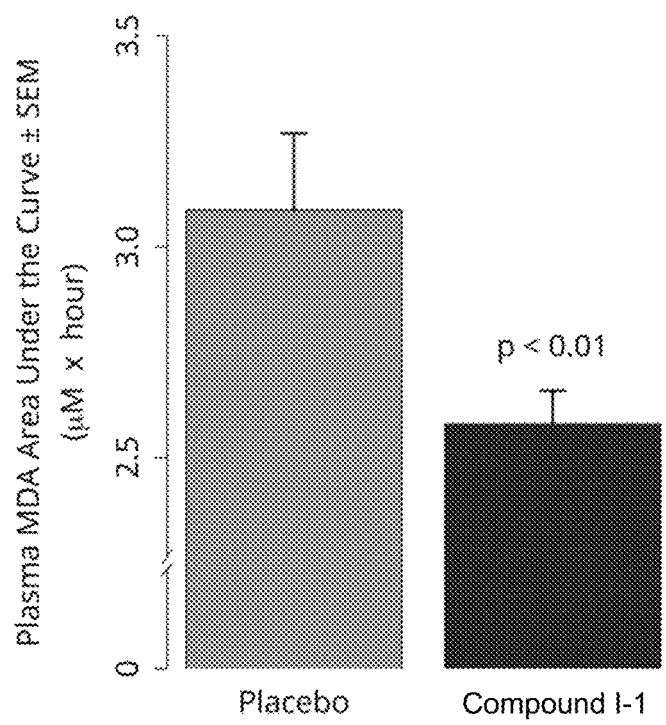
FIG. 4 shows plasma total area under the curve (AUC) of malondialdehyde (MDA) in plasma of human subjects administered I-1 orally in a Phase 1 trial.

FIG. 4 shows plasma total area under the curve (AUC) of malondialdehyde (MDA) in plasma of human subjects administered I-1 orally in this Phase 1 trial. FIG. 5 shows area under the curve (AUC) of malondialdehyde (MDA) on day 1 and day 8 in plasma of human subjects administered I-1 orally. At the top dose (600 mg BID), a Cmax of 1700 ng/mL (approximately 8.5 mM) and an $AUC_{0-12}$ of 7220 h*ng/mL were consistent with an adequate molar ratio to achieve stoichiometric efficacy against elevated reactive aldehyde species (RASP; also referred to as toxic aldehydes). A decrease in free MDA levels was observed in the plasma of healthy volunteers.

Single Ascending Dose (SAD)

A total of 54 healthy volunteers were randomized across two cohorts of varying doses: 41 subjects received I-1 and 13 subjects received placebo. Two (4.9%) subjects, both on I-1, withdrew early from the study (for reasons unrelated to study drug).

| | Placebo pooled N (%) | 20 mg N (%) | 50 mg N (%) | 100 mg N (%) | 200 mg N (%) | 400 mg N (%) | 700 mg N (%) | 1200 mg N (%) |
|---|---|---|---|---|---|---|---|---|
| Randomized | 13 (100) | 6 (100) | 6 (100) | 6 (100) | 6 (100) | 5 (100) | 6 (100) | 6 (100) |
| Safety population | 13 (100) | 6 (100) | 6 (100) | 6 (100) | 6 (100) | 5 (100) | 6 (100) | 6 (100) |
| Completed study | 13 (100) | 6 (100) | 5 (83.3) | 5 (83.3) | 6 (100) | 5 (100) | 6 (100) | 6 (100) |
| Early withdrawal | 0 | 0 | 1 (16.7) | 1 (16.7) | 0 | 0 | 0 | 0 |

Subjects were predominantly males (M:F—34:20), Black or African Americans (67%), and non-hispanics (93%). A fair balance in age and BMI was observed across the cohorts. Mean age and BMI range was 30.0-38.5 years and 24.3-26.5, respectively.

Two (3.7%) subjects who received I-1 experienced TEAs. A subject in the 100 mg dose cohort had an event of syncope lasting less than a minute, moderate in intensity and deemed to be related to the study drug. The subject also had postural orthostatic tachycardia syndrome and back pain. The other subject had an AE of sinus congestion, mild in intensity and deemed not to be related to I-1. This subject had received a single dose of 700 mg.

Pharmacokinetic data are presented below.

| | 20 mg | 50 mg | 100 mg | 200 mg | 400 mg | 700 mg | 1200 mg |
|---|---|---|---|---|---|---|---|
| $C_{max}$ (ng/mL) | 26.4 | 56.7 | 140 | 459 | 869 | 2020 | 4220 |

|         | 20 mg | 50 mg | 100 mg | 200 mg | 400 mg | 700 mg | 1200 mg |
|---------|-------|-------|--------|--------|--------|--------|---------|
| AUC$_{inf}$ (ng * h/mL) | 50.0 | 156 | 433 | 1140 | 2730 | 6710 | 14500 |
| t$_{1/2}$ (h) | NC | NC | 3.52 | 6.04 | 6.15 | 7.33 | 7.69 |

Multiple Ascending Dose (MAD)

Thirty-one (31) subjects were randomized to varying doses: 23 subjects received I-1 and 8 subjects received placebo. No subject required study drug interruption, and all subjects completed drug administration per protocol.

|  | Placebo pooled N (%) | 50 mg BID N (%) | 150 mg BID N (%) | 350 mg BID N (%) | 600 mg BID N (%) |
|---|---|---|---|---|---|
| Randomized | 8 (100) | 6 (100) | 6 (100) | 5 (100) | 6 (100) |
| Safety population | 8 (100) | 6 (100) | 6 (100) | 5 (100) | 6 (100) |
| Completed study | 8 (100) | 6 (100) | 6 (100) | 5 (100) | 6 (100) |
| Early withdrawal | 0 (100) | 0 (100) | 0 (100) | 0 (100) | 0 (100) |

Subjects were almost equally distributed between genders (F=15 and M=16), Black or African Americans constituted 58% of the study population, and 87% were non-hispanics. Mean age and BMI ranges were 33.2-40.3 years and 23.9-28.1, respectively. Treatment compliance to the study drug (BID for 10 days) was 100%.

A total of 8 subjects had TEAEs; 4 (50%) subjects received placebo and 4 (17.4%) subjects received I-1. TEAEs seen are presented in the table below. All TEAEs were mild and deemed not to be related to the study drug.

|  | Placebo Pooled N (%) | I-1 50 mg BID N (%) | I-1 150 mg BID N (%) | I-1 350 mg BID N (%) | I-1 600 mg BID N (%) | I-1 Total N (%) |
|---|---|---|---|---|---|---|
| Influenza like illness | 1 (12.5%) | 0 | 0 | 0 | 0 | 0 |
| Ligament sprain | 1 (12.5%) | 0 | 0 | 0 | 0 | 0 |
| Muscle spasms | 1 (12.5%) | 0 | 0 | 0 | 0 | 0 |
| Headache | 1 (12.5%) | 0 | 0 | 0 | 0 | 0 |
| Pruritis | 1 (12.5%) | 1 (16.7%) | 0 | 0 | 0 | 1 (4.3%) |
| Nasal congestion | 0 | 1 (16.7%) | 0 | 0 | 0 | 1 (4.3%) |
| URTI | 0 | 0 | 0 | 1 (20.0%) | 0 | 1 (4.3%) |
| Rhinitis | 0 | 0 | 0 | 0 | 1 (16.7%) | 1 (4.3%) |

PK data are presented below.

| Day | Dose | Mean C$_{max}$ (ng/mL) | Mean AUC$_{0-12}$ (h * ng/mL) | Mean t$_{1/2}$ (h) |
|---|---|---|---|---|
| 1 | 50 mg BID | 70.2 | 148 | 3.49 |
|   | 150 mg BID | 343 | 809 | 4.86 |
|   | 350 mg BID | 1190 | 2950 | 5.67 |
|   | 600 mg BID | 2230 | 6450 | 4.15 |
| 10 | 50 mg BID | 85.9 | 252 | 5.25 |
|    | 150 mg BID | 320 | 1170 | 6.34 |
|    | 350 mg BID | 1230 | 4340 | 6.83 |
|    | 600 mg BID | 1700 | 7220 | 4.66 |

Example 4: Pharmacokinetic Comparison of ADX-102 (Reproxalap) and Compound I-1 in a Rat Model List of Abbreviations

| A | Membrane area |
|---|---|
| $_A$ (subscript) | Acceptor concentration |
| A→B | Apical to basolateral |
| ADME | Absorption, distribution, metabolism, and excretion |
| AMP | Adenosine monophosphate |
| ATP | Adenosine triphosphate |
| AUC | Area under the concentration-time curve |
| AUC$_{0-t}$ | Area under the concentration-time curve from 0 to the final time point with measurable concentration of compound I-1 or other test compound |
| AUC$_{0-24}$ | Area under the concentration-time curve through 24 hours after dosing |
| AUC$_\infty$ | Area under the concentration-time curve extrapolated to infinity |
| B→A | Basolateral to apical |
| BLQ | Below the limit of quantitation |
| BSEP | Bile salt export pump |
| C$_0$ | Initial concentration |
| CAR | Constitutive androstane receptor |
| Cb | Concentration blood |
| CL | Plasma clearance |
| CL$_{int}$ | Intrinsic clearance |
| CL$_p$ | Plasma clearance |
| cm | centimeter |
| C$_{max}$ | Maximum observed concentration |
| Cp | Concentration plasma |
| CV | Coefficient of variation |
| CYP | Cytochrome P450 |
| DMEM | Dulbecco's Modified Eagle Medium |
| DMSO | Dimethylsulfoxide |
| DQC | Diluted quality control |
| DQCL | Low diluted quality control |
| DQCH | High diluted quality control |
| $_E$ (subscript) | Equilibrium concentration |
| EC$_{50}$ | Concentration of at which 50% of the maximum effect is achieved |
| EDTA | Ethylenediaminetetraacetic acid, |
| Emax | Maximum effect |
| F | Bioavailability |
| fu | Unbound fraction |
| GLP | Good Laboratory Practice |
| H | Hematocrit |
| HEPES | 4-(2-hydroxyethyl)-1-piperazineethanesulfonic acid) is a zwitterionic sulfonic acid buffering agent |
| hERG | Human Ether-à-go-go |
| HLM | Human liver microsomes |
| HPLC | High-performance liquid chromatography |
| HLC-AO | Human Liver Cytosol-Aldehyde Oxidase |
| IC$_{50}$ | Half-maximal inhibitory concentration |
| IS | Internal standard |
| IV | Intravenous |
| k | slope |
| kg | Kilogram |

-continued

| | |
|---|---|
| $K_{RBC/PL}$ | Partition coefficient, red blood cell to plasma |
| $K_2$EDTA | Dipotassium ethylenediamine triacetic acid |
| $K_3$EDTA | Tripotassium ethylenediamine triacetic acid |
| LC-MS/MS | Liquid chromatography-tandem mass spectrometry |
| LLOQ | Lower limit of quantitation |
| MDCK-MDR1 | Madine-Darby canine kidney cells over-expressing the human multidrug resistance protein one gene for P-glycoprotein |
| mL | Milliliter |
| mg | Milligram |
| μM | Micromolar |
| N | Number |
| NA | Not applicable |
| NADPH | Nicotinamide adenine dinucleotide phosphate |
| NC | Not calculated |
| ND | No data; Not determined |
| ng | nanogram |
| PAMPA | Parallel artificial membrane permeability assay |
| $P_{app}$ | Apparent permeability coefficient |
| PBS | Phosphate buffered saline |
| PCR | Polymerase chain reaction |
| $P_e$ | Effective permeability coefficient |
| P-gp | P-glycoprotein |
| PK | Pharmacokinetics |
| PO | Per os; oral |
| PXR | Pregnane X receptor |
| QC | Quality Control |
| $r^2$ | Coefficient of correlation |
| R3 | Risk score for induction-mediated drug-drug-interactions |
| $R_E$ | Efflux ratio |
| RE | Relative error |
| RSD | Relative standard deviation |
| RT | Room temperature |
| S9 | Post-mitochondrial supernatant fraction |
| t | time |
| $t_{1/2}$ | Half-life |
| TCA | Taurocholic acid |
| TK | Toxicokinetics |
| $T_{max}$ | Time of maximum observed concentration |
| UGT | Uridine 5'-diphospho-glucuronosyltransferase |
| UV | Ultraviolet |
| $V_D$ | Volume donor compartment |
| $V_A$ | Volume acceptor compartment |
| Vz | Volume of distribution as calculated in non-compartmental analysis |

Compound I-1 is the des-chloro analog of ADX-102. Despite their similar structures, it was surprisingly found that compound I-1 is generally better tolerated than ADX-102 as a systemic dose, including showing approximately double the AUC (Area Under the Concentration-Time Curve) when administered to rats. We have therefore investigated compound I-1 in 90-day toxicology studies in rat and dog as well as 10-day studies in man. We compared two data sets to contrast the pharmacokinetics of the two test articles. A 50 mg/kg oral dose PK study of compound I-1 was conducted in Sprague-Dawley rats using methylcellulose suspension. A pharmacokinetic study of ADX-102 was also conducted in Sprague Dawley rats at a dose of 10 mg/kg in a methylcellulose suspension that also contained Tween 80. Both studies also incorporated intravenous administration in captisol for the calculation of clearance and steady state volume of distribution.

TABLE E

Comparison of PK Parameters from I-1 and ADX-102 Pharmacokinetic Studies in Sprague-Dawley Rats

| Study Compound | Species | Form | Dose (mg/kg) | t1/2 | Vss* |
|---|---|---|---|---|---|
| Compound I-1 | SD Rat | 0.5% MC | 50 | 2.96 | 3130 |
| ADX-102 | SD Rat | CMC/Tween | 10 | 2.27 | 1360 |

| Study Compound | CL* | Tmax | Cmax | AUC 0-t | AUC 0-t/ Dose | AUC 0-inf | AUC 0-inf/ Dose |
|---|---|---|---|---|---|---|---|
| Compound I-1 | 65.8 | 0.320 | 4994 | 7299 | 146 | 7669 | 153 |
| ADX-102 | 23** | 0.5 | 390 | 595 | 60 | 640 | 64 |

*Intravenous data using captisol formulation used for CL and Vss.
**timepoints beyond 8 are truncated due to BLQ.

Methods of Analysis

Both studies were dosed by oral gavage. Bioanalysis was conducted using LC-MS/MS. Further details of the experimental approach can be found in the individual reports.

Pharmacokinetic Profiles

The pharmacokinetic profile contrasting the two compounds is shown in FIG. 6. In FIG. 7, the dose-normalized profiles are shown, with the 10 mg/kg data from the ADX-102 dose multiplied five-fold for comparison purposes.

Conclusions

The key finding relates to the dose-normalized AUC results. After normalizing for dose, compound I-1 exhibited nearly double the AUC of ADX-102 despite the use of an emulsifying agent in the ADX-102 formulation.

Example 5: Dosage Forms of Compound I-1

The drug product for compound I-1 is manufactured as non-sterile spray dried, granulated powder blend, filled in a capsule for oral delivery. The drug product is supplied in 10 mg and 100 mg unit dose capsule strengths; 600 mg Powder-In-Bottle; and 250 mg and 300 mg unit dose tablet strengths.

TABLE F

Quantitative Composition of 10 mg Capsule

| | Quantity | |
|---|---|---|
| Component | % w/w | mg/unit |
| Compound I-1 | 31.5% | 10 |
| Eudragit L100 | 58.5% | 18.57 |
| Pearlitol 200 SD (Mannitol) | 2.0% | 0.64 |
| Kollidon ® VA 64 Fine | 7.0% | 2.22 |
| Aerosil 200 Pharma (Fumed silica) | 0.5% | 0.16 |
| Magnesium Stearate, Vegetable Grade-Non Bovine (Mg Stearate) | 0.5% | 0.16 |
| Total | 100.0 | 31.75 |

TABLE G

Quantitative Composition of 100 mg I-1 Capsule

| Component | % w/w | mg/unit |
|---|---|---|
| Compound I-1 | 31.5% | 100 |
| Eudragit L100 | 58.5% | 185.7 |
| Pearlitol 200 SD (Mannitol) | 2.0% | 6.4 |
| Kollidon ® VA 64 Fine | 7.0% | 22.2 |
| Aerosil 200 Pharma (Fumed Silica) | 0.5% | 1.6 |
| Magnesium Stearate, Vegetable Grade-Non Bovine (Mg Stearate) | 0.5% | 1.6 |
| Total | 100.0 | 317.46 |

TABLE H

Quantitative Composition of 600 mg I-1 Active Drug Product (Powder-in-Bottle)

| Component | % w/w | mg/unit |
|---|---|---|
| Compound I-1 | 31.5% | 600 |
| Eudragit L100 | 58.5% | 1114.2 |
| Pearlitol 200 SD (Mannitol) | 2.0% | 38.4 |
| Kollidon ® VA 64 Fine | 7.0% | 132.2 |
| Aerosil 200 Pharma (Fumed silica) | 0.5% | 9.6 |
| Magnesium Stearate, Vegetable Grade-Non Bovine (Mg Stearate) | 0.5% | 9.6 |
| Total | 100.0 | 1905 |

TABLE I

Quantitative Composition of I-1 Active Drug Product - 300 mg Tablet

| Component | % w/w | mg/unit |
|---|---|---|
| Compound I-1 | 30% | 300 |
| Eudragit L100 | 55% | 557.14 |
| Pearlitol 200 SD (Mannitol) | 2% | 20.3 |
| Kollidon ® VA 64 Fine | 7% | 71.0 |
| Aerosil 200 Pharma (Fumed silica) | 1% | 5.1 |
| Magnesium Stearate, Vegetable Grade-Non Bovine (Mg Stearate) | 1% | 10.1 |
| Ac-Di-Sol ® SD-711 Croscarmellose Sodium | 5% | 50.4 |
| Total | 100.0 | 1014.04 |

TABLE J

Quantitative Composition of I-1 Active Drug Product - 250 mg Tablet

| Component | % w/w | mg/unit |
|---|---|---|
| Compound I-1 | 30% | 250 |
| Eudragit L100 | 55% | 464.3 |
| Pearlitol 200 SD (Mannitol) | 2% | 16.9 |
| Kollidon ® VA 64 Fine | 7% | 59.7 |
| Aerosil 200 Pharma (Fumed silica) | 1% | 4.2 |
| Magnesium Stearate, Vegetable Grade-Non Bovine (Mg Stearate) | 1% | 8.4 |
| Ac-Di-Sol ® SD-711 Croscarmellose Sodium | 5% | 42 |
| Total | 100.0 | 845.0 |

We claim:

1. A pharmaceutical composition comprising:
a) compound I-1:

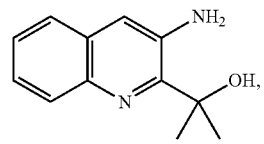

or a pharmaceutically acceptable salt thereof, as about 15% to about 60% by weight of the composition;
b) one or more fillers comprising at least one of microcrystalline cellulose, mannitol, and lactose monohydrate, as about 1% to 20% w/w by weight of the composition;
c) one or more binders comprising vinylpyrrolidone-vinyl acetate copolymer, as about 2% to about 18% w/w by weight of the composition;
d) one or more disintegrants comprising at least one of croscarmellose sodium and crospovidone, as about 1% to 20% w/w by weight of the composition;
e) one or more glidants comprising fumed silica, as about 0.05% to about 2.0% w/w by weight of the composition;
f) one or more lubricants comprising magnesium stearate, as about 0.05% to about 2.0% w/w by weight of the composition;
g) optionally, one or more surfactants comprising lauryl sulfate, as about 0.05% to 2.0% w/w by weight of the composition; and
h) optionally, one or more effervescent components comprising sodium bicarbonate and an organic acid selected from citric acid or tartaric acid, as about 0.05% to 2.0% w/w by weight of the composition,
wherein the pharmaceutical composition is in a unit dosage form for oral administration to a subject in need thereof, in the form of a capsule or tablet;
wherein the subject is a human and upon oral administration to the human subject, the unit dosage form provides an oral bioavailability of at least 70% of the administered dose of I-1, or a pharmaceutically acceptable salt thereof.

2. The pharmaceutical composition of claim 1, wherein compound I-1 or a pharmaceutically acceptable salt thereof is present in the pharmaceutical composition as a spray-dried solid comprising a copolymer of methacrylate and acrylate.

3. The pharmaceutical composition of claim 2, wherein compound I-1 or a pharmaceutically acceptable salt thereof is provided as a spray-dried solid mixed with the copolymer of methacrylate and acrylate; and about 0.9 mg to about 3.6 mg of the copolymer of methacrylate and acrylate is mixed with each 1 mg of I-1 or pharmaceutically acceptable salt thereof.

4. The pharmaceutical composition of claim 1, wherein the capsule or tablet comprises about 5 mg to about 500 mg I-1, or a pharmaceutically acceptable salt thereof.

5. The pharmaceutical composition of claim 1, wherein, upon oral administration to a human subject in a daily dose of 20 mg, 50 mg, 100 mg, 200 mg, 400 mg, 700 mg or 1200 mg, the unit dosage form provides a pharmacokinetic result shown below:

| | 20 mg | 50 mg | 100 mg | 200 mg | 400 mg | 700 mg | 1200 mg |
|---|---|---|---|---|---|---|---|
| $C_{max}$ (ng/mL) | about 26.4 | about 56.7 | about 140 | about 459 | about 869 | about 2020 | about 4220 |
| $AUC_{inf}$ (ng * h/mL) | about 50.0 | about 156 | about 433 | about 1140 | about 2730 | about 6710 | about 14500 |
| $t_{1/2}$ (h) | | | | about 3.52 | about 6.04 | about 6.15 | about 7.33 | about 7.69. |

6. The pharmaceutical composition of claim 1, wherein, upon oral administration to a human subject in a dose of about 50 mg BID, about 150 mg BID, about 350 mg BID, or about 600 mg BID, the unit dosage form provides a pharmacokinetic result shown below:

| Day | Dose | Mean $C_{max}$ (ng/mL) | Mean $AUC_{0-12}$ (h * ng/mL) | Mean $t_{1/2}$ (h) |
|---|---|---|---|---|
| 1 | about 50 mg BID | about 70.2 | about 148 | about 3.49 |
| | about 150 mg BID | about 343 | about 809 | about 4.86 |
| | about 350 mg BID | about 1190 | about 2950 | about 5.67 |
| | about 600 mg BID | about 2230 | about 6450 | about 4.15 |
| 10 | about 50 mg BID | about 85.9 | about 252 | about 5.25 |
| | about 150 mg BID | about 320 | about 1170 | about 6.34 |
| | about 350 mg BID | about 1230 | about 4340 | about 6.83 |
| | about 600 mg BID | about 1700 | about 7220 | about 4.66. |

7. The pharmaceutical composition of claim 1, wherein, upon oral administration to a human subject, the $t_{1/2}$ in the human subject is from about 3 to about 8 hours.

8. A pharmaceutical composition comprising:
(a) Compound I-1:

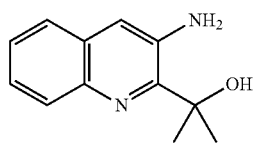

I-1 or a pharmaceutically acceptable salt thereof, as about 15% to about 60% by weight of the composition;

(b) a copolymer of methacrylate and acrylate as about 27.5% to about 80% by weight of the composition;
(c) a filler comprising one or more of mannitol, lactose, and microcrystalline cellulose as about 1.0% to about 6.0% by weight of the composition;
(d) a binder comprising a vinylpyrrolidone-vinyl acetate copolymer binder as about 3.5% to about 14% by weight of the composition;
(e) a glidant comprising a silica glidant as about 0.25% to about 2% by weight of the composition;
(f) a lubricant comprising magnesium stearate as about 0.25% to about 2.0% by weight of the composition; and
(g) optionally, croscarmellose sodium as 0% to about 8.0% by weight of the composition,
    wherein the pharmaceutical composition is a unit dosage form for oral administration to a subject in need thereof, in the form of a tablet or capsule or powder-in-bottle form;
    wherein the subject is a human and upon oral administration to the human subject, the unit dosage form provides an oral bioavailability of at least 70% of the administered dose of I-1 or a pharmaceutically acceptable salt thereof.

9. The pharmaceutical composition of claim 8, comprising:
(a) Compound I-1:

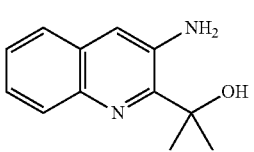

I-1 or a pharmaceutically acceptable salt thereof, as about 25% to about 40% by weight of the composition;
(b) a copolymer of methacrylate and acrylate as about 40% to about 68% by weight of the composition;
(c) a filler comprising one or more of mannitol, lactose, and microcrystalline cellulose as about 1.0% to about 4.0% by weight of the composition;
(d) a binder comprising a vinylpyrrolidone-vinyl acetate copolymer binder as about 4.0% to about 10% by weight of the composition;
(e) a glidant comprising a silica glidant as about 0.25% to about 2.0% by weight of the composition;
(f) a lubricant comprising magnesium stearate as about 0.25% to about 2% by weight of the composition; and
(g) optionally, croscarmellose sodium as 0% to about 8.0% by weight of the composition.

10. The pharmaceutical composition of claim 8, wherein the composition comprises about 10 mg, about 100 mg, about 250 mg, about 300 mg, or about 600 mg of compound I-1.

* * * * *